US010292590B2

United States Patent
Ishii et al.

(10) Patent No.: US 10,292,590 B2
(45) Date of Patent: May 21, 2019

(54) OPTICAL EXAMINATION METHOD AND OPTICAL EXAMINATION DEVICE

(71) Applicant: Ricoh Company, Ltd., Tokyo (JP)

(72) Inventors: Toshihiro Ishii, Miyagi (JP); Yoichiro Takahashi, Miyagi (JP); Toshihide Sasaki, Kanagawa (JP); Masayuki Fujiwara, Miyagi (JP)

(73) Assignee: RICOH COMPANY, LTD., Tokyo (JP)

( * ) Notice: Subject to any disclaimer, the term of this patent is extended or adjusted under 35 U.S.C. 154(b) by 160 days.

(21) Appl. No.: 15/180,194

(22) Filed: Jun. 13, 2016

(65) Prior Publication Data
US 2016/0360966 A1  Dec. 15, 2016

(30) Foreign Application Priority Data

Jun. 15, 2015 (JP) ................................. 2015-119892
Feb. 17, 2016 (JP) ................................. 2016-027491

(51) Int. Cl.
A61B 5/00 (2006.01)
A61B 5/026 (2006.01)
G16C 10/00 (2019.01)

(52) U.S. Cl.
CPC .......... *A61B 5/0059* (2013.01); *A61B 5/0042* (2013.01); *A61B 5/0073* (2013.01); (Continued)

(58) Field of Classification Search
CPC ... A61B 5/0059; A61B 5/0042; A61B 5/0261; A61B 5/0073; A61B 2576/026; (Continued)

(56) References Cited

U.S. PATENT DOCUMENTS

2007/0238957 A1  10/2007  Yared
2011/0098575 A1   4/2011  Stamnes et al.

FOREIGN PATENT DOCUMENTS

EP   1865430 A2   12/2007
JP   2002-000586   1/2002
(Continued)

OTHER PUBLICATIONS

European search report dated Nov. 9, 2016 in corresponding European Patent Application No. 16174233.3.
(Continued)

*Primary Examiner* — Michael W Kahelin
(74) *Attorney, Agent, or Firm* — Oblon, McClelland, Maier & Neustadt, L.L.P.

(57) ABSTRACT

A method of performing an optical examination on a test object and an optical examination device. The method includes obtaining a first detection light quantity distribution that is a detection light quantity distribution obtained for each of a plurality of optical models that simulate the test object, obtaining, using the optical sensor, a second detection light quantity distribution that is a distribution of an amount of light detected on the test object, and selecting based on the first light quantity distribution and the second detection light quantity distribution, an optical model suited to the test object from the plurality of optical models. The optical examination device includes an optical sensor, and a control system to control the irradiation system to obtain an amount of light detected by the detection system.

14 Claims, 62 Drawing Sheets

(52) U.S. Cl.
CPC ............ *A61B 5/0261* (2013.01); *G16C 10/00* (2019.02); *A61B 2562/0238* (2013.01); *A61B 2562/0242* (2013.01); *A61B 2562/046* (2013.01); *A61B 2576/00* (2013.01); *A61B 2576/026* (2013.01)

(58) Field of Classification Search
CPC ...... A61B 2562/046; A61B 2562/0242; A61B 2576/00; A61B 2562/0238; G06F 19/701
See application file for complete search history.

(56) References Cited

FOREIGN PATENT DOCUMENTS

| | | |
|---|---|---|
| JP | 2011-179904 | 9/2011 |
| JP | 2014-055939 | 3/2014 |

OTHER PUBLICATIONS

U.S. Appl. No. 14/913,754, filed Feb. 23, 2016.
Anna Custo, et al., Anatomical Atlas-Guided Diffuse Optical Tomography of Brain Activation, Neuroimage.Author Manuscript;available in PMC Jan. 1, 2011 Jan. 1.
Silvina L. Ferradal, et al., Atlas-based head modeling and spatial normalization for high-density diffuse optical tomography: In vivo validation against fMRI, NeuroImage 85(2014) pp. 117-126.
Florian B. Haeussinger, et al., Simulation of Near-Infrared Light Absorption Considering Individual Head and Prefrontal Cortex Anatomy:Implications for Optical Neuroimaging, Individual Anatomy and Optical Neuroimaging Oct. 2011, vol. 6, Issue 10,e26377.

LINEAR REGISTRATION

NON-LINEAR REGISTRATION

FIG. 4
RELATED ART
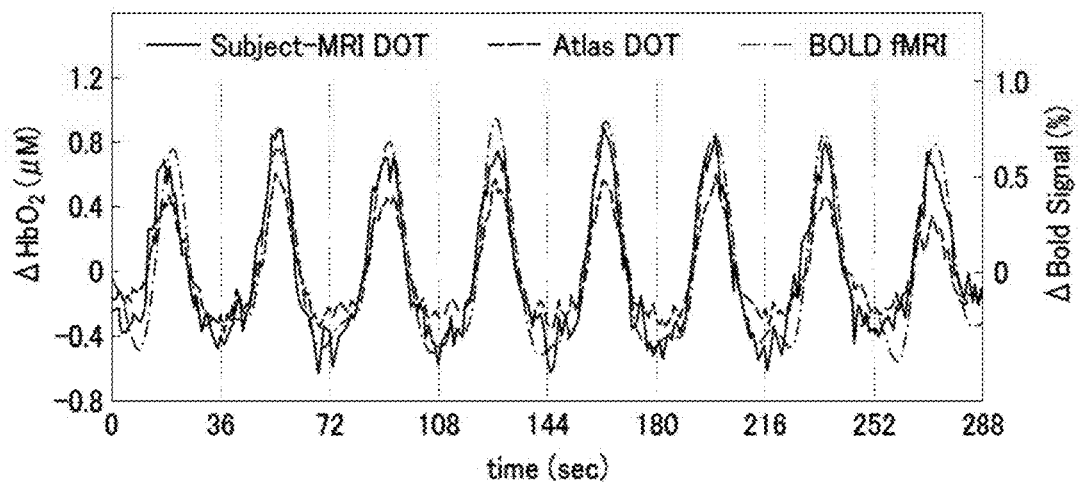
FIG. 5A
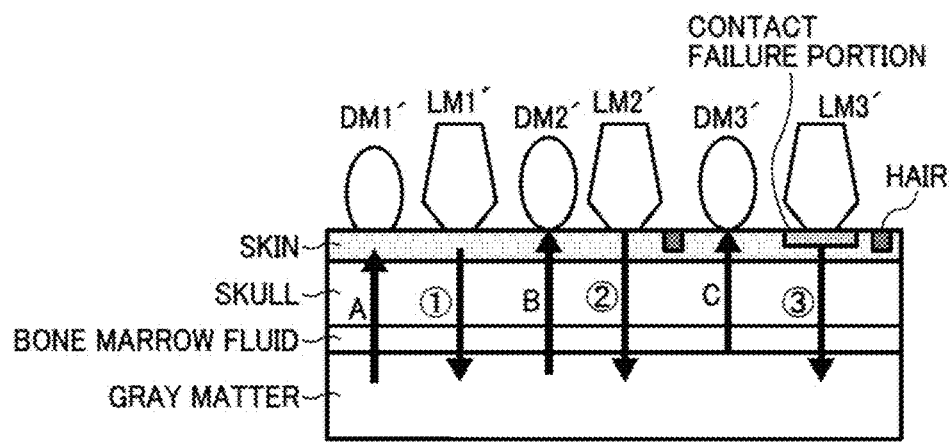
FIG. 5B
|   | ① | ② | ③ |
|---|---|---|---|
| A | 1.0 | 0.1 | 0 |
| B | 1.0 | 1.0 | 0 |
| C | 1.0 | 1.0 | 0 |

FIG. 6A
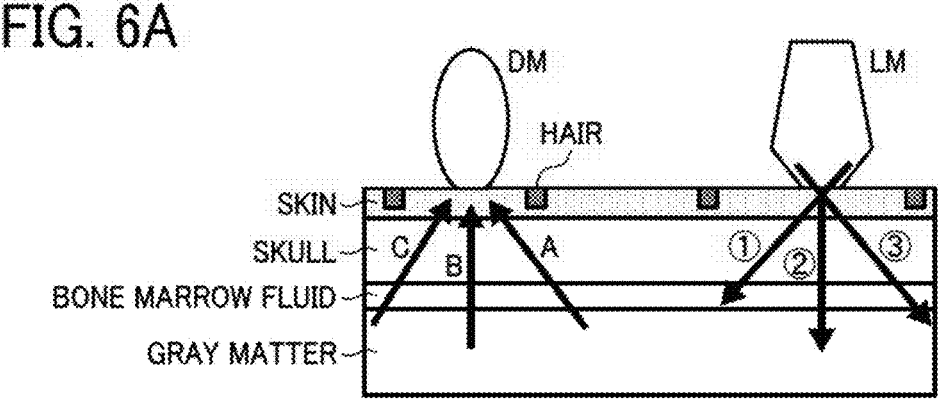
FIG. 6B
|   | ① | ② | ③ |
|---|---|---|---|
| A | 1 | 0.9 | 0.9 |
| B | 0.8 | 0.8 | 0.8 |
| C | 0.7 | 0.7 | 0.5 |
FIG. 7A
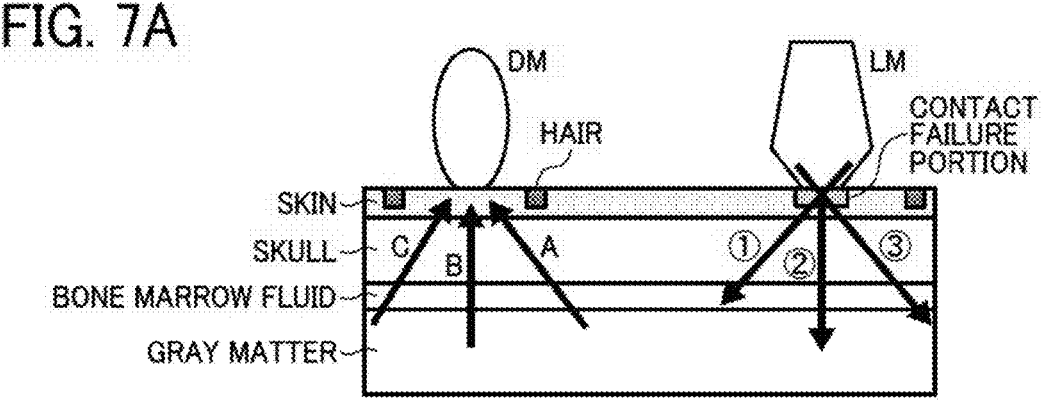
FIG. 7B
|   | ① | ② | ③ |
|---|---|---|---|
| A | 0.9 | 0.8 | 0.8 |
| B | 0.7 | 0.7 | 0.7 |
| C | 0.6 | 0.6 | 0.5 |

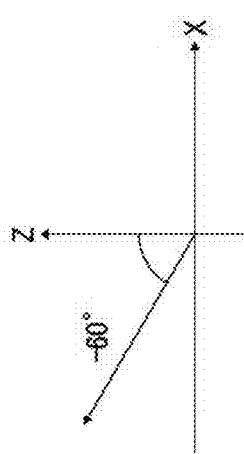
FIG. 27A
FIG. 27B
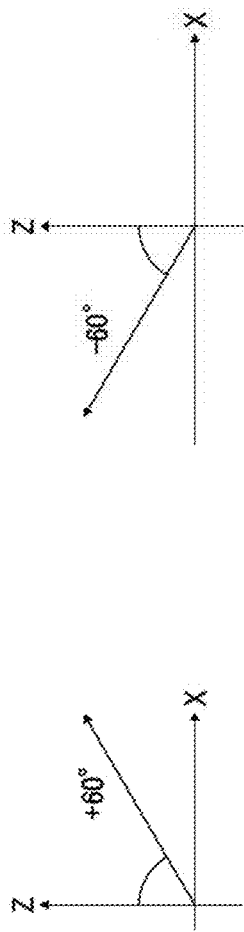
FIG. 28
| MODEL | ABSORPTION COEFFICIENT (mm^-1) | SCATTERING COEFFICIENT (mm^-1) | THICKNESS (mm) | RADIUS OF CURVATURE (mm) | REMARK |
|---|---|---|---|---|---|
| CONTACT FAILURE PORTION | 0.1 | | | | |
| HAIR | 0.05 | 1.0 | 1 | ~ | POSITION |
| SKIN | 0.0159 | 0.8 | 5 | 90 | |
| SKULL | 0.0101 | 1.0 | 5 | 90 | |
| BONE MARROW FLUID | 0.004 | 0.01 | 4 | 90 | |
| GRAY MATTER | 0.0178 | 1.25 | 10 | 90 | |

FIG. 29

| MODEL | CHARACTERISTICS |
|---|---|
| 1 | STANDARD CONFIGURATION |
| 2 | HAIR POSITION (DIRECTLY BELOW LIGHT RECEIVER, DIRECTLY BELOW LIGHT EMITTER) |
| 3 | LOW ABSORPTION COEFFICIENT OF SKIN (PALE SKIN) |
| 4 | HIGH ABSORPTION COEFFICIENT OF SKIN (DARK SKIN) |
| 5 | DECREASED THICKNESS OF BONE MARROW FLUID (YOUTH) |
| 6 | INCREASED THICKNESS OF SKULL (LARGE-BONED) |
| 7 | STEEPENED CURVATURE (SMALL CIRCUMFERENCE OF HEAD) |
| 8 | CONTACT FAILURE MODEL |

FIG. 30A

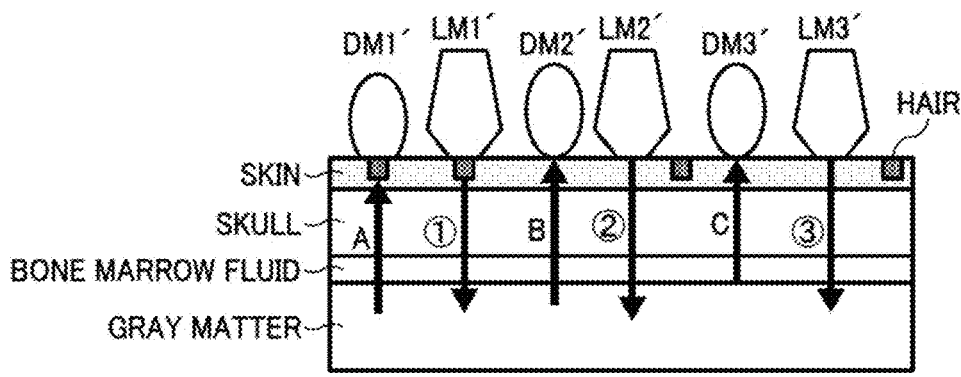

FIG. 30B

|   | ① | ② | ③ |
|---|---|---|---|
| A | 0.5 | 0.7 | 0.1 |
| B | 0.7 | 1.0 | 0.5 |
| C | 0.5 | 1.0 | 1.0 |

FIG. 31A
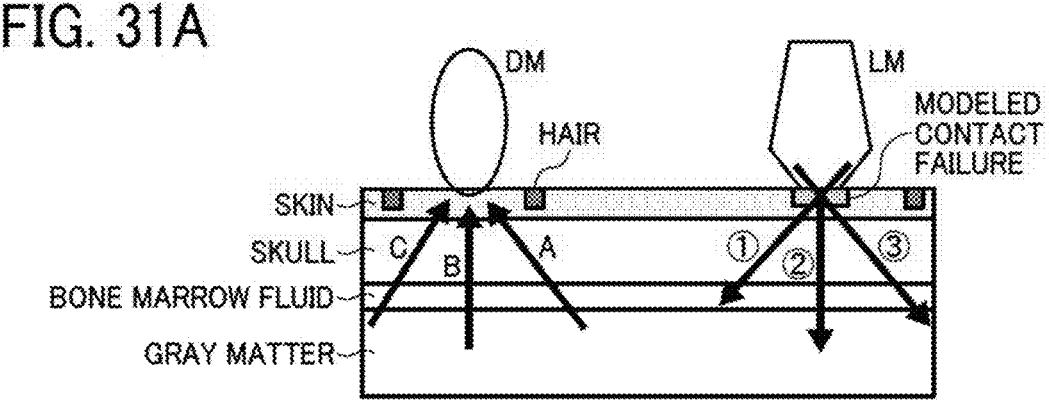
FIG. 31B
|   | ① | ② | ③ |
|---|---|---|---|
| A | 0.9 | 0.8 | 0.8 |
| B | 0.7 | 0.7 | 0.7 |
| C | 0.6 | 0.6 | 0.5 |
FIG. 32A
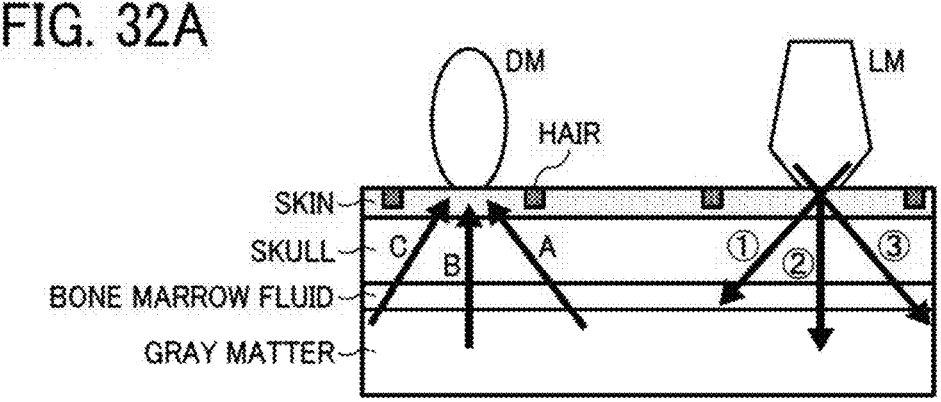
FIG. 32B
|   | ① | ② | ③ |
|---|---|---|---|
| A | 1 | 0.9 | 0.9 |
| B | 0.8 | 0.8 | 0.8 |
| C | 0.7 | 0.7 | 0.5 |

| DEPTH (mm) | CONTROL SAMPLE | SECOND EXAMPLE |
|---|---|---|
| 2 | × | ○ |
| 4 | × | ○ |
| 6 | × | ○ |
| 8 | × | ○ |
| 10 | × | ○ |
| 12 | × | ○ |
| 14 | × | ○ |
| 16 | × | ○ |
| 17 | × | × |

FIG. 68

| MODEL | CHARACTERISTICS | CORRECTION FACTOR α |
|---|---|---|
| 1 | STANDARD CONFIGURATION | 1 |
| 2 | HAIR POSITION (DIRECTLY BELOW LIGHT RECEIVER, DIRECTLY BELOW LIGHT EMITTER) | 1.5 |
| 3 | LOW ABSORPTION COEFFICIENT OF SKIN (PALE SKIN) | 0.8 |
| 4 | HIGH ABSORPTION COEFFICIENT OF SKIN (DARK SKIN) | 1.2 |
| 5 | DECREASED THICKNESS OF BONE MARROW FLUID (YOUTH) | 0.9 |
| 6 | INCREASED THICKNESS OF SKULL (LARGE-BONED) | 0.8 |
| 7 | STEEPENED CURVATURE (SMALL CIRCUMFERENCE OF HEAD) | 1.2 |
| 8 | CONTACT FAILURE MODEL | 1.5 |

| FLORIAN | SCATTERING COEFFICIENT | ANISOTROPY | ABSORPTION COEFFICIENT | REFRACTIVE INDEX |
|---|---|---|---|---|
| SCALP + SKULL | 17.5 | 0.9 | 0.017 | 1.58 |
| CSF | 0.3 | 0.0 | 0.004 | 1.33 |
| GRAY MATTER | 21.5 | 0.9 | 0.090 | 1.40 |

UNIT OF SCATTERING COEFFICIENT
AND ABSORPTION COEFFICIENT: 1/mm

FIG. 86
RELATED ART
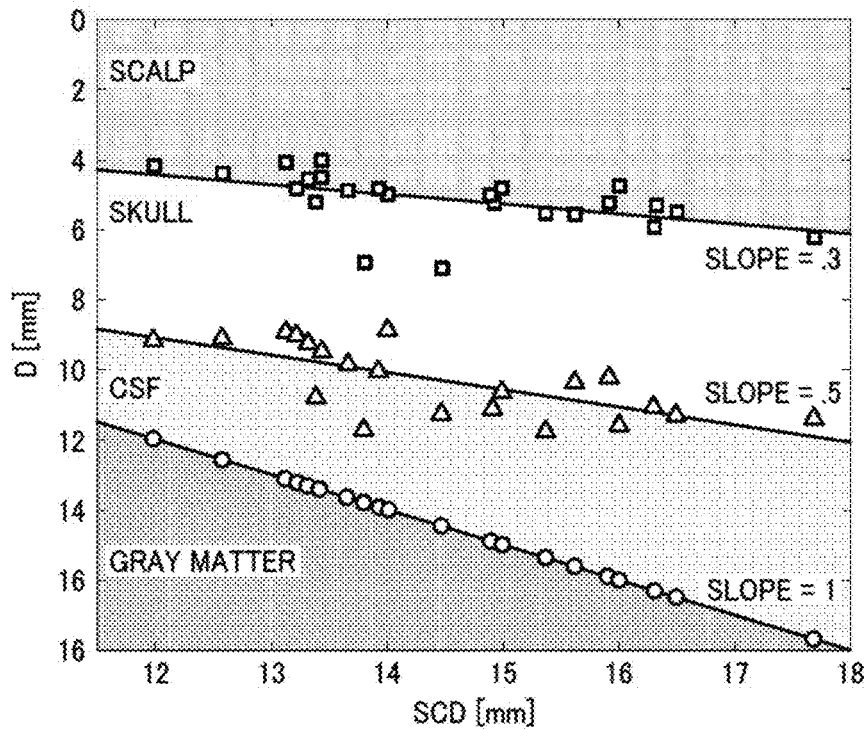
FIG. 87
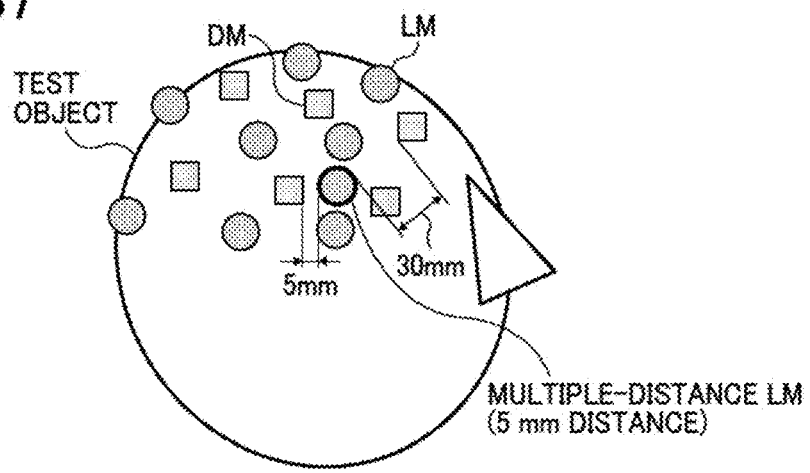
FIG. 88
RELATED ART
$$\Phi(r_s, r_d) = \frac{vS}{4\pi D}\left[\frac{\exp(-\sqrt{3\mu_s'\mu_a}|r_s - r_d|)}{|r_s - r_d|} - \frac{\exp(-\sqrt{3\mu_s'\mu_a}|r_{s,i} - r_d|)}{|r_{s,i} - r_d|}\right]$$

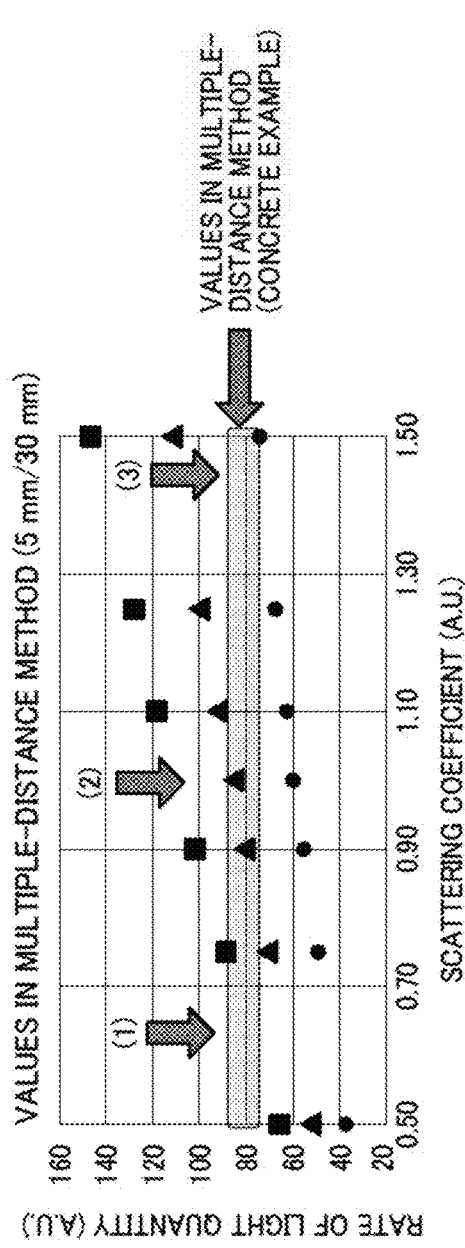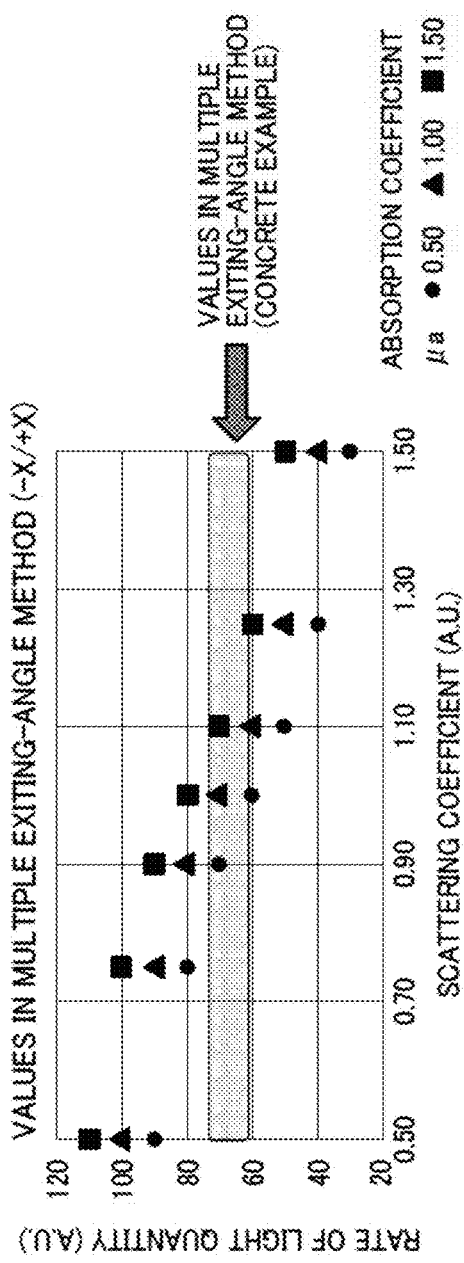

OPTICAL EXAMINATION METHOD AND OPTICAL EXAMINATION DEVICE

CROSS-REFERENCE TO RELATED APPLICATIONS

This patent application is based on and claims priority pursuant to 35 U.S.C. § 119(a) to Japanese Patent Application Nos. 2015-119892 and 2016-027491, filed on Jun. 15, 2015, and Feb. 17, 2016, respectively, in the Japan Patent Office, the entire disclosures of which are hereby incorporated by reference herein.

BACKGROUND

Technical Field

Embodiments of the present invention relate to an optical examination method and an optical examination device.

Background Art

Conventionally, an optical living-body measuring device that irradiates a test object (living body) with light to detect the light that has propagated inside the test object, for examining the test object, is known.

SUMMARY

Embodiments of the present invention described herein provide two related methods of performing an optical examination on a test object and an optical examination device.

In the first method, an optical sensor is used including an irradiation system including at least one light irradiator, and a detection system including at least one photodetector to detect an amount of light that is emitted from the irradiation system to an object to be measured and propagated inside the object to be measured. The first method includes obtaining a first detection light quantity distribution that is a detection light quantity distribution obtained for each of a plurality of optical models that simulate the test object, by performing a simulation where the optical sensor is virtually used; obtaining, using the optical sensor, a second detection light quantity distribution that is a distribution of an amount of light detected on the test object; and selecting, based on the first and second detection light quantity distributions, an optical model suited to the test object from the optical models.

In the second method, an optical sensor is used including an irradiation system including at least one light irradiator configured to irradiate an identical point of an object to be measured with a plurality of light rays that are not parallel to each other, and a detection system including at least one photodetector to separately detect amounts of a plurality of light rays that are emitted from the irradiation system to the object to be measured and have propagated inside the object to be measured. The second method includes obtaining, using the optical sensor, a first detection light quantity distribution that is a distribution of an amount of light detected on the test object; and correcting, using a ratio of a plurality of detection values of the photodetector included in the first detection light quantity distribution, an optical model that simulates the test object.

The optical examination device includes an optical sensor and a control system. The optical sensor includes an irradiation system including at least one light irradiator and a detection system including at least one photodetector to detect an amount of light that is emitted from the irradiation system to a test object and propagated inside the test object. The control system controls the irradiation system to obtain an amount of light detected by the detection system. The control system is configured to, using the optical sensor, obtain a first detection light quantity distribution that is a distribution of an amount of light detected on the test object, and select an optical model suited to the test object from a plurality of optical models that simulate the test object, based on the obtained first detection light quantity distribution and a second detection light quantity distribution that is obtained by simulation where the optical sensor is virtually used, where the second detection light quantity distribution is distribution of an amount of light detected on each one of the plurality of optical models.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

FIG. 4 is another diagram illustrating the correction based on the external shape of a head according to the related art.

FIG. 5A and FIG. 5B illustrate the layout of probes and the light quantity distribution according to the related art.

FIG. 6A and FIG. 6B illustrate the layout of probes and the light quantity distribution according to a first embodiment of the present invention.

FIG. 7A and FIG. 7B illustrate the layout of probes and the light quantity distribution when a contact failure portion is present, according to a first embodiment of the present invention.

FIG. 27A and FIG. 27B each illustrate the propagation angle inside the living body according to the first embodiment of the present invention.

FIG. 28 illustrates the optical constants of each of the layers of the optical models according to the first embodiment of the present invention.

FIG. 29 illustrates the characteristic of the optical models 1 to 8 according to the first embodiment of the present invention.

FIG. 30A and FIG. 30B illustrate the layout of probes and the light quantity distribution according to the related art.

FIG. 31A and FIG. 31B illustrate the layout of probes and the light quantity distribution when a contact failure portion is present, according to the first embodiment of the present invention.

FIG. 32A and FIG. 32B illustrate the layout of probes and the light quantity distribution according to the first embodiment of the present invention.

FIG. 68 is a diagram depicting correction factors for each optical model, according to the second embodiment of the present invention.

FIG. 86 is a diagram illustrating the correlation between the thickness of three layers and the distance between the surface of the scalp and the surface of the brain (cortex), according to the related art (see Plos one e26377 Volume 6 Issue 10 (2011) Florian B. Heaussinger).

FIG. 87 is a diagram illustrating the layout of probes of a multiple distance method, according to the fifth embodiment of the present invention.

FIG. 88 is the equation related to light propagation of a multiple distance method, according to the related art (see 11 Feb. 2002/Vol. 10, No. 3/OPTICS EXPRESS 159).

FIG. 89A is a graph illustrating the relation of the scattering coefficient, absorption coefficient, and the rate of the amount of light of a multiple distance method, according to the fifth embodiment of the present invention.

FIG. 89B is a graph illustrating the relation of the scattering coefficient, absorption coefficient, and the rate of the amount of light of a multiple exit angle method, according to the fifth embodiment of the present invention.

Figure 1A:
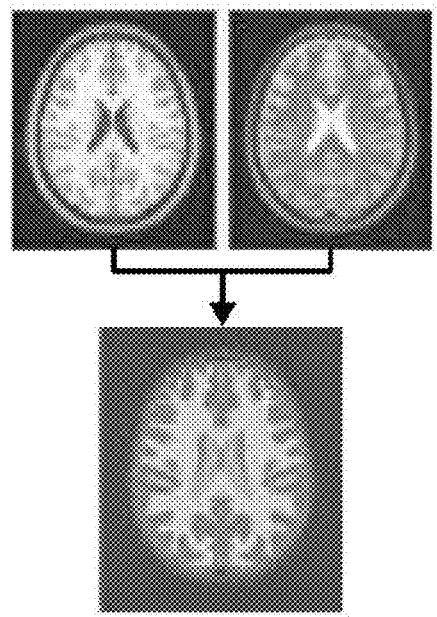
FIG. 1A to FIG. 1F are diagrams illustrating correction based on the external shape of a head according to the related art.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

Before describing a first embodiment of the present invention, related art is firstly described below as an introduction.

In the related art illustrated in FIG. 1A to FIG. 1F (citations from NeuroImage85 (2014), pp. 117-126), images are not taken by directly and individually performing the magnetic resonance imaging (MRI). Instead, FIG. 1A to FIG. 1F illustrate a high-precision brain examination using the MRI images of a standard brain (also called Atlas in Japan) and performing correction based on the data of the external shape of a head.

Figure 1B:
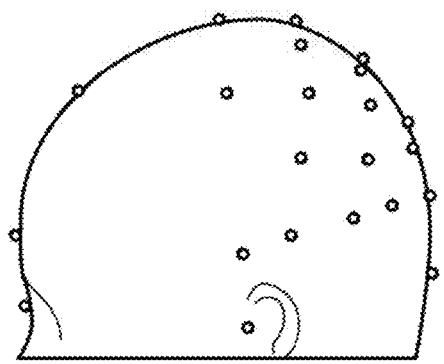

Errors due to individual difference are eliminated by performing correction with reference to the external shape of the head. FIG. 1B illustrates a normal shape of a human head, and such a normal shape of a human head is called a standard brain. The points on the standard brain illustrated in FIG. 1B indicate the installation positions of probes. Here, the probes indicate light irradiators (also called light source modules) or photodetectors (also called detection modules).

Figure 1C:
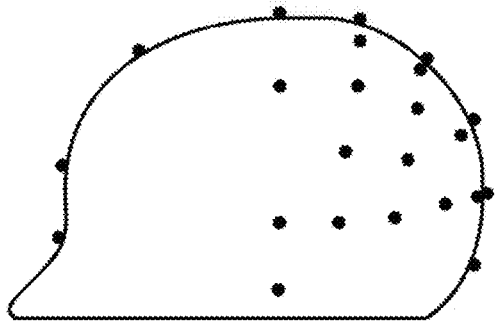
Figure 1D:
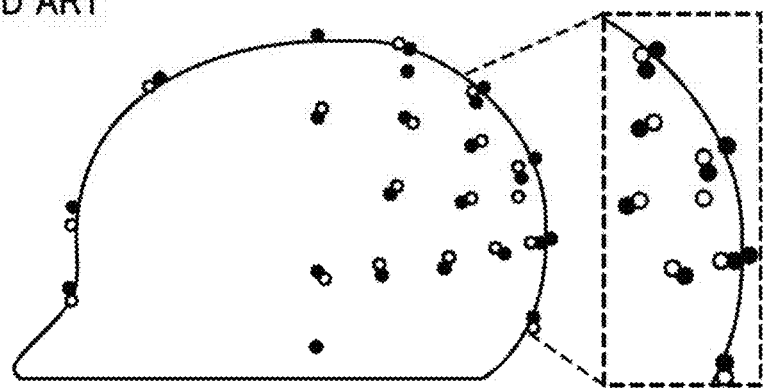
Figure 1E:
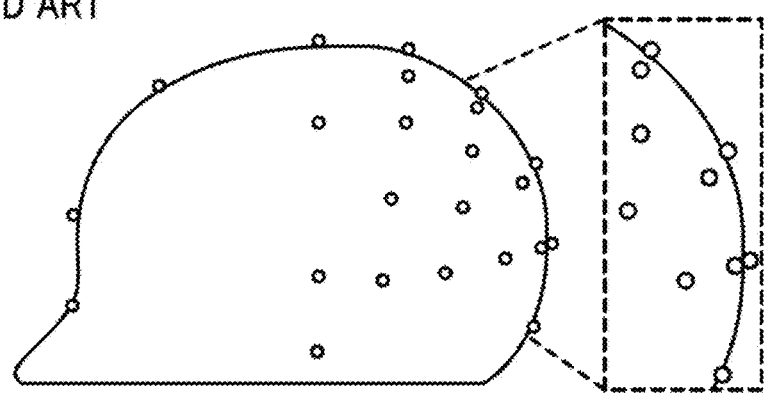
Figure 1F:
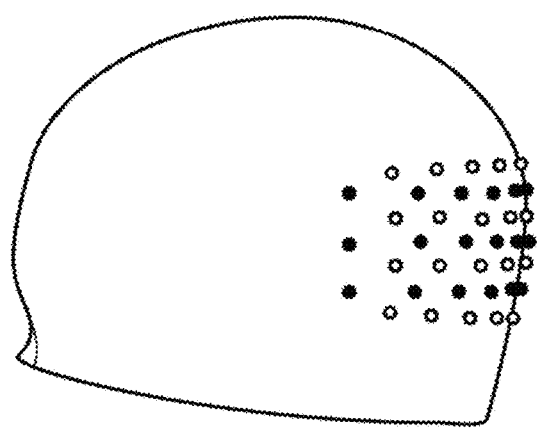
Figure 2:
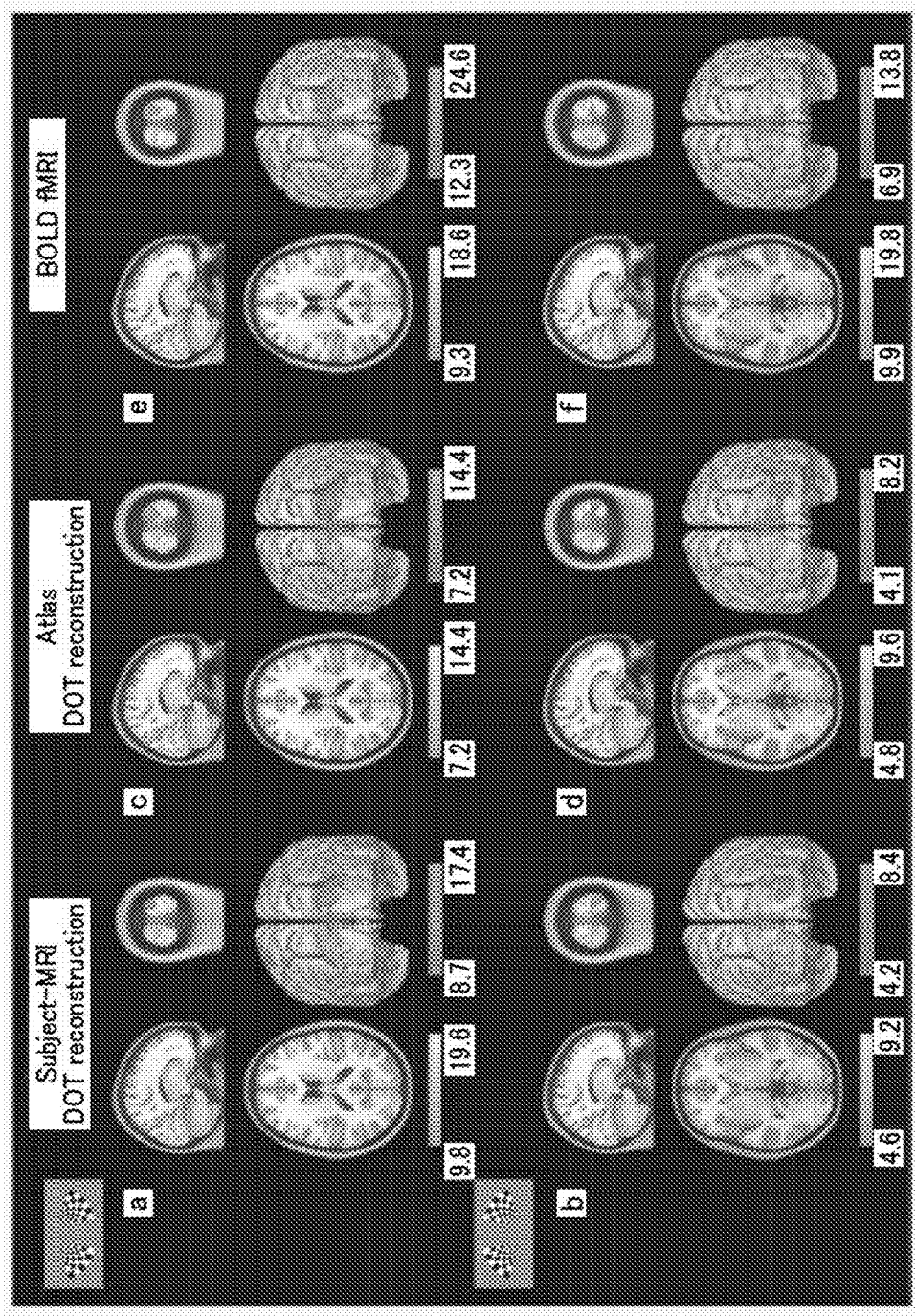
FIG. 2 is another diagram illustrating the correction based on the external shape of a head according to the related art.
Figure 3A:
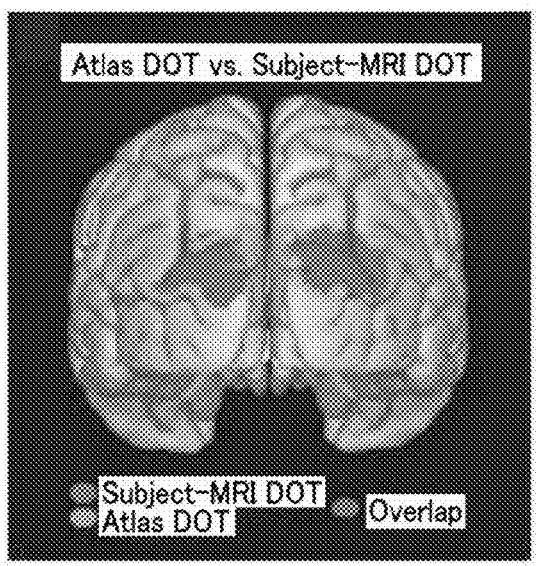
FIG. 3A to FIG. 3D are additional diagrams illustrating the correction based on the external shape of a head according to the related art.
Figure 3B:
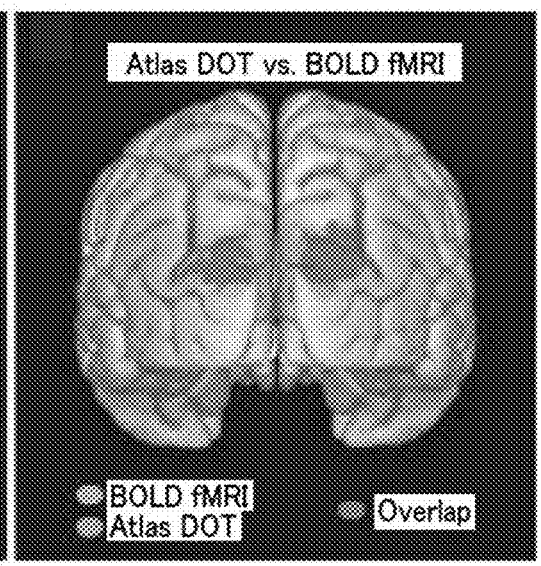
Figure 3C:
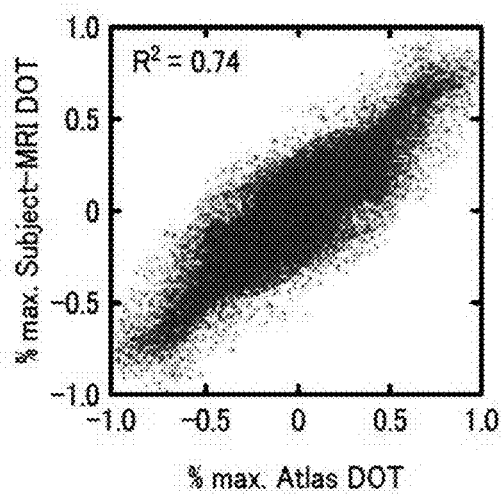
Figure 3D:
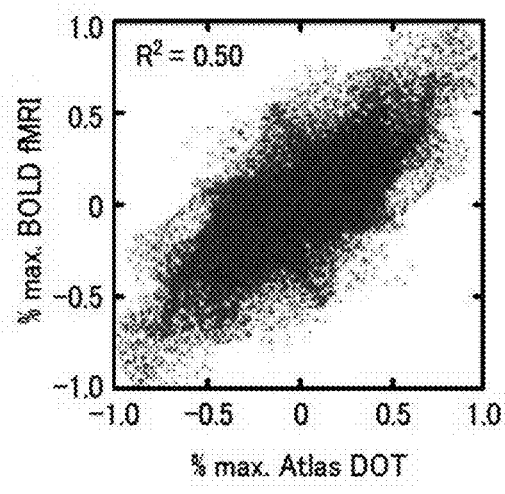

The actual shape of a human head to be measured is illustrated in FIG. 1C, and its external shape is different from that of FIG. 1B. When the shape of the human head is linearly expanded in a simple manner, as illustrated in FIG. 1D, the positions of the probes become slightly misaligned. However, if the shape of the human head is nonlinearly expanded, as illustrated in FIG. 1E, the positions of the probes are precisely aligned.

As illustrated in FIG. 2 and FIG. 3A to FIG. 3D, the images obtained by using a standard brain are almost equivalent to the images obtained by using the MRI or the cerebral blood flow (CBF) images obtained by using the functional MRI (fMRI) where the blood-oxygen-level dependent (BOLD) contrast (reduction in deoxygenated hemoglobin) is observed (refer to the caption "BOLD" in FIG. 2 and FIG. 3A to FIG. 3D).

However, as illustrated in the graphs of FIG. 4 where the changes in cerebral blood flow over time at a certain position are depicted, an error occurs in the amount of cerebral blood flow in the vertical axis. It is to be noted that the error in FIG. 4 is large and the value is nearly doubled by error at some points. As described above, in the changes in the amount of cerebral blood flow over time, there is a possibility that the cerebral blood flow is misread.

In the related art of FIG. 1, a high-density probe method is adopted. In such a high-density probe method, the spaces between probes are made smaller (13 mm) than that of commonly-adopted spaces between probes (30 mm), and the number of probes is increased. Accordingly, the amount of information obtained from the object to be measured increases, and highly precise examination is achieved. However, a high probe density leads to an increased number of probes, for example, to about a four-fold increase. If a hair or the like intervenes between the probes and the scalp (i.e., if there is a contact failure), the amount of light is reduced. Note that the amount of reduction in the amount of light varies depending on the type of probe. Such a varying amount of reduction in the amount of light become a factor in increasing an error. As the number of probes increases, an error occurs more easily. Thus, there is a trade-off between the number of probes and high-precision examination. Moreover, it becomes difficult to select one of the optical models, as will be described later, which serves as a reference for measuring the position of a light absorber in a test object, and an error occurs easily.

More specific explanation is given below with reference to FIG. 5B where the known light quantity distributions are depicted. When the direction at which the light enters an object to be measured (a test object or an optical model) from the light source module LM1' is (1) as illustrated in FIG. 5A, the amount of detection light of the light that propagates through the object to be measured and enters a detection module DM1' in the direction A is a standardized to be (1.0).

FIG. 5B illustrates a light quantity distribution indicating the amounts of the detection light in a matrix with reference to the standardized amount of light as described above, where the directions at which the light enters the test object from three light source modules LM1' to LM3' and the directions at which the light enters three detection modules DM1' to DM3' are A to C. In FIG. 5A, the number of probes is greater (for example, six) than the number of emitted beams (for example, three). For this reason, there are a large number of patterns in which a contact failure occurs between the probes and an object to be measured. When the number of probes is six as illustrated in FIG. 5A, the number of patterns in which a contact failure occurs between the probes and an object to be measured, i.e., patterns in which a contact failure occurs for at least one of the probes, is 64 (=6C1+6C2+6C3+6C3+6C+6C5+6C6). Accordingly, sixty-four optical models are to be prepared. If there are so many optical models, it is difficult to select one optical model.

First Embodiment

By contrast, in a first embodiment of the present invention, as illustrated in FIG. 6A and FIG. 6B, a plurality of light rays enters an identical point of an object to be measured at different angles (for example, three angles) from a light source module LM that includes a plurality of light-emitting units, and a plurality of light rays (for example, three light rays) that has propagated through the object to be measured enters a detection module DM at different angles. In FIG. 6A, the number of probes is fewer (for example, two) than the number of emitted beams (for example, three in a similar manner to FIG. 5A and FIG. 5B). For this reason, a contact failure occurs between the probes and an object to be measured in very much limited patterns.

As illustrated in FIG. 7A and FIG. 7B, a contact failure at a single point according to the present embodiment affects the multiple light-emitting units of a light source module LM at almost the same level. Accordingly, when the number of probes is two as illustrated in FIG. 7A, the number of patterns in which a contact failure occurs between the probes and a test object, i.e., patterns in which a contact failure occurs for at least one of the probes, is 3, and only three optical models are to be prepared. With fewer optical models, it becomes easier to select one optical model.

Figure 8:
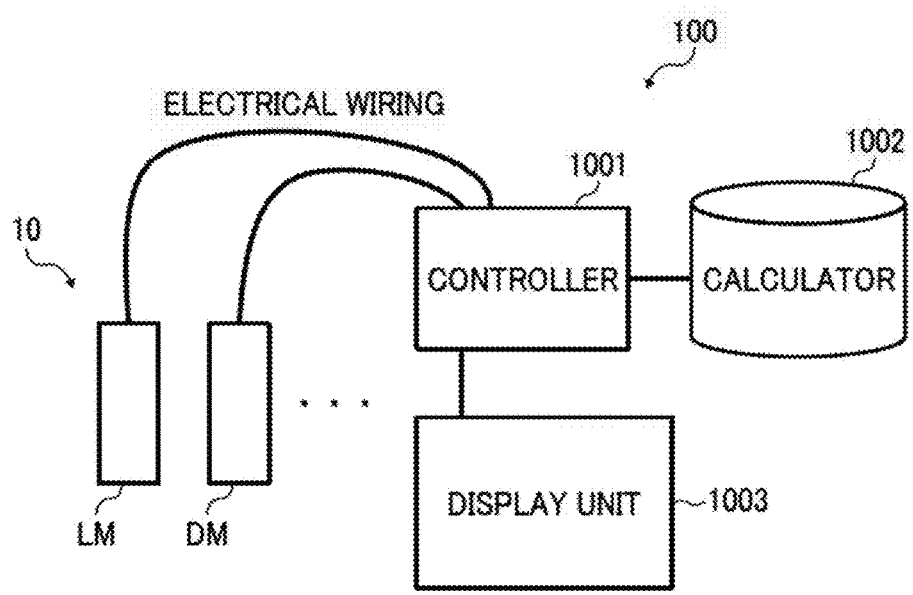
FIG. 8 is a diagram illustrating an outline of the configuration of an optical examination device according to the first embodiment of the present invention.

FIG. 8 is a schematic diagram illustrating the configuration of an optical inspection device 100 according to the first embodiment of the present invention.

For example, the optical inspection device 100 is used for the diffuse optical tomography (DOT). The DOT is a technique in which a test object (scatterer) such as a living body is irradiated with light and the light that has propagated inside the test object is detected to gauge the internal optical properties of the test object. In the DOT, an improvement in resolution leads to a better understanding of the functions of the brain. For this reason, active studies are set out in many research institutions to improve the resolution. In particular, application to aids for differential diagnosis of depression, and application to ancillary equipment of rehabilitation, by detecting the bloodstream inside the brain, can be expected.

Figure 76:
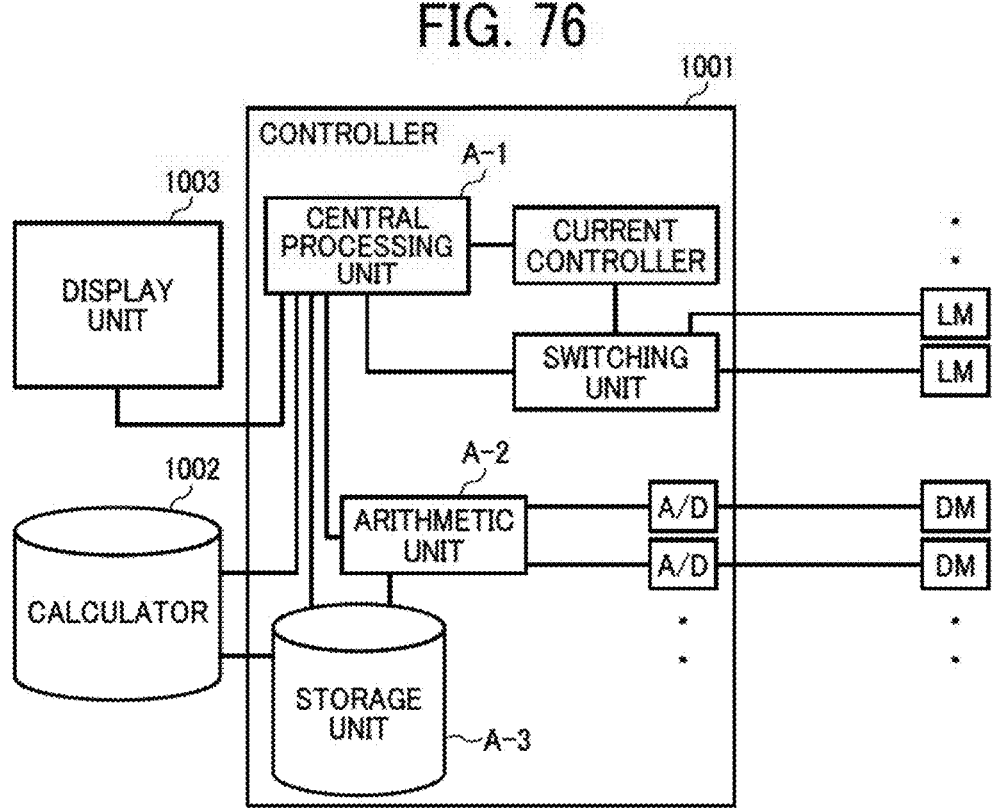
FIG. 76 is a block diagram illustrating the configuration of a controller according to the embodiments of the present invention.

As illustrated in FIG. 8, the optical inspection device 10 includes, for example, a controller 1001, a calculator 1002, and a display unit 1003, and an optical sensor 10 provided with a detection module DM and a light source module LM including a plurality of light-emitting units. The controller 1001 is configured as illustrated in the block diagram of FIG. 76. In the controller 1001, the switching unit is controlled according to the data sent from a central processing unit A-1 to select the light source module LM to emit light. In so doing, the current that is supplied to the light source module LM through the switching unit is controlled by the current controller to have a desired value. The detection result (data) of the detection module DM is analog-to-digital (A/D) converted, and operation such as averaging is performed at an arithmetic unit A-2. The results of the operation performed at the arithmetic unit A-2 is sequentially stored in a storage unit A-3.

In the following description, the light source module LM and the detection module DM may be referred to as a probe when it is not necessary to distinguish between these two elements. In the following description, terms such as a pseudo living body, a living body, and a test object are used. It is to be noted that a pseudo living body and a living body are examples of the test object.

The optical sensor 10 can generally be used as a sensor that detects a light absorber in the test object, but the test object with the highest utility value is a living body. However, as known in the art, it is not always easy to detect the position of the bloodstream (light absorber) of a living body by using an optical sensor. In other words, it is difficult to check the effectiveness (accuracy of detection) of the optical sensor 10 when the test object is a living body.

In order to deal with such situation and achieve versatility, in the present embodiment, a pseudo living body, i.e., whitish liquid in a watertank, is adopted as a test object in which the accuracy of detection can easily be checked. In the following description, such a pseudo living body may be referred to as a phantom.

A first example of the present embodiment is described below.

First Example

In the first example, a method is adopted in which the light beams emitted from a plurality of light-emitting units are deflected by a prism to vary the incident angle to the test object for each of the light beams.

Figure 9:
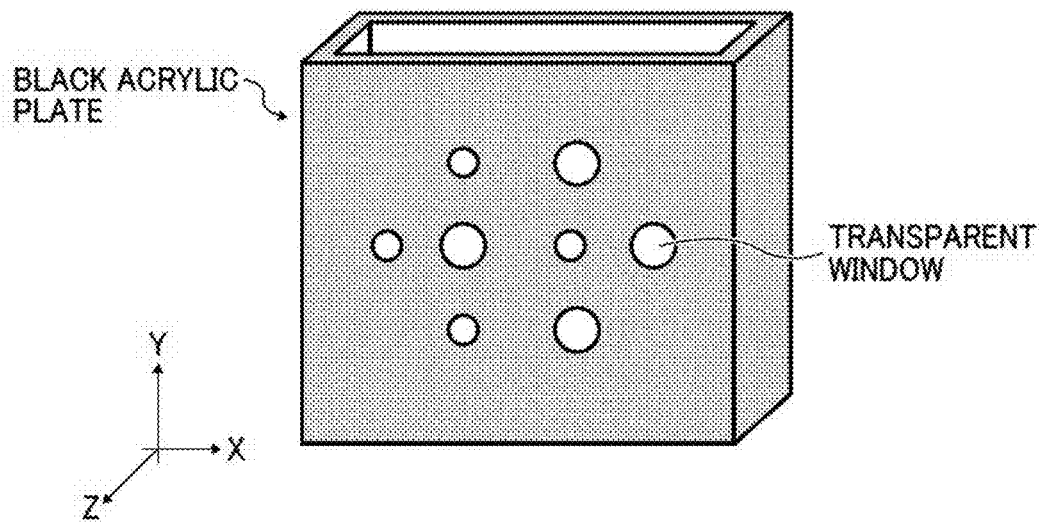
FIG. 9 is a diagram illustrating a watertank for a phantom according to the first embodiment of the present invention.

In the present example, as illustrated in FIG. 9, transparent windows are formed at eight positions on a side wall of a watertank whose walls are made of black acrylic plate. These transparent windows are made of clear acrylic plate. The watertank is filled with an intralipid aqueous solution (ten-times diluted intralipid aqueous solution at a 10 percent concentration). In other words, the pseudo living body used in the first example is an intralipid aqueous solution.

More specifically, black ink is dripped into the intralipid aqueous solution filling the watertank to the degree of about 20 parts per million (ppm). Accordingly, an absorption coefficient and scattering coefficient that are almost equivalent to those of a living body can be achieved. Then, a black light absorber simulating the bloodstream is sunk into the whitish intralipid aqueous solution. In the present example, the light absorber is black polyacetal, and has an approximately 5 millimeters (mm) spherical body in diameter. In order to control the position of such a spherical body, the spherical body is attached to a thin 1 mm metallic rod in diameter, and the rod is connected to an automatic positioning stage. A probe is precisely aligned to each of the transparent windows of the watertank, and is attached thereto.

In the present example, the volume of the watertank is 140 mm×140 mm 60 mm. The thickness of the black acrylic plate is 4 mm. The eight transparent windows are composed of circular transparent windows A and B with varying two sizes (see FIG. 10). There are four transparent windows A and four transparent windows B. The diameter of the transparent window A is 9 mm, and the diameter of the transparent window A is 12 mm. The thickness of both the transparent windows A and B is 1.5 mm.

Figure 10:
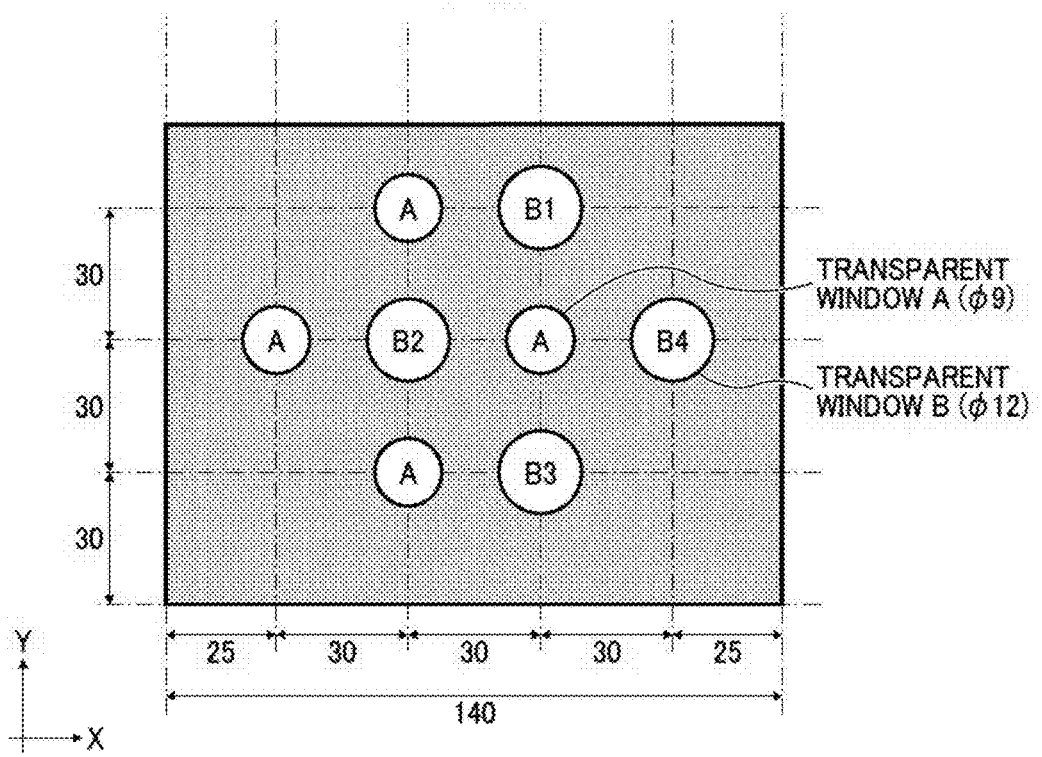
FIG. 10 is a diagram illustrating the layout of a transparent window according to the first embodiment of the present invention.

FIG. 10 illustrates the layout of the eight transparent windows according to the present embodiment. The eight transparent windows are arranged at even intervals in the X-axis direction and the Y-axis direction like a grid such that the transparent windows A and the transparent windows B are next to each other in an alternating manner. In the present example, the detection module DM is attached to each of the transparent windows A, and the light source module LM is attached to each of the transparent windows B (B1 to B4). The distance between the centers of the two neighboring transparent windows is 30 mm.

Figure 11:
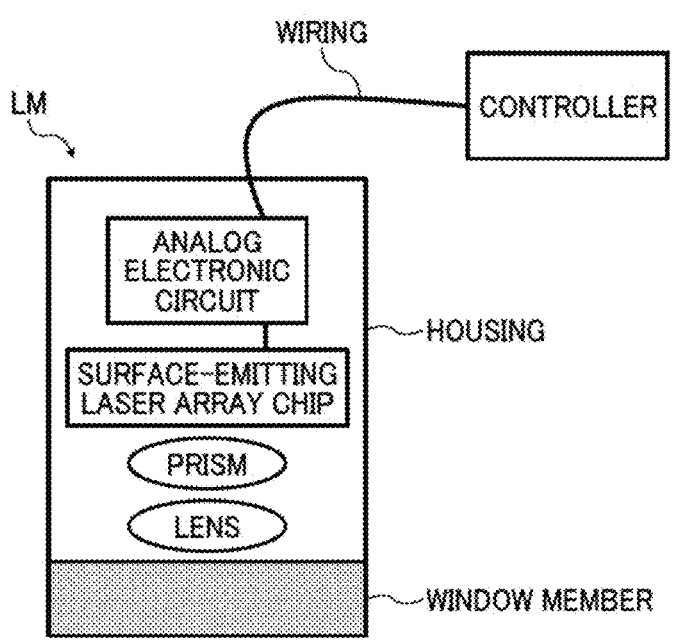
FIG. 11 is a first diagram illustrating an outline of the configuration of a light source module according to the first example of the first embodiment of the present invention.

As illustrated in FIG. 11, the light source module LM includes, for example, a lens, a prism, a ceramic package on which a surface-emitting laser array chip is mounted, a flexible circuit board on which the ceramic package and an analog electronic circuit are mounted, a wiring connected to the flexible circuit board, a connector, a housing accommodating these elements, a window member consisting of transparent resin that contacts the test object. The light source module LM can maintain the amount of light emitted from the light-emitting units at a constant light quantity as the current value is controlled to an appropriate value by a power source unit. The light source module LM is attached to each of the transparent windows B such that a window member contacts the test object (transparent window B) from the +Z side.

Figure 12:
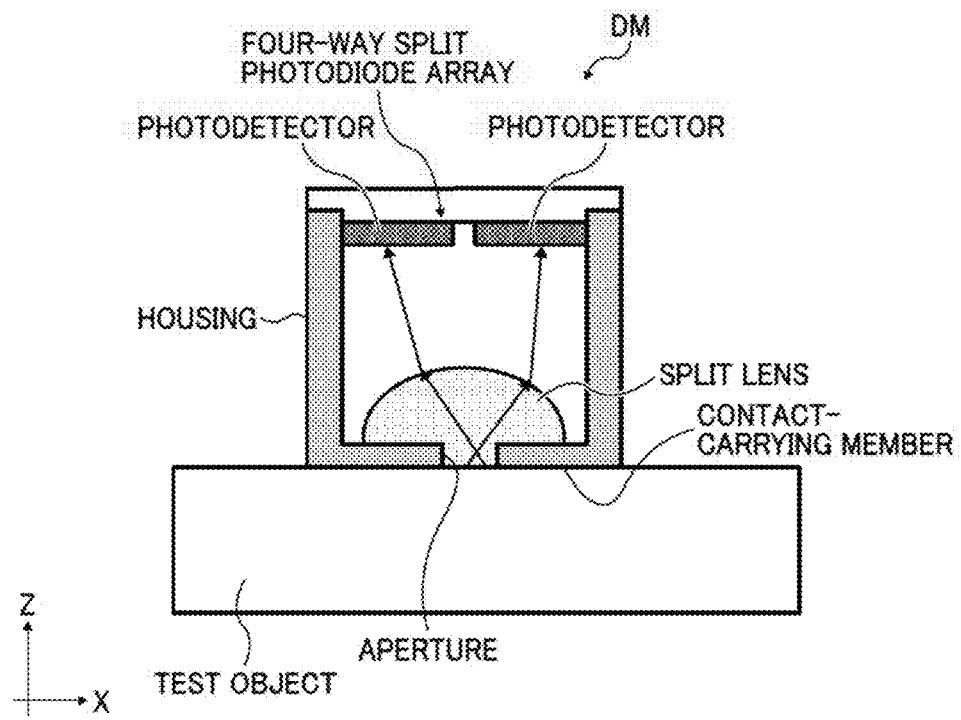
FIG. 12 is a first diagram illustrating an outline of the configuration of a detection module according to the first example of the first embodiment.

As illustrated in FIG. 12, the detection module DM includes a black-resin housing, a contact-carrying member consisting of an elastic body attached to a front end of the housing (i.e., the end on the −Z side), a 3.0 millimeters (mm) hemispheric lens (split lens) in diameter, and a four-way split photodiode array (an array of four photodiodes). The housing has apertures at the front end of the housing and at the other end of the housing in contact with the contact-carrying member. The detection module DM is attached to each of the transparent windows A such that the contact-carrying member contacts the test object (transparent window A) from the +Z side. Note that in FIG. 12, only two of the four photodiodes (photoreceptors) are illustrated.

The split lens is arranged in the proximity of the aperture on the +Z side. Due to this configuration, the light that is emitted from the light source module LM to the test object and then propagates inside the test object enters the split lens through the aperture, and is refracted and exited according to the position at which the light enters the split lens and the direction in which the light enters (see FIG. 12).

The four-way split photodiode array is arranged on the +Z-side of the split lens. Then, the light that has passed through the split lens enters one of the four photoreceptors (photodiodes) of the four-way split photodiode array according to the direction of travel (i.e., the exit direction from the split lens). As described above, the detection module DM can classify the incident angles at which the light exiting from the test object enters the detection module DM into four ranges of angle.

The controller 1001 detects the amount of light received by the four photodiodes (photoreceptor) of the detection module DM attached to each of the transparent windows A (the amount of light received by sixteen photodiodes in total), and converts the detected amount of light into voltage using an operational amplifier. Then, the controller 1001 stores the obtained value of voltage in the storage unit. The data is obtained at the sampling rate of 1 millisecond (msec), and the values obtained in the measurement in 20 seconds (sec) are averaged. In one-time measurement, the data of the sixteen photodiodes is obtained.

Next, the light source module LM is described in detail. As the light source of the light source module LM, a 40-channel surface-emitting laser array chip is adopted. More specifically, a surface-emitting laser array chip provided with 40 vertical-cavity surface-emitting lasers (VCSEL) as light-emitting units is adopted as the light source of the light source module LM.

Figure 13:
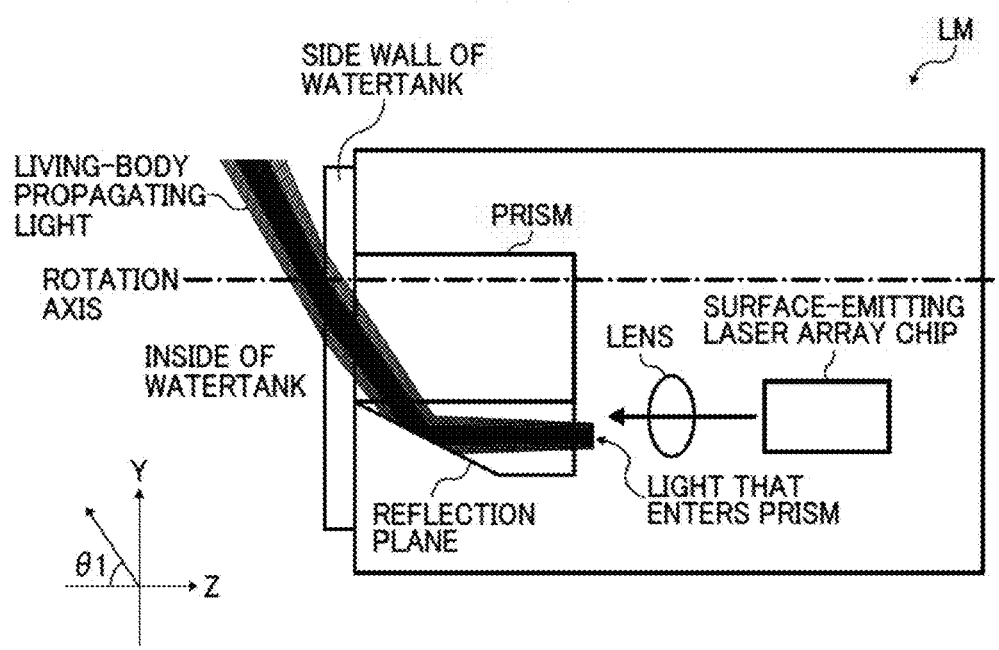
FIG. 13 is a second diagram illustrating an outline of the configuration of a light source module according to the first example of the first embodiment of the present invention.
Figure 14A:
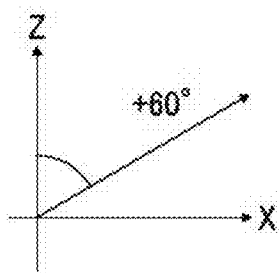
FIG. 14A to FIG. 14D illustrate the propagation angle inside the living body according to the first embodiment of the present invention.
Figure 14B:
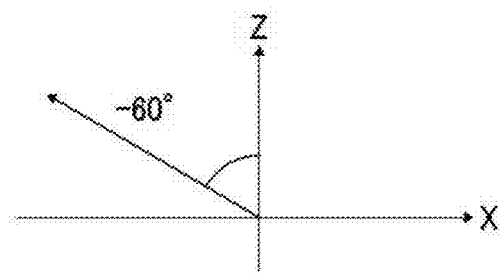
Figure 14C:
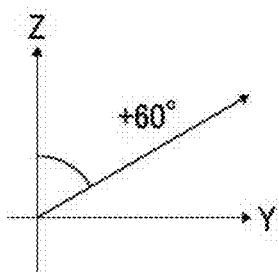
Figure 14D:
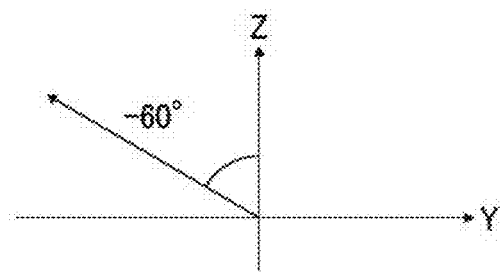

In the optical path of the light emitted from the surface-emitting laser array chip, a 3 mm lens in diameter that approximately collimates the light is arranged (see FIG. 13). The distance between the exit plane (light-emitting surface) of the surface-emitting laser array chip and the principal point (optical center of the lens) is designed to be equal to the focal length f (for example, 9 mm) of the lens. In other words, the surface-emitting laser array chip is arranged such that the exit plane is disposed at the focal point of the lens. Note that "the focal length of the lens" indicates the distance between the principal point and the focal point of the lens.

In the present example, 40 channels are switched on at the same time, and the total output is about 50 milliwatt (mW). As illustrated in FIG. 13, the parallel light emitted from the VCSEL is deflected by the prism.

As the prism, an acrylic prism whose refractive index is equivalent to that of the acrylic watertank as described above is adopted. The reflection plane of the prism is designed in accordance with the diameter of the prism, and the angle of the reflection plane is arranged such that the light that has passed through the lens enters the acrylic watertank at the incident angle of about 50 degrees.

The difference in refractive index between the phantom (intralipid aqueous solution) and the acrylic of the watertank and the prism is designed such that the propagation angle in the phantom becomes about 60 degree (θ1 in FIG. 13) according to the Snell law (the law of reflection). The surface-emitting laser array chip, the lens, and the prism are attached to a rotatable stage disposed on the inner wall of the watertank. The rotatable stage rotates around the rotation axis that extends in the Z-axis direction. In the present embodiment, the rotation axis of the rotatable stage passes through a hole (window member) in the housing. In the following description, the rotation axis of the rotatable stage may be referred to simply as "rotation axis". The surface emitting laser array, the lens, and the prism may be collectively referred to as "irradiation unit". Note that the illustration of the window member is omitted in FIG. 13.

As the rotatable stage and irradiation unit rotate together, the incident angle and direction of the light that enters the prism can be changed. In the present example, as illustrated in FIG. 14A to FIG. 14D, the measurement is sequentially performed in the four directions including the +X, -Y, +Y, and -Y directions. Accordingly, the measurement is performed for the four positions of the four light source modules LM (B1 to B4) and for the four directions. As a result, the measurement is performed sixteen times in total. In between the prism and the watertank, gel-like resin with the refractive index equivalent to that of the prism and the watertank is filled. Accordingly, the refraction or reflection between the prism and the watertank can be prevented.

Next, a method of measuring the internal information of a test object is described below with reference to the flowchart of FIG. 15.

Firstly, a probe is set (step T1). As described above, the probe indicates the detection module DM and the light source module LM. Here, the probe to be set includes four detection modules DM and one light source module LM. The four detection modules DM are attached to each of the four 9 mm transparent windows A in diameter as illustrated in FIG. 10. The one light source module LM is attached to the transparent window B1 as illustrated in FIG. 10.

Next, the 40 channels (light-emitting units) of the light source module LM are instructed to emit light at the same time (step T2). The light-emission intensity is determined such that the current value becomes about 50 milliwatts (mW) in total. The light emitting period is about 20 seconds (sec), and the detection values of the four photodiodes of the detection module DM are read during the light emitting period (step T3). The data (detection values) obtained at 1 millisecond (msec) intervals are averaged. Then, the averaged detection values, i.e., the mean value of detection values, is stored in the storage unit (step T4).

Next, the wavelength of the exiting light is switched, and the steps T2 to T4 are performed again (steps T5 and T6). In the present embodiment, one of the wavelengths 780 nm and 900 nm may be selected. More specifically, two types of light source modules LM with different oscillation wavelengths (780 nm band and 900 nm band) are prepared in advance, and the light source modules LM are replaced. By so doing, the wavelengths of the exiting light can be switched.

In the present example, the measurement is performed for the four directions including the +X direction, +Y direction, -X direction, and -Y direction (steps T7 and T8). More specifically, the steps T2 to T6 immediately after the step T1 are performed upon arranging the prism in the +X direction. Next, the prism is rotated to the +Y direction. In this state, the steps T2 to T6 are repeated. Next, the prism is rotated to the -X direction. In this state, the steps T2 to T6 are repeated. Next, the prism is rotated to the -Y direction. In this state, the steps T2 to T6 are repeated.

Next, the position where the light source module LM is attached is sequentially changed from the transparent window B1 to the transparent windows B2, B3, and B4, and the measurement is performed again for the four directions (steps T9 and T10). Then, the position of the light absorber is shifted, and the measurement is performed again for the four directions and the four positions where the light source module LM is attached (steps T11 and T12).

The stored data is labeled as r(s, i, n) (i=1, 2, 3, ... M; n=1, 2, 3, ... K) with the light absorber and r(0, i, n) (i=1, 2, 3, ..., M; n=1, 2, 3, ..., K) without the light absorber. "i" denotes the numbers assigned to the respective detection modules DM.

"n" denotes the numbers assigned to the respective groups. Next, the difference Δr (i, n) is calculated.

Figure 15:
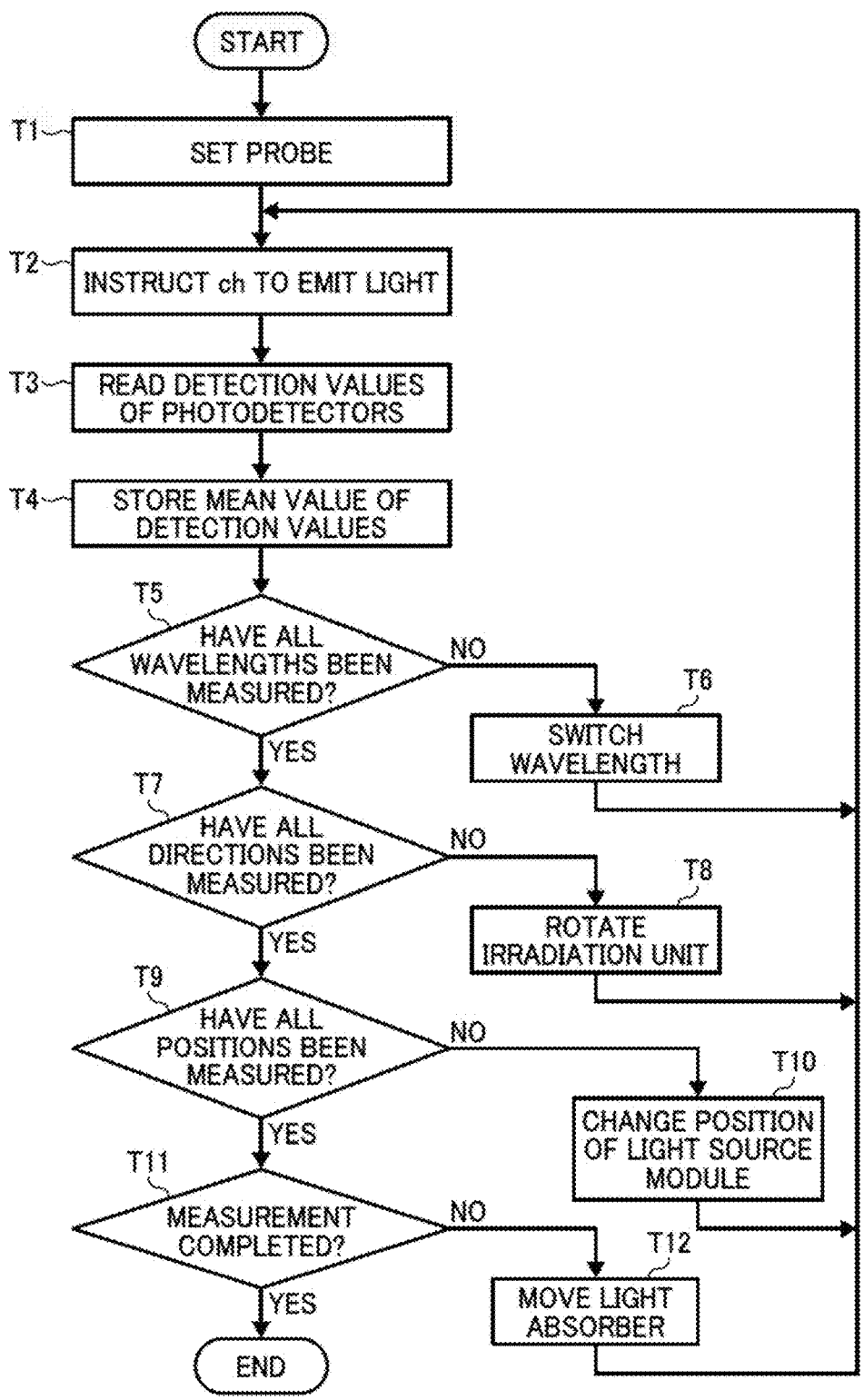
FIG. 15 is a flowchart of a method of measuring the internal information of a test object according to the first embodiment of the present invention.

Next, a method of calculating the position of the light absorber (the optical properties of the pseudo living body) according to the result of the measurement obtained by the measurement method as depicted in the flowchart of FIG. 15 is described. In this method, an inverse-problem estimation algorithm is adopted. In order to solve an inverse problem, firstly, measurement and simulation are performed and a sensitivity distribution is calculated using a forward problem. Then, the data obtained by the subsequent measurement is imported, and an inverse problem estimation is performed based on the value in the imported data.

Figure 16:
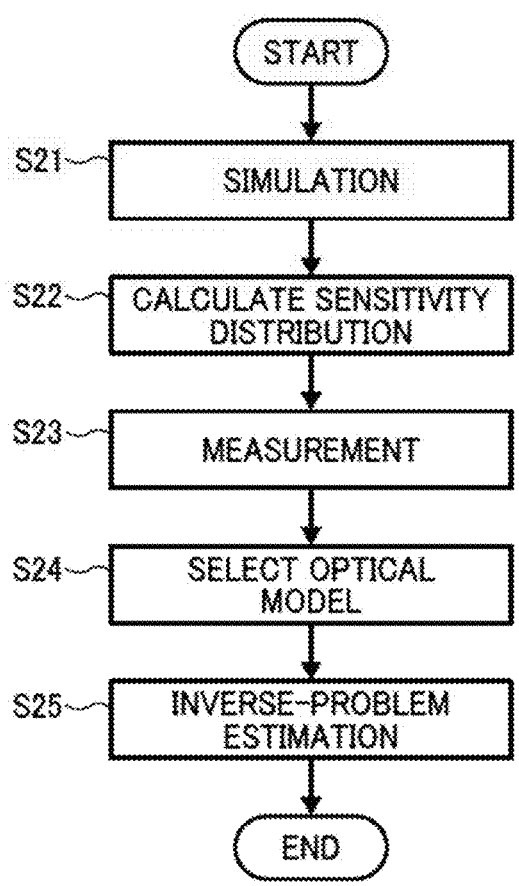
FIG. 16 is a flowchart of an optical examination method (i.e., light absorber position estimation processes) according to the first embodiment of the present invention.

Next, the steps of an optical examination method according to the first embodiment are described below with reference to the flowchart of FIG. 16.

In a first step S21, the Monte Carlo simulation is performed. The Monte Carlo simulation is performed for each of the eight kinds of optical models 1 to 8 depicted in FIG. 17 to FIG. 24, using the optical sensor 10 in a virtual manner. The optical models are the virtual models that simulate a test object (i.e., the human head in the present embodiment). In the present embodiment, the optical models have five layers.

In the present embodiment, each of the optical models have the multilayered structure in which a gray matter layer, a bone marrow fluid layer, a skull layer, a skin layer, and a hair layer are laminated in that order from the deepest layer to the most surface layer. In particular, the optical model 1 simulates the standard brain described above, and is also referred to as a standard model In the present embodiment, each of the light source modules LM can emit light in four directions, and each of the detection modules DM can detect light in four directions. The Monte Carlo simulation is performed in accordance with such emission and detection of the light source modules LM and the detection modules DM.

In the next step S22, the sensitivity distribution is calculated and obtained for each of the optical models based on the measurement results of the Monte Carlo simulation (i.e., the results of the virtual measurement).

In the next step S23, the sensitivity distribution is calculated and obtained by performing the measurement (i.e., physical measurement) using the optical sensor 10 for the test object with the same layout of probes as when the Monte Carlo simulation was performed.

In the next step S24, one of the optical models is selected. More specifically, the optical model is selected whose sensitivity distribution is most applicable to (most similar to) the sensitivity distribution of the test object.

In the next step S25, an inverse problem estimation is performed based on the sensitivity distribution of the selected optical model and the sensitivity distribution of the test object to estimate the positions of the light absorbers inside the test object. The details are described below step by step.

Figure 77:
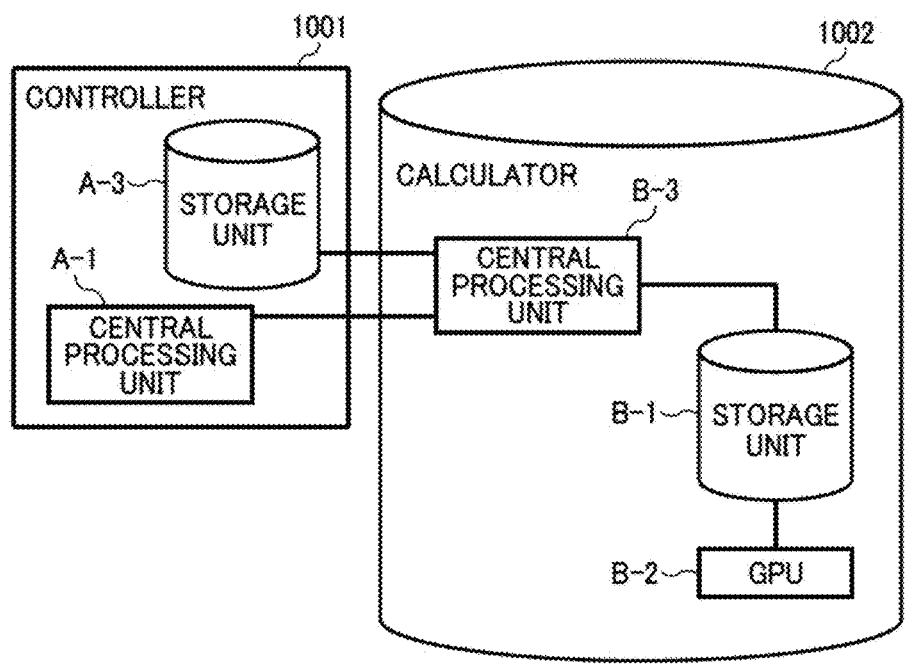
FIG. 77 is a block diagram illustrating the configuration of a calculator according to the embodiments of the present invention.

FIG. 77 is a block diagram of the calculator 1002. Data such as that of the position of the modules (probes) and the refractive index or shape of the living body, which is used for the Monte Carlo simulation as will be described later, is stored in the storage unit B-1. The above-mentioned forward problem is performed based on this data. In the calculation of this forward problem, a graphics processing unit (GPU) (multigraphics processor) capable of parallel computation is used. The use of such a GPU dramatically speeds up the calculation compared with the conventional configuration. The sensitivity distribution obtained by this calculation is stored again in the storage unit B-1. This calculation result and the measurement result stored in the storage unit A-3 are input to the central processing unit B-3, and the central processing unit B-3 performs the inverse problem estimation. The estimation result is displayed on the display unit 1003 through the central processing unit A-1 (see FIG. 76).

Conventionally, in the forward problem calculation, it was believed that the light in a scatterer such as a living body disperses in an almost isotropic manner. For this reason, a simulation using a diffusion equation with less computational complexity has been adopted. In recent years, however, it has been reported, for example, in academic conferences, that the light propagation in a minute area of a few millimeters is in fact anisotropic in a living body. In order to perform a simulation in view of such anisotropy, a transport equation or the Monte Carlo simulation is performed.

In the present embodiment, the light emitted from the light source is deflected so as to enter the test object. For this reason, a diffusion equation known in the art is not sufficient to perform a simulation in view of the data of the incident angle. A method in which a transport equation is used has been suggested. However, it is known in the art that a method in which a transport equation is used takes an enormous length of time.

In order to deal with such a situation, the Monte Carlo simulation is adopted in the present embodiment. The Monte Carlo simulation is a method in which the condition for the photons to disperse in a scattering medium are stochastically expressed by a random variable and the macroscopic behavior of the photons is observed. More specifically, the behavior of the photons is modeled with the assumption that the photons move in a medium and collision occurs every time the photons travel a certain distance and that the directivity of the photons changes accordingly. The average distance traveled by the photon in the above model is the mean free path, and the mean free path is defined by a scattering coefficient. The changes in direction are defined by the anisotropy g. The repeated collisions and how the photon propagates in a specified area are recorded. By calculating a myriad of photons in the model as described above, the behavior of the light in the scattering medium can be simulated. By using the Monte Carlo simulation, the path of the dispersion of one photon is recorded.

In the Monte Carlo simulation according to the present embodiment, a 120 m×120 mm×60 mm three-dimensional area is calculated where the number of photons is 109 and the voxel is a 1 mm cube. In the present embodiment, the scattering coefficient, absorption coefficient, anisotropy, and the refractive index of the scattering medium are 7.8 mm-1, 0.019 mm-1, 0.89, and 1.37, respectively, and these values are almost equivalent to the scattering coefficient, absorption coefficient, anisotropy, and the refractive index of a human scalp. The above-described phantom (intralipid aqueous solution) is prepared to satisfy these values, and a simulation is performed under the same situations as those of the phantom with all aspects such as the propagation angle and the positions of the light source module LM and the detection module DM to calculate a sensitivity distribution.

In this simulation and calculation, it is assumed that the number of photons that have passed through the position r of the voxel is φ0(r). In particular, it is assumed that the number of photons that have passed through the position r of the voxel where the position of the light source module LM is "rs" is φ0(rs, r). Next, the light source module LM is disposed where the detection module DM was disposed and the same number of photons is calculated again. When the detection module DM is disposed at "rd", it is assumed that the number of photons that have passed through the position of the voxel is φ0(r, rd).

As the optical path is reversible, this product is proportional to the number of photons that pave passed through the position r of the voxel, emitted from the light source module LM, and have entered the detection module DM. The product is normalized by the number φ0(rs, rd) of all the photons that enter the detection module DM. As a result, the following sensitivity distribution A(r) is obtained.

$$A(r) = \frac{\phi_0(rs, r)\phi_0(r, rd)}{\phi_0(rs, rd)} \qquad \text{[Formula 1]}$$

The sensitivity distribution A(r) indicates the degree of influence on the amount of detection at the position r. The sensitivity distribution A(r) indicates how much the detection value changes due to the presence of a light absorber at the position r of the voxel.

Figure 25:
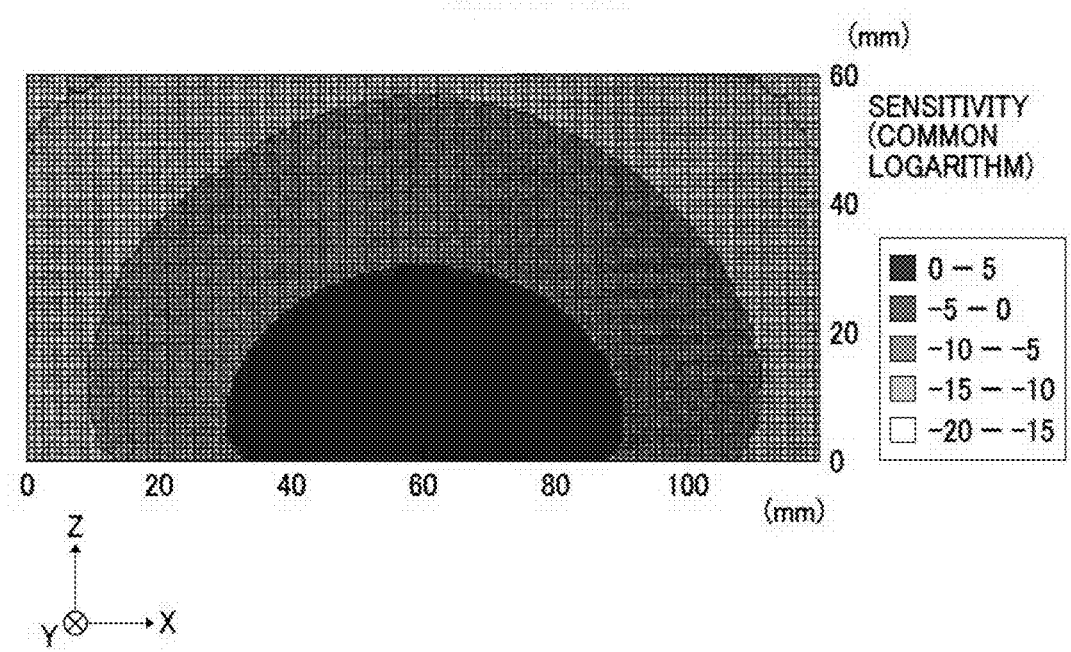
FIG. 25 is a first diagram illustrating the sensitivity distribution at a photodiode, according to the first embodiment of the present invention.

An example of the sensitivity distribution calculated as above is illustrated in FIG. 25. In FIG. 25, the light source module LM and the detection module DM are disposed at (X, Y, Z)=(45, 60, 0) and (X, Y, Z)=(75, 60, 0), respectively. As the voxel is a 1 mm cube, the measurement unit is equivalent to that of these values. The sensitivity of the voxel at each position is indicated by the base 10 logarithm (common logarithm) base.

Figure 26:
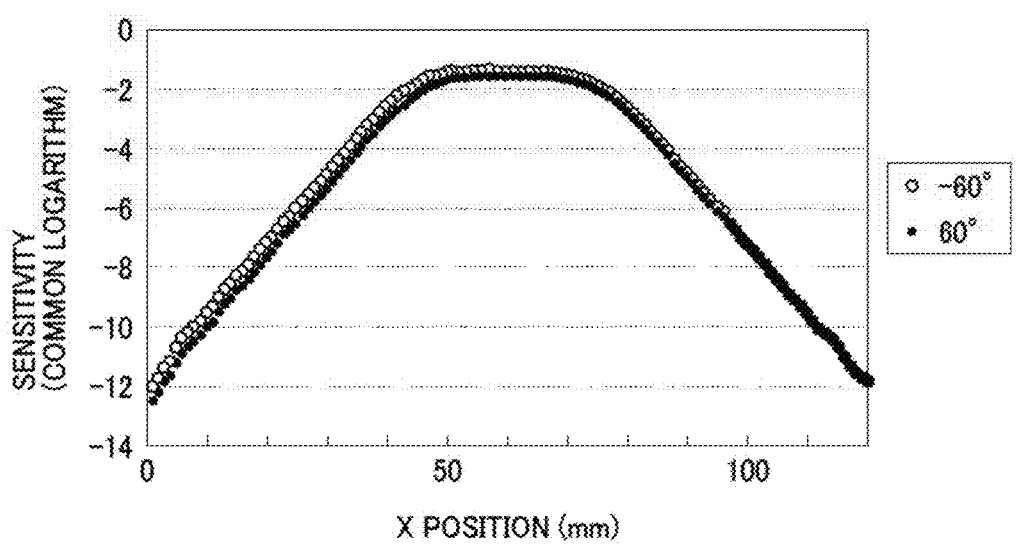
FIG. 26 a second diagram illustrating the sensitivity distribution at a photodiode, according to the first embodiment of the present invention.

Next, the line with Y=60 and Z=10 of the voxel (x, y, z) is extracted from the sensitivity distribution illustrated in FIG. 25. Then, the extracted line is plotted where the vertical axis and the horizontal axis indicate the sensitivity and the x position, respectively. The result of such extraction and plotting is illustrated in FIG. 26. More specifically, FIG. 27A and FIG. 27B illustrate the propagation angles inside the living body when the angle which the light forms with the X-axis on the plane where the Y-axis is the normal line is +60 degrees and −60 degrees, respectively.

As illustrated in FIG. 26, there are differences in the sensitivity distribution between the case of +60 degrees and the case of −60 degrees. Such differences serve as a guiding principle to determine whether the improvement in resolution becomes possible. In other words, the presence of a difference between these two sensitivity distributions indicate that the propagation paths of the light rays emitted from two light sources are different from each other. If the propagation paths are the same, the sensitivity distributions should be about the same as well even if the propagation angle varies. As the propagation paths from the two light sources are different from each other, the light rays from the two light sources collect different information.

This fact is significant for the inverse problem estimation as will be described later. As described above, the propagation of light is not simple isotropic scattering, but is slightly anisotropic on the order of several millimeters. It is considered that such a difference on the order of several millimeters becomes a factor in achieving inverse problem estimation with the resolution on the order of several millimeters. Such a sensitivity distribution is to be calculated for all the propagation angles and detection angles of all the pairs of probes (i.e., all the pairs of the light source modules LM and detection modules DM) in the phantom.

The difference in angle as illustrated in FIG. 27A and FIG. 27B cannot be detected in the simulation where isotropic propagation is assumed and a diffusion equation is used. Such a difference can be obtained as a result only after the Monte Carlo simulation is used as in the present embodiment. As described above, the amount of information can be increased in the present embodiment by obtaining the difference in incident angle. In other words, the Monte Carlo simulation enables a high-precision inverse problem estimation. In a similar manner, such an increased amount of information improves the precision of the correction using that information.

As described above, the Monte Carlo simulation is performed for each of the eight kinds of optical models 1 to 8 depicted in FIG. 17 to FIG. 24. Note that in FIG. 17 to FIG. 24 only one light source module LM and only one detection module DM are illustrated. This is for the purposes of simplification, and the actual arrangement is the same as that of the phantom illustrated in FIG. 9.

In so doing, the optical constants illustrated in FIG. 28 are used as the optical constants of the five layers and contact failure portion of the optical model. Note that as the hair in the present embodiment has a thickness of about 100 micrometers (μm) as known in the art, the absorption coefficients are adjusted to the voxel of 1 millimeter (mm) for the Monte Carlo simulation. Moreover, a plurality of optical models are to be prepared, for example, for the varying positions of the hair. For example, the hair may have a voxel directly below a light source module LM or detection module DM or have one layer between the light source module LM or detection module DM.

FIG. 29 depicts the detail of the eight optical models 1 to 8 illustrated in FIG. 17 to FIG. 24. In these models of FIG. 29, with reference to the optical model 1 as a standard configuration (standard model), the characteristics of a test object or the installation state of probes are taken into consideration in the other seven optical models 2 to 8. In the Monte Carlo simulation, various kinds of optical models may be prepared and no limitation is indicated by these eight optical models 1 to 8, and a plurality of levels may be prepared for the changes in each parameter.

Figure 17:
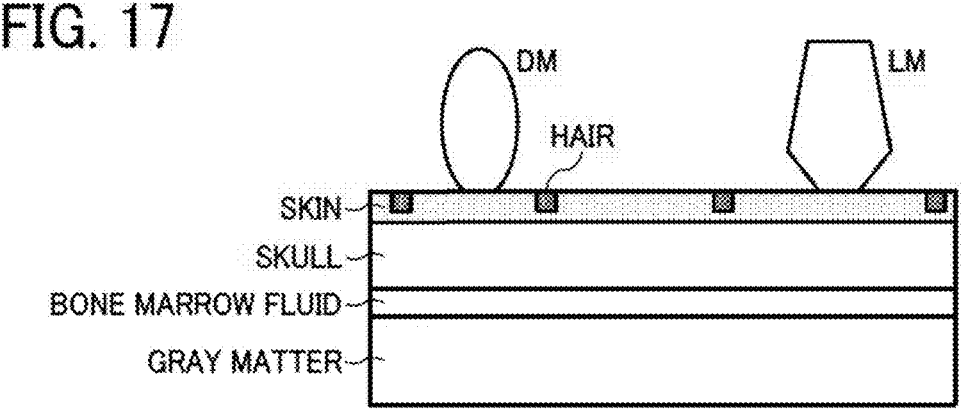
FIG. 17 illustrates an optical model 1 according to the first embodiment of the present invention.
Figure 18:
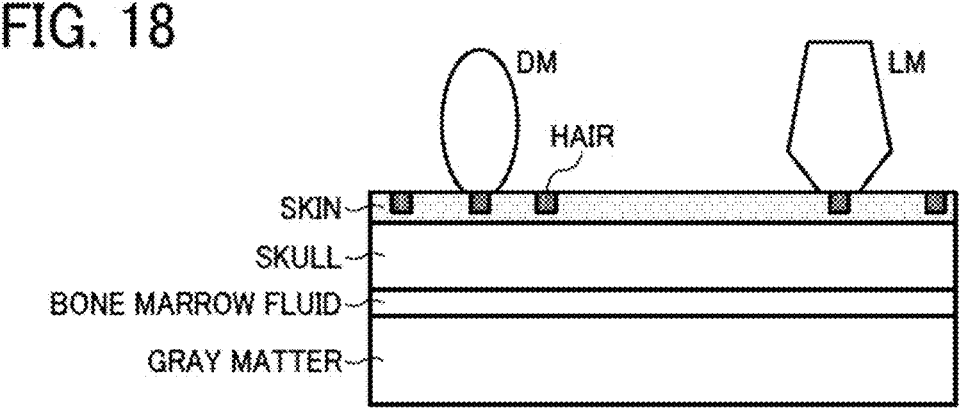
FIG. 18 illustrates an optical model 2 according to the first embodiment of the present invention.

For example, the optical model 1 of FIG. 17 is different from the optical model 2 of FIG. 18 in the position of the hair. The optical sensor 10 according to the present embodiment includes a light source module LM that emits a plurality of light rays that are not parallel to each other to an identical point of an object to be measured, and a detection module DM that receives the multiple light rays separately that are emitted from the light source module LM to the object to be measured and have propagated inside the object to be measured. The optical sensor 10 according to the present embodiment is highly robust with respect to the position of a hair, which is advantageous over the related art. In other words, the information of the multiple light rays that are emitted from an identical point of the object to be measured and have taken different propagation paths gives an advantage in reducing the influence of the noise made by the hair depending on the position of the hair. The amounts of the multiple light rays in all the directions that are emitted from the light source module LM directly above the hair are reduced in almost the same way.

By contrast, in a known method in which probes are disposed with high density, the propagation paths of a large number of light rays may be differentiated. Accordingly, the obtainable amount of information increases. However, the probability that a probe is placed on a hair also increases, and the noise due to hairs increases as well as a result. Such a situation is illustrated in FIG. 30A and FIG. 30B. FIG. 30A illustrates a case in which hairs exist directly below the detection module DM1' and the light source module LM1'. In such a case, the amount of detection light (A) at the DM1' and the amount of irradiation light (1) decrease than the amounts of the detection light and the amounts of the irradiation light at the other detection modules DM and light source modules LM. Accordingly, as depicted in the matrix of FIG. 30B, the value of the matrix element (1, A) (hereinafter, such a value may be referred to as a "matrix value") in the light quantity distribution becomes smaller than that of the other matrix elements. Such a difference has nothing to do with the amount of cerebral blood flow, and thus such a difference is an error. When a light source module LM capable of emitting a plurality of light rays that are not parallel to each other and a detection module DM capable of dividing the incident angle are used as described above, the use of an optical model with five layers including hairs as a layer leads to a significant improvement in the accuracy of detection compared with when an optical model with four layers not including a layer of hair.

In the cases described above, an error factor is found to be a contact failure due to the presence of hairs. However, such an error may be generalized as an error in the optical properties for probes. In actuality, a contact failure has the greatest probability of causing an error in the system.

In the present embodiment, hairs are set to a parameter (layer structure) for the optical models. However, an absorption coefficient or a scattering coefficient may be added to the parameters as parameters that go beyond the assumption.

As illustrated in FIG. 31A and FIG. 31B, also in the present embodiment, the presence of a contact failure almost evenly affects the entirety of the light source module LM, and the amount of irradiation light decreases all amounts of irradiation light (1) to (3). In this case, all the amounts of irradiation light decrease at almost the same rate. Accordingly, when (1, A) is standardized, the distribution becomes almost the same as that of the standard structure (see FIG. 32A and FIG. 32B). However, the values in FIG. 31B are standardized according to the standard structure, and the value of (1, A) indicates 0.9. The other values of the matrix elements in FIG. 31B are almost equivalent to the values obtained by multiplying the values in FIG. 32B by 0.9. In other words, the light quantity distribution of the matrix of FIG. 31B is similar to the light quantity distribution of the matrix of FIG. 32B.

If there are a plurality of contact failure portions as in the related art illustrated in FIG. 30, the light quantity changes only at the probes where contact failure occurs. This leads to an error. In order to avoid such situation, the contact failures are to be modeled only in cases where a plurality of light rays that are not parallel to each other are made enter an identical point of an object to be measured, and simulation is performed in advance. By so doing, the errors due to contact failures can be eliminated. Accordingly, the light quantity can be corrected with high precision. Moreover, inverse problem estimations can be performed with high precision.

If the contact failures are modeled in a similar manner to the hairs, it becomes easier to correct errors when a model is to be selected. In a light source module LM where a plurality of light rays that are not parallel to each other enter an identical point of an object to be measured, a reduction in light quantity due to a contact failure at a portion where the light source module LM is mounted occurs almost evenly for the multiple light rays that are emitted from the light source module LM. Accordingly, it is not necessary to prepare a large number of optical models in view of such contact failures (in the following description, such optical models may be referred to as "contact failure models").

In the related art illustrated in FIG. 30, there are a large number of contact portions where an object to be measured contacts a plurality of light source modules LM each of which emits a single ray of light. For this reason, it is necessary to prepare a large number of contact failure models. If there are a large number of models as above, an error tends to occur in selecting a model. Fewer models enables high-precision model selection and high-precision correction.

In the present embodiment, virtual measurement is performed in computer simulation for each of the optical models, and physical measurement is performed on a test object. Then, the sensitivity distribution of each optical model and the sensitivity distribution of the test object are prepared as described above based on the measurement results. By preparing such sensitivity distributions, as illustrated in FIG. 32B, a light quantity distribution where no cerebral blood flow is considered can be prepared. In FIG. 32B, the amount of the detection light of the light that enters a detection module DM in the direction A when the direction at which the light enters an optical model from the light source module LM1 is (1) is a standardized to be 1. FIG. 32B depicts a light quantity distribution indicating the amounts of the detection light in a matrix with reference to the standardized amount of the detection light, for each of the incident directions (1) to (3) at which the light enters the optical models from the light source modules LM and the incident directions A to C at which the light enters the detection modules DM. In the light quantity distribution according to the present embodiment, varying results can be obtained for each of the eight optical models 1 to 8 depicted in FIG. 29.

The first light quantity distribution obtained from the sensitivity distribution of the optical models is compared with the second light quantity distribution obtained from the sensitivity distribution of the test object, to select an optical model that is most suited to the test object. In the present embodiment, an optical model where the first and second light quantity distributions are best harmonized is selected. In so doing, calibration is to be performed in advance of the physical measurement. Such calibration is performed using a black box in which polyoxymethylene (POM) resins are disposed and a guide is attached to guide the probes to desired positions. Due to such calibration, a high degree of reproducibility can be achieved. In the present embodiment, the light quantity distribution of the optical models is compared with the light quantity distribution of the test object, and an optical model is selected based on the results of the comparison. However, no limitation is intended thereby. The sensitivity distribution of the optical models may be compared with the sensitivity distribution of the test object, and an optical model may be selected based on the results of the comparison.

In order to select appropriate one of the optical models, the model is selected where each of the values in the matrix has the smallest error between the physical measurement and the virtual measurement. More specifically, the difference in the matrix value is calculated between ((1), A) in the physical measurement and ((1), A) in the virtual measurement. Next, the difference in the matrix value is calculated between ((2), B) in the physical measurement and ((2), B) in the virtual measurement. This calculation is repeated in sequence, and the sum total of the squares of the differences in the values of the corresponding matrix elements between the physical measurement and the virtual measurement is calculated. Then, the optical model with the smallest value in the above sum total is determined to be the optimum one.

An optical model may be selected using other various kinds of methods. For example, instead of the selection method as described above where the least squares of the matrix are calculated, a selection method where a classification is performed by preconditions and then correction or weighting are performed, as will be described later, may be adopted.

Such a selection method according to the present embodiment is described below with reference to the flowchart of FIG. 33. In the present embodiment, the selection method includes as a precondition a method of eliminating a model where a contact failure has occurred (for example, a model affected by hairs). In a subsequent step of the method adopted in the present embodiment, correction is performed so as to mostly eliminate a difference with neighboring probes and weighting is performed in view of influence in the depth direction.

Figure 34:
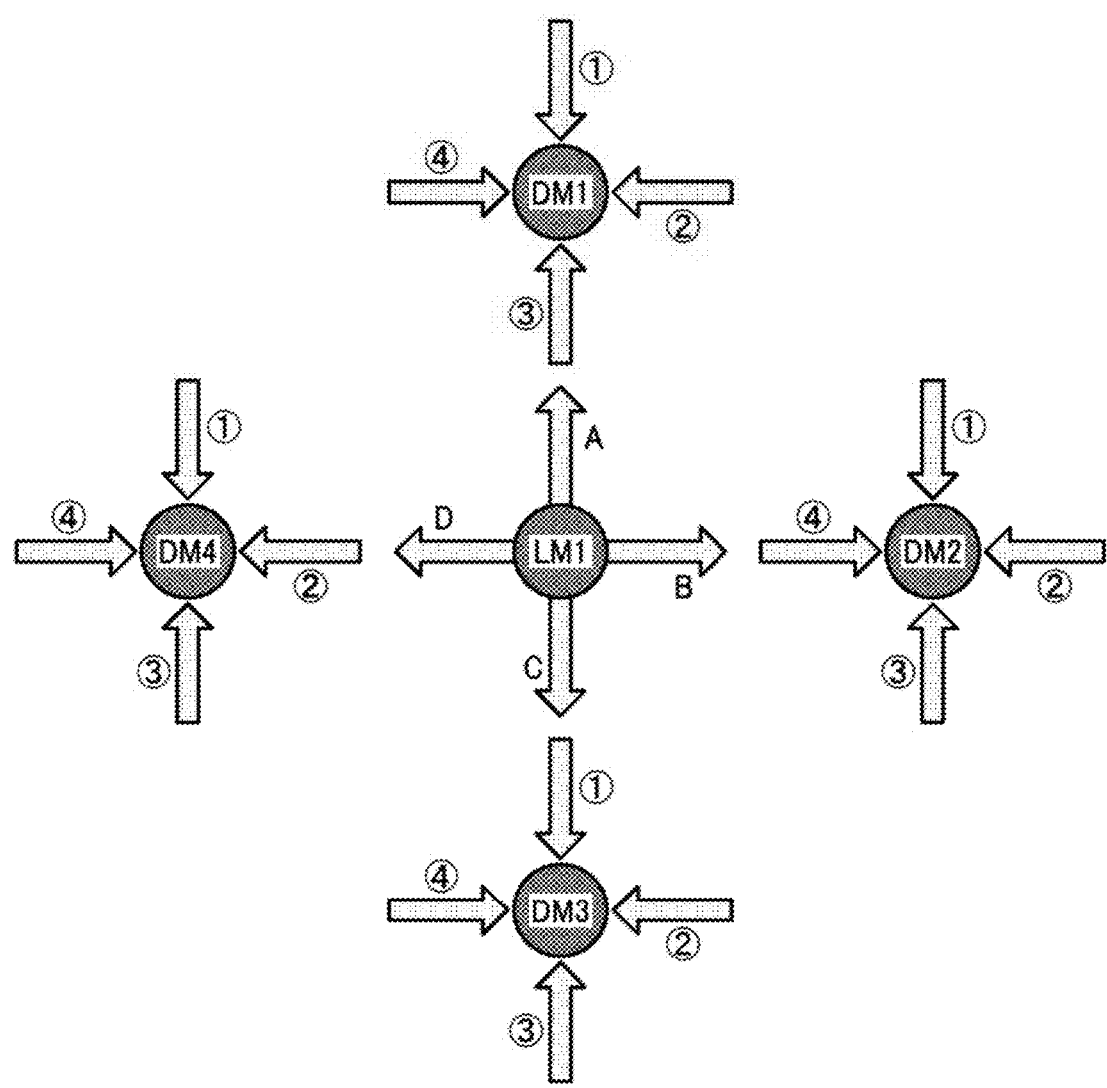
FIG. 34 is a diagram illustrating a method of detecting a singular point of a single light source module LM in four directions and a method of removing such a singular point, according to the first embodiment of the present invention.

Firstly, the virtual measurement results between neighboring two probes are compared with each other (steps S31 to S36). As illustrated in FIG. 34, four detection modules DM are adjacent to one light source module LM in the layout of the light source modules LM and the detection modules DM. As described above, each of the detection modules DM can detect light in such a manner that the angle is divided into four directions. As the light source module LM also emits light in four directions, the matrix described above includes 4×4 rows and columns.

When the values in the matrix are compared among four detection modules DM (step S31), there are some cases in which reduction in light quantity singularly occurs only in one of the detection modules DM, for example, due to a contact failure caused by hairs. Singular points are quantified, and whether or not a singular point is present is determined with reference to a prescribed threshold (step S32). In the present embodiment, whether or not a singular point is present is determined depending on how much the light quantity of the detection module DM with the smallest light quantity among four detection modules DM (here, such a detection module DM is referred to as DM (Min)) deviates from the average of the matrix of the other three detection modules DM.

In so doing, the values of the light quantity of (3, A) of DM1 (4, B) of DM2, (1, C) of DM3, and (2, D) of DM4 illustrated in FIG. 34 are compared with each other. More specifically, these four values are averaged, and the obtained average is standardized. Assuming that the average of three detection modules DM is "1" and when the DM (min) is equal to or less than 0.9, such a value (0.9) is determined to be a singular point.

In an experiment with the present embodiment, phantoms are examined. For this reason, the threshold γ for the DM (min) is set to a relatively high value of 0.9. However, when an examination is performed on a human head, the threshold γ is appropriately selected depending on the site of the head, for example, a forehead portion or a parietal portion. It is assumed that the thickness of the skull, including a forehead portion, is approximately even within the rectangular area (60 mm per side) whose vertices are the adjacent four detection modules DM. This is because it is considered that the consistency of the cerebral blood flow is equal to or less than several millimeters. The magnitude of such consistency is referred to as the sparse value β and is used in the following description. Accordingly, the sparse property can involve physiological characteristics.

In the present embodiment, the sparse value is appropriately varied according to the site or the age of a test object. This is because to what degree the consistency can be insured varies according to the site or portion to be measured. For example, a forehead portion is known to have even structure in the skull or the like. For this reason, β is set to 60 mm.

By contrast, the structure of the skull is complicated at portions near an ear in the temporal portion, and the consistency becomes low in the rectangular area (60 mm per side) whose vertices are the adjacent four detection modules DM. For this reason, the sparse value β is set to 30 mm at portions near an ear in the temporal portion. Moreover, the threshold γ is appropriately determined to be 0.7 at these portions. The relation between the sparse value and the threshold is determined based on the formula of the Fermi function. The constant is determined based on the Fermi function such that the constant becomes 0.9 when the sparse value β exceeds 60 mm and the constant becomes 0.7 when the sparse value β becomes less than 30 mm.

When a singular point is detected, the matrix value of such a singular point is corrected (see step S33). The matrix value is corrected by multiplying all the matrix elements of an object to be corrected by a coefficient such that the matrix (light quantity distribution) of the object to be corrected becomes the average of the other three matrices (light quantity distributions). After such a correction is performed, the measured values of the four detection modules DM are compared with each other again to determine whether any singular points are present.

Figure 35:
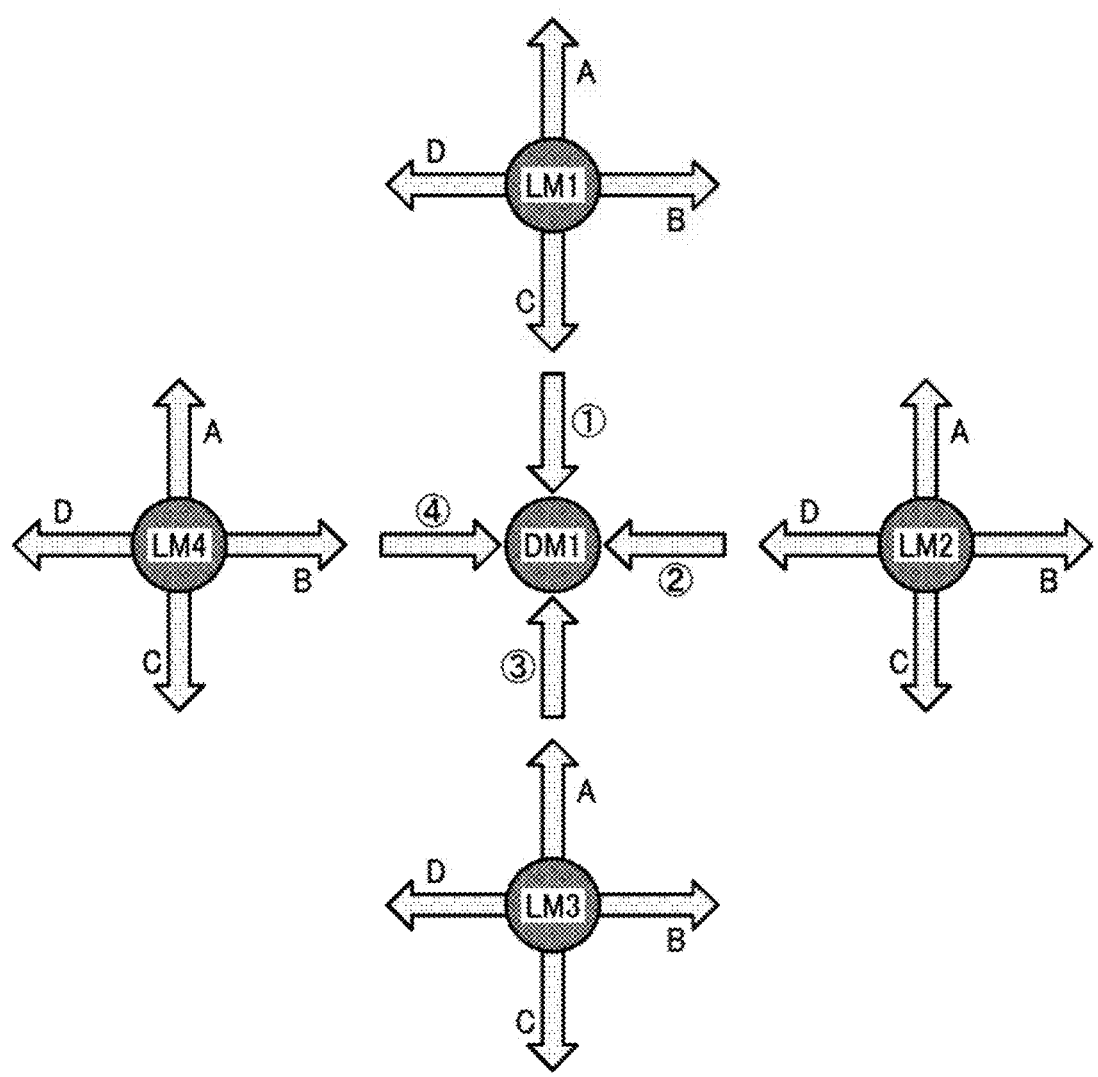
FIG. 35 is a diagram illustrating a method of detecting a singular point of a single light detection module DM in four directions and a method of removing such a singular point, according to the first embodiment of the present invention.

Next, similar processes are performed with four light source modules LM surrounding one detection module DM at the center (see steps S34 to S36 in FIG. 34 and FIG. 35). This method is similar to the method described as above, and thus its detailed description is omitted.

Figure 36:
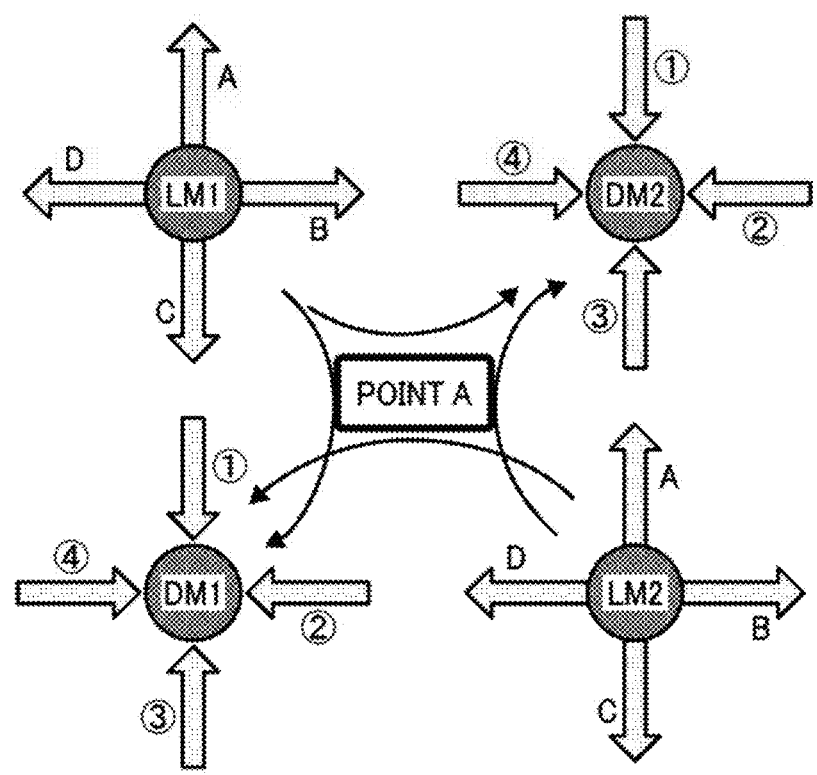
FIG. 36 is a diagram illustrating a method of comparing amounts of the detection light with each other in Point A of the rectangle whose vertices are two light source modules LM and two detection modules DM, and a method of correcting the amounts of the detection light, according to the first embodiment of the present invention.

After singular points are removed, the amounts of light of neighboring matrices are compared with each other, and correction is performed if necessary (steps S37 to S39). In the layout as illustrated in FIG. 36, the comparison in the area of the Point A is performed. The four arrows in FIG. 36 indicate the propagation paths of the light that are most susceptible to the situation of the area. These four propagation paths are strongly relevant to the amounts of light of ((2) of DM1, B of LM1), ((1) of DM1, A of LM2), ((3) of DM2, C of LM1), and ((4) of DM2, D of LM2) in the matrix. When the optical properties are equivalent to each other among propagation paths, the amounts of the light of the matrices are expected to match in the simulation.

However, in the actual system, the propagation paths are slightly different from each other, and an error E occurs. In the present embodiment, the distance of each of the propagation paths is equal to or less than 30 mm. However, the optical properties of an area to be measured may vary from the distance of 30 mm. For this reason, the comparison with the sparse value β is performed, and whether or not to perform correction is determined by determining to what degree the error a is to be accepted.

Then, correction is performed (step S39) in a similar manner to the step S33 as necessary, and one of the optical models is selected. As known in the art, optical models are influenced by three particular kinds of factor including the color of skin (thickness of skin), the thickness of the skull, and bone marrow fluid.

In order to deal with such a situation, optical models that include a skin layer, a skull layer, and a bone marrow fluid layer are prepared. The combinations of these optical models and pairs of probes (pairs of light source modules LM and detection modules DM) make nine detection patterns. Then, a model that is most suitable for the area of a certain pair of probes is selected from these nine detection patterns. In such selection, a matrix (similar to that of FIG. 7B) that is prepared by performing nine patterns of optical simulation is considered. One of the patterns is selected where an error becomes minimum between the values of the nine matrix elements of such a prepared matrix and the values of the corresponding nine matrix elements obtained by actual measurement on a test object. In order to achieve such selection, weighting is performed as follows.

The skin layer, skull layer, and the bone marrow fluid layer are arranged from the surface of a scalp to a deeper portion of a head. For this reason, weighting in the depth direction is performed (step S40). More specifically, when the pairs of optical paths ((1), A) and ((3), C) are considered in the matrix of FIG. 7, the light propagates in a relatively surface portion in the optical path ((1), A), and the light propagates in a relatively deeper portion in the optical path ((3), C). Accordingly, an influence is strong at a shallow portion in the optical path ((1), A), and the model of the color of skin at a shallow portion is weighted. In a similar manner, an influence is strong at a deep portion in the optical path ((3), C), and the model of bone marrow fluid at a deep portion is weighted. For example, the weighting factors are determined as follows.

In the selection of the optical model of a skin layer, the weighting factor is set to 2.0 for the matrix element ((1), A), and the weighting factor is set to 1.5 for the matrix element ((2), B). Moreover, the weighting factor is set to 1.0 for the other matrix elements. In the selection of the optical model of a skull layer, the weighting factor is set to 1.5 for the matrix element ((2), B), and the weighting factor is set to 1.0 for the other matrix elements. In the selection of the optical model of a bone marrow fluid layer, the weighting factor is set to 2.0 for the matrix element ((3), C), and the weighting factor is set to 1.0 for the other matrix elements.

After weighting is done as above, one of the optical models is selected for each of the matrix elements using the least-squares method (step S41).

It is to be noted that another sensor, in addition to the optical sensor, may be used in selecting one of the optical models. For example, an ultrasonic sensor that measures the bone density may be used, or the disturbance light may be detected and corrected. Alternatively, an acceleration sensor may be provided to remove artifacts.

Next, the sensitivity distribution of the selected optical model and the sensitivity distribution of the test object are used to perform inverse problem estimation. Assuming that the change $\delta\mu_a(r)$ in absorption coefficient caused by a light absorber is sufficiently small, the following equation holds true due to the approximation of Retov.

$$\log\frac{\phi_0(rs, rd)}{\phi(rs, rd)} = \frac{v}{S}\frac{\int d\vec{r}\phi_0(rs, r)\delta\mu_a(r)\phi_0(r, rd)}{\phi_0(rs, rd)} \quad \text{[Formula 2]}$$

v denotes the velocity of light in a medium, and S denotes the amount of light emitted from the light source module LM per unit time. rs denotes the position of the light source module LM, and rd denotes the position of the detection module DM. φ(rs, rd) indicates the amounts of the light that is received by the detection module DM after being emitted from the light source module LM, and φ0 indicates the light intensity on condition that a light absorber is absent. This formula indicates that when the light intensity φ0 is given in the absence of the light absorber, a linear correlation is established between the observed value log φ(rs, rd) and the change $\delta\mu_a(r)$ in the absorption coefficient caused by the light absorber.

This may be simplified in the equation as follows.

$$Y=A(r)X$$

In this equation, Y denotes the change in the observed value due to the presence or absence of the light absorber, and X denotes the change in the absorption coefficient at the position r of the voxel. Moreover, A(r) indicates the sensitivity distribution. The above equation indicates how the observed value Y changes due to the change in the position or amount of the light absorber indicated by X.

In an inverse problem estimation, calculation the other way around is performed. In other words, the position X of the light absorber is estimated using the observed value Y. As described above with respect to the position measuring method, measurement is performed upon assuming that the change due to the presence or absence of the light absorber is the difference Δr (i, n). This difference Δr (i, n) is used as the observed value Y to calculate X.

As known in the art, an estimation method for a reverse problem called L2 norm regularization is used for the above calculation. In this method, X that minimizes the cost function C as given below is calculated.

$$C=|Y-AX|^2++\lambda|X^2| \quad \text{[Formula 3]}$$

In the Formula 3, Y, A, and λ indicate the observed value, the sensitivity distribution, and the regularized coefficient, respectively. In the inverse problem estimation, the above method is commonly adopted. However, in the present embodiment, a Bayes estimation that can also detect the depth direction is used to perform an inverse problem estimation. For the detail of the inverse problem estimation using the Bayes estimation, see "T. Shimokawa, T. Kosaka, O. Yamashita, N. Hiroe, T. Amita, Y. Inoue, and M. Sato, "Hierarchical Bayesian estimation improves depth accuracy and spatial resolution of diffuse optical tomography, "Opt. Express*20*, 20427-20446 (2012)". Moreover, the results given below are disclosed in JP-2014-230745-A.

Figure 37A:
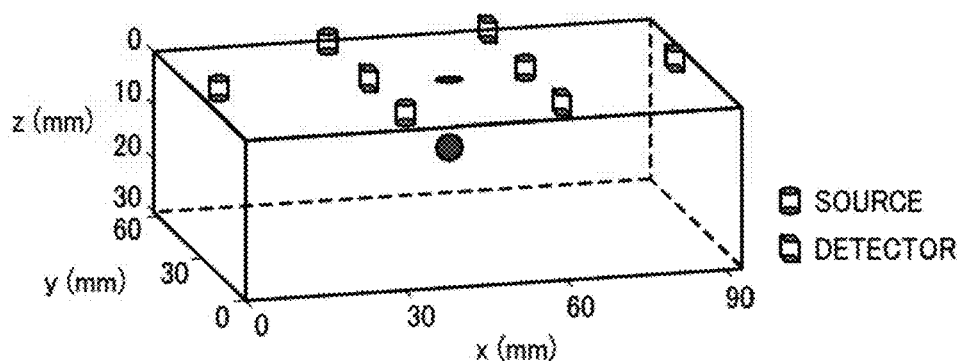
FIG. 37A illustrates the actual position of the light absorber according to the first embodiment of the present invention.
Figure 37B:
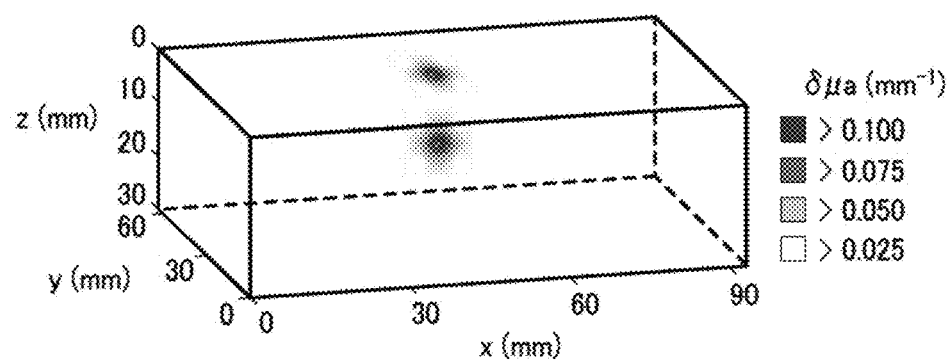
FIG. 37B illustrates the result of estimation of the position of the light absorber according to the first embodiment of the present invention.

As a result, the result of estimation as illustrated in FIG. 37B can be obtained. FIG. 37A illustrates the actual position of the light absorber according to the first embodiment. The grid in FIG. 37B has 3 mm patterns, and the actual position can be obtained with 3 mm precision.

Figure 37C:
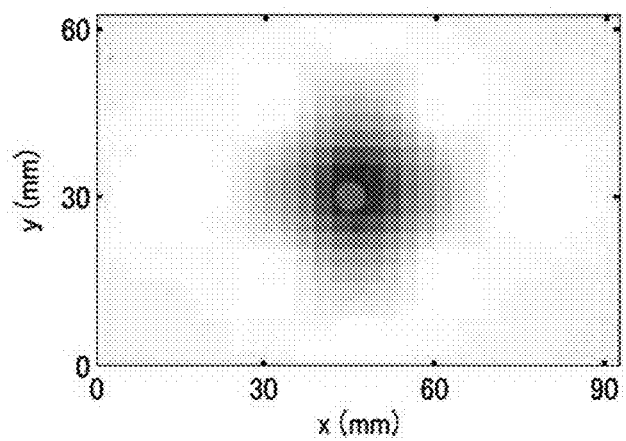
FIG. 37C illustrates the result of the detection of the position of a light absorber, according to a control sample.

As a control sample, the result of detection where one of the four orientations is used is illustrated in FIG. 37C. The configuration of this control sample is almost equivalent to that of the conventional NIRS DOT device. In the control sample, it is not possible to detect the depth direction, and the detection result becomes very much dispersed. By contrast, in the first example of the present embodiment, the Bayes estimation is adopted as described above, and both the position and depth of the light absorber are detectable.

Figure 38A:
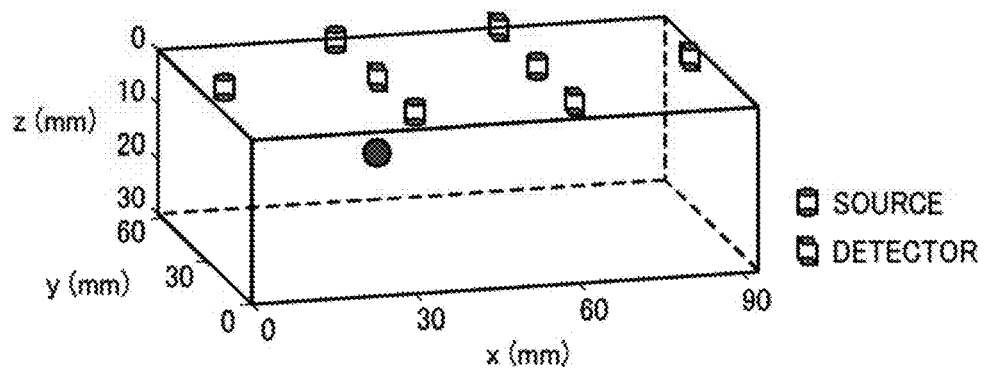
FIG. 38A illustrates the actual position of a light absorber after movement, according to the first embodiment of the present invention.
Figure 38B:
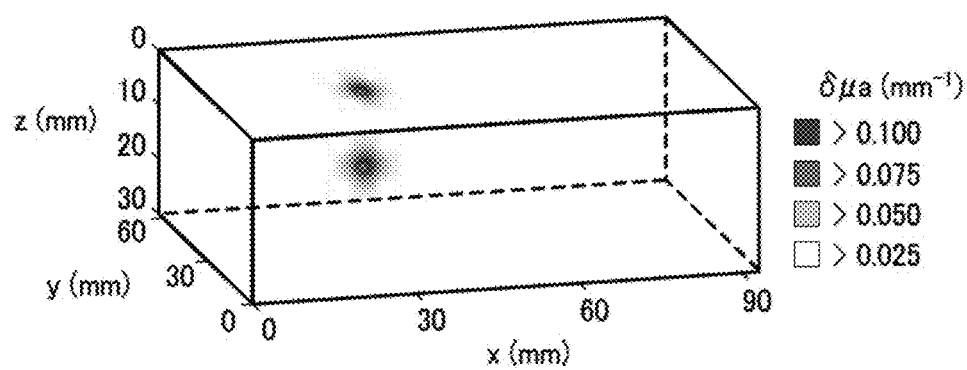
FIG. 38B illustrates the result of estimation of the position of a light absorber after movement, according to the first embodiment of the present invention.
Figure 38C:
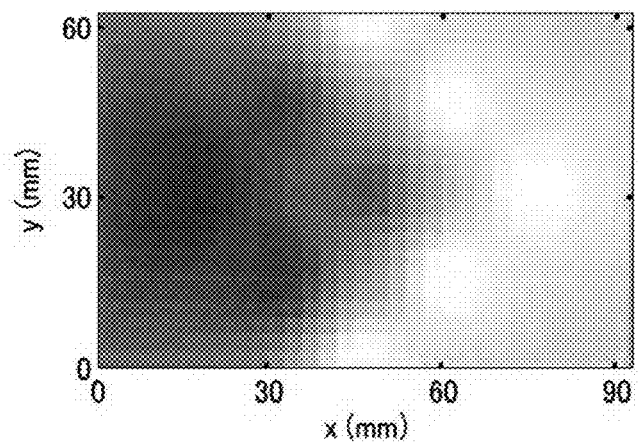
FIG. 38C illustrates the result of the detection of the position of a light absorber, according to a control sample.

The position of the light absorber is changed as illustrated in FIG. 38A, and the estimation of the position is performed as illustrated in FIG. 38B. Even after the light absorber is moved, the actual position of the light absorber is precisely estimated. As the method in the first example is adopted, the position of the light absorber is detectable with high resolution. By contrast, in the control sample, the image of the light absorber is very much dispersed as illustrated in FIG. 38C, and it is not possible to detect the position of the light absorber with accuracy.

Next, a second example of the present embodiment is described below. Note that the second example will be described in relation to the first example as necessary.

Second Example

Firstly, black ink is dripped into the intralipid aqueous solution filling the acrylic transparent watertank to the degree of about 200 ppm, where the intralipid aqueous solution is obtained by diluting 10 percent intralipid ten times thinner. Accordingly, the absorption coefficient and scattering coefficient that are almost equivalent to those of a living body can be achieved. Then, a black light absorber simulating bloodstream is sunk into the whitish intralipid aqueous solution. In the present example, the light absorber is, for example, black polyacetal, and has an approximately 5 mm spherical body in diameter. In order to control the position of such a spherical body, the spherical body is attached to a thin 1 mm metallic rod in diameter, and the rod is connected to an automatic positioning stage. A probe is precisely aligned to a side of the watertank, and is attached thereto. In the present example, the acrylic watertank has a rectangular-parallelepiped shape with the volume of, for example, 140 mm×140 mm×600 mm, where thickness of the wall is 1 mm.

The optical sensor 10 includes an irradiation system including a plurality of (for example, eight) light source modules LM, and a detection system including a plurality of (for example, eight) detection modules DM. Each of the light source modules LM and the detection modules DM is connected to the controller 1001 through the electrical wiring.

The controller 1001 controls the timing of light emission at the light sources of the light source modules LM or the timing of detection at the detection modules DM, and transfers the obtained detection results to the storage unit. Moreover, the controller 1001 reads the data stored in the storage unit and perform calculation using the values of the read data, and controls the display unit 1003 to display the calculation result thereon.

Figure 39:
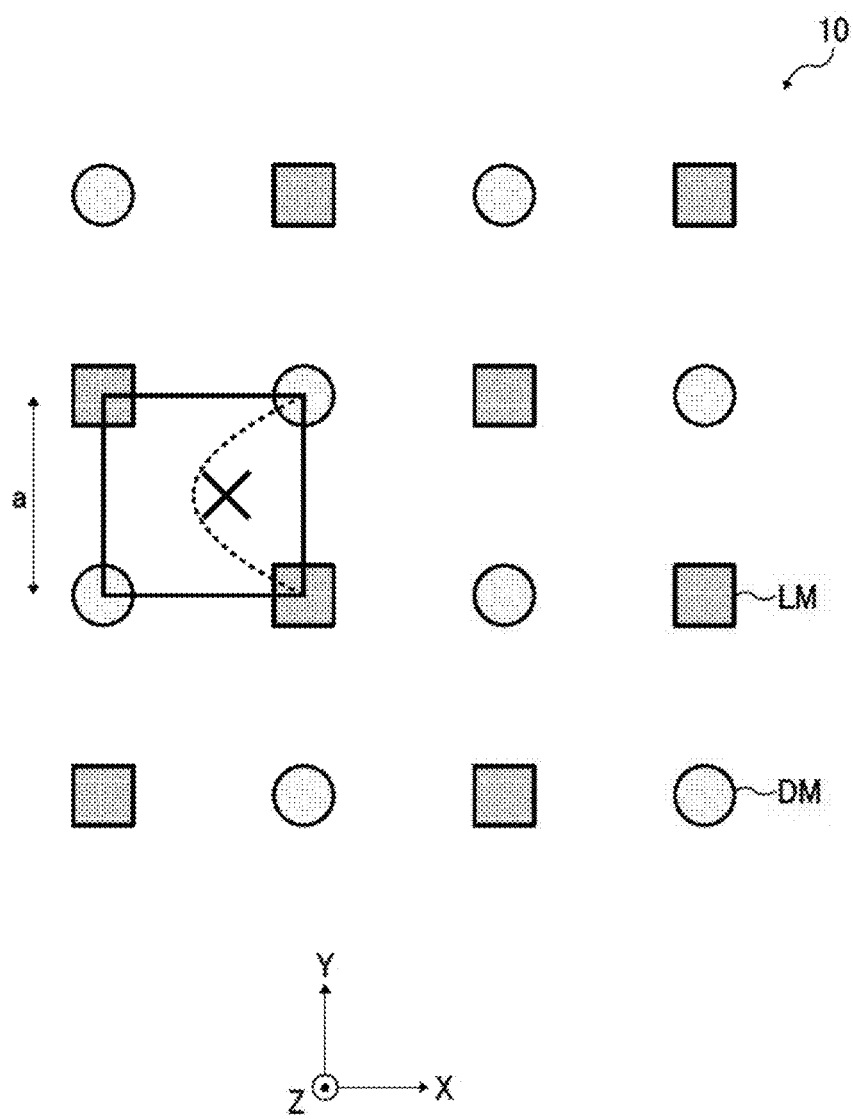
FIG. 39 is a diagram illustrating the arrangement of a plurality of light source modules and a plurality of detection modules in an optical sensor according to a second example of the present invention.

As illustrated in FIG. 39 for example, the eight light source modules LM and the eight detection modules DM are arranged for a pseudo living body in a four-by-four matrix (two-dimensional grid pattern) in the X direction and the Y direction with equal pitches, such that the light source module M and the detection module DM are next to each other in both the X direction and the Y direction that are orthogonal to each other. In FIG. 39, the rectangular signs denote the light source modules LM, and the circular signs denote the detection modules DM.

Figure 40:
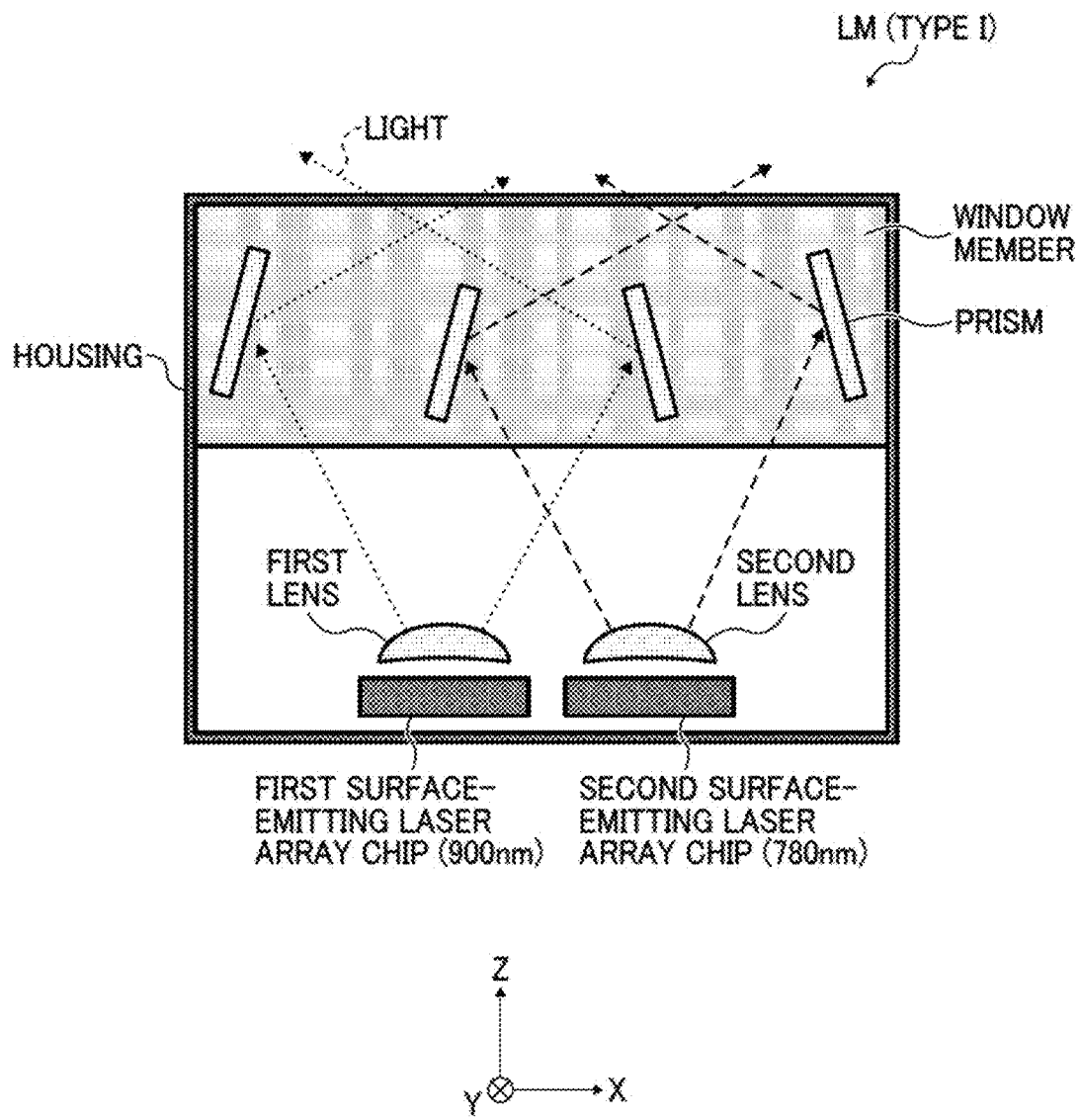
FIG. 40 is a diagram illustrating a light source module LM (type I) according to the second example of the present invention.

As illustrated in FIG. 40, the light source module LM (I type) according to the second example includes, for example, an optical element such as a lens and a prism, a ceramic package on which a plurality of surface-emitting laser array chip are mounted, a flexible circuit board on which the ceramic package and an analog electronic circuit are mounted, a wiring connected to the flexible circuit board, a connector, a housing accommodating these elements, a window member consisting of transparent resin that contacts the test object.

The light rays emitted from the surface-emitting laser array chips are refracted by the corresponding lenses, and deflected to a desired angle (reflected to a prescribed direction) by the prisms that are formed inside the window member and exited to the outside of the housing. In the present example, the prism serves as a reflection member.

Figure 41:
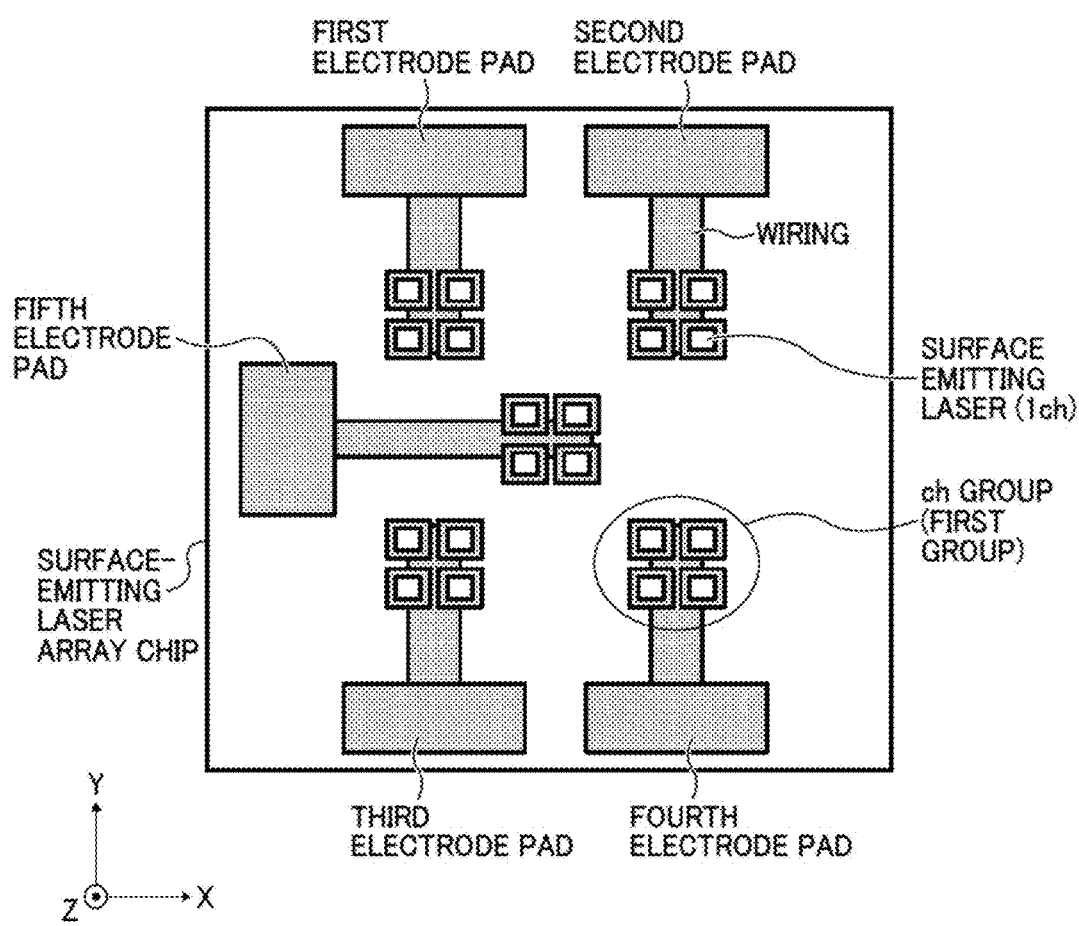
FIG. 41 is a diagram illustrating a surface-emitting laser array chip of the light source module LM (type I) according to the second example of the present invention.

As illustrated in FIG. 41, the surface-emitting laser array chip has a square shape with the sides of about 1 mm, and includes a plurality of (for example, twenty) two-dimensionally disposed surface emitting lasers.

More specifically, each of the surface-emitting laser array chips includes five groups (channel (ch) groups) each of which includes four surface emitting lasers. In the present example, the centers of the four groups among the five groups are disposed separately at the four vertices of the square, and the center of the remaining one group is disposed at the center of the square.

As described above, the four channels of each group are mounted on the ceramic package, and are connected to the same electrode pad (i.e., one of the first to fourth electrode pads) through the bonding wire (wiring).

The ceramic package is implemented by being soldered onto the wiring pattern of the flexible circuit board. On the flexible circuit board, a semiconductor for switching or a semiconductor for stabilizing the current are attached. The semiconductor for switching determines which channel of the surface-emitting laser array chip is to emit light. The semiconductor for switching controls the selected channel to emit light according to the externally given serial signal. One end of the signal line for the serial signal and one end of the power supply line are connected to the flexible circuit board, and the other end of the signal line and the other end of the power supply line are connected to the controller 1001.

The amount of light emission of each channel is calibrated constant at regular intervals. Under normal conditions, the five groups are controlled to emit light in sequence with short pulses. As the temperature rise due to heat liberation can be avoided, such pulse light emission is suitable for stabilizing the amount of light emission. The detection values obtained every time light is emitted with short pulses by the detection module are added up and then averaged. By so doing, the detection becomes resistant to the noise.

The oscillation wavelength of the surface emitting lasers (VCSEL) of the surface-emitting laser array chip is, for example, 780 nanometer (nm) or 900 nm. By using a plurality of surface emitting lasers with different oscillation wavelengths, a plurality of exiting lights with different wavelengths can be obtained. Further, a plurality of light rays with different wavelengths are emitted to an approximately same point of a test object (for example, a living body). By so doing, for example, the state of hemoglobin (i.e., a deoxidized state or an oxidized state) can be recognized. These wavelengths are selected in view of the fact that the absorption coefficient varies widely according to the oxygen concentration in the blood.

Figure 42A:
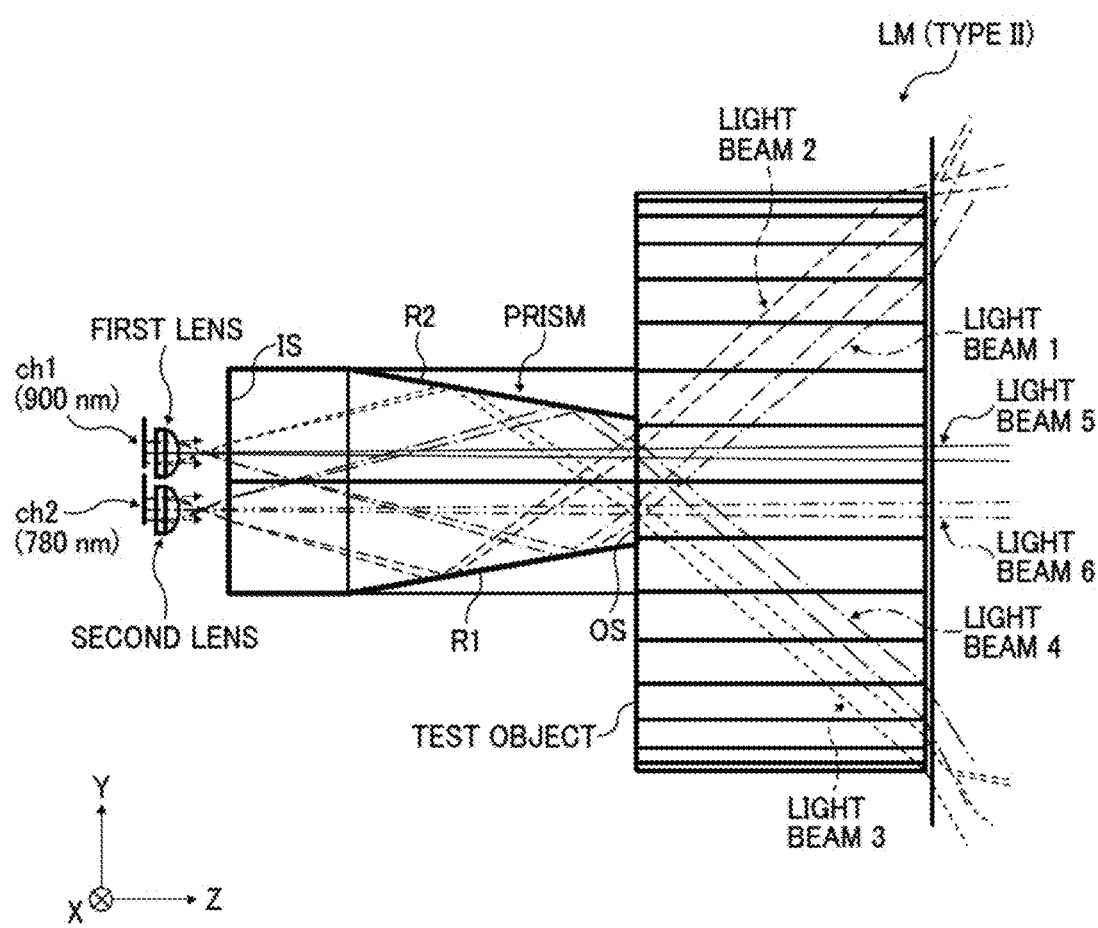
FIG. 42A and FIG. 42B are diagrams each illustrating a light source module LM (type II) according to the second example of the present invention.
Figure 42B:
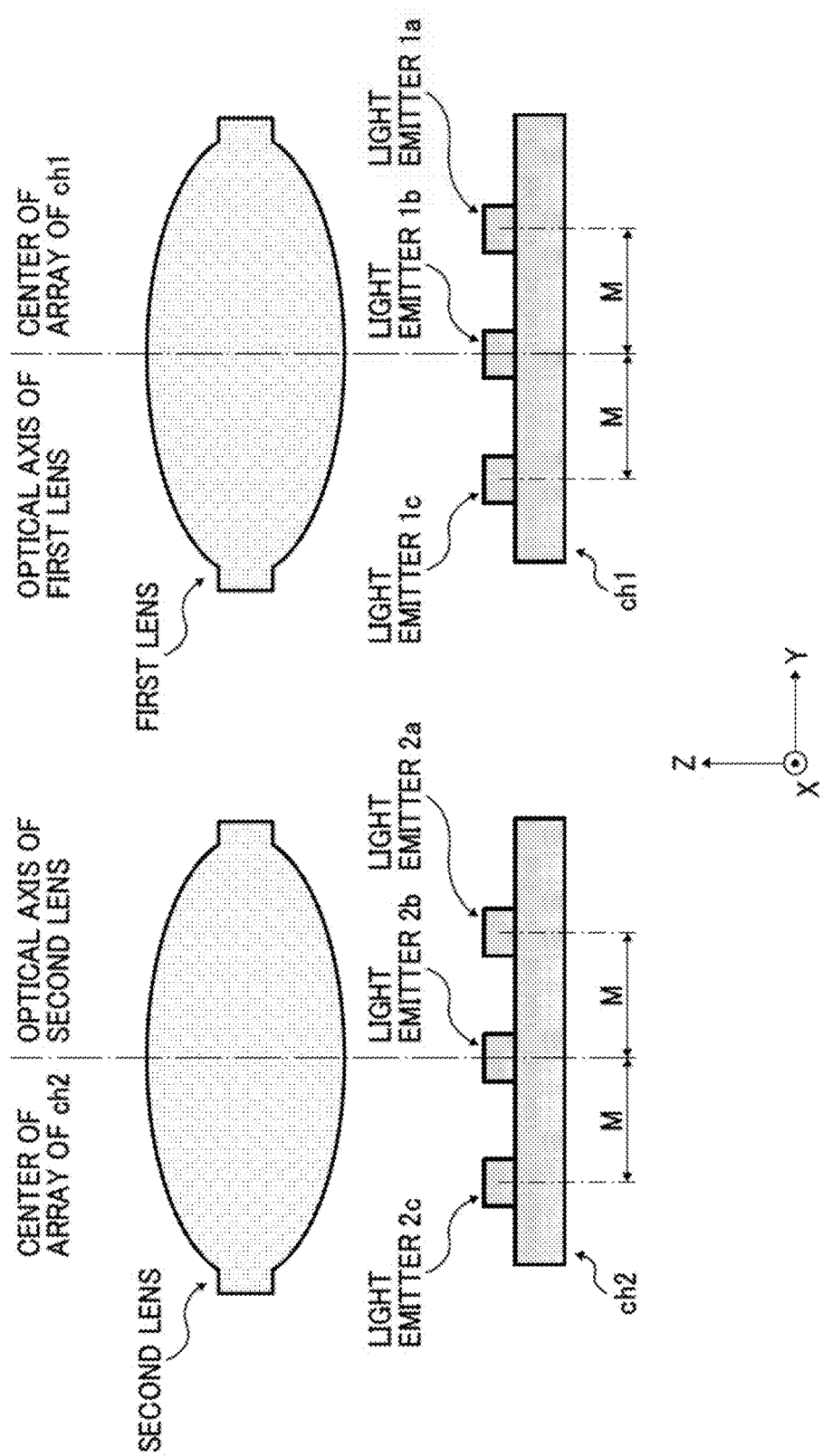

FIG. 42A and FIG. 42B are diagrams each illustrating a light source module LM (type II) according to the second example of the present invention. In the light source module LM (type II) according to the second example illustrated in FIG. 42A, a first surface-emitting laser array chip ch1 with the oscillation wavelength of 900 nm and a second surface-emitting laser array chip ch2 with the oscillation wavelength of 780 nm are arranged in parallel with each other. Moreover, a first lens (separate optical element) is disposed in the proximity of the exit end of the first surface-emitting laser array chip ch1, and a second lens (separate optical element)

is disposed in the proximity of the exit end of the second surface-emitting laser array chip ch2. Further, a prism (common optical element) for common use is disposed in the optical paths of the two light rays with different wavelengths that have passed through the first and second lenses. The surface-emitting laser array chips ch1 and ch2 are aligned in the Y direction on the XY plane such that the exit directions are in the Z-axis direction, and the surface-emitting laser array chip ch1 and ch2 have substantially the same configuration (including the number of light-emitting units and their arrangement) just except that the oscillation wavelengths are different from each other. In other words, the first and second lenses are substantially the same lens.

In the following description, the surface-emitting laser array chips 1 and the surface-emitting laser array chip 2 may be referred to as ch1 and ch2, respectively, and may be collectively referred to simply as channel (ch) when it is not necessary to distinguish these two channels.

In the light source module LM (type II), the relative positions of the multiple light-emitting units and the optical axis of the corresponding one of the lenses are equivalent to each other between two channels. More specifically, the center of each of the channels (center of array) is disposed on the optical axis of the corresponding one of the lenses.

Here, attention is focused on the three light-emitting units illustrated in FIG. 42B that are aligned at even intervals in the Y direction of each channel. These three light-emitting units that are aligned at even intervals M in the Y direction of ch1 are referred to as a light-emitting unit $1a$, light-emitting unit $1b$, and a light-emitting unit $1c$ in the order from +Y side to −Y side. In a similar manner, the three light-emitting units that are aligned at even intervals M in the Y direction of ch2 are referred to as a light-emitting unit $2a$, light-emitting unit $2b$, and a light-emitting unit $2c$ in the order from +Y side to −Y side. It is assumed that the light-emitting unit $1b$ and the light-emitting unit $2b$ are disposed on the optical axis of the corresponding one of the first and second lenses.

As illustrated in FIG. 42A, the prism has a symmetrical shape about the central axis (axisymmetric shape), and includes an incident plane IS that is orthogonal to the central axis, total reflection planes R1 and R2 that are oblique with reference to the central axis, and an exit plane OS that is orthogonal to the central axis.

The incident plane IS is disposed to involve the optical paths of the light rays that are emitted from the three light-emitting units $1a$, $1b$, and $1c$ of ch1 and to involve the optical paths of the light rays that are emitted from the three light-emitting units $2a$, $2b$, and $2c$ of ch2.

The total reflection plane R1 is disposed to involve the optical path of the light (light beam 1) that is emitted from the light-emitting unit $1a$ and has passed through the first lens and the incident plane IS, and the optical path of the light (light beam 2) that is emitted from the light-emitting unit $2a$ and has passed through the second lens and the incident plane IS. The incident angles of the light beams 1 and 2 on the total reflection plane R1 is equal to or greater than a critical angle.

The total reflection plane R2 is disposed to involve the optical path of the light (light beam 3) that is emitted from the light-emitting unit $1c$ and has passed through the first lens and the incident plane IS, and the optical path of the light (light beam 4) that is emitted from the light-emitting unit $2c$ of ch2 and has passed through the second lens and the incident plane IS. The incident angles of the light beams 3 and 4 on the total reflection plane R2 is equal to or greater than a critical angle.

The exit plane OS is disposed to involve the optical paths of the light rays (light beams 1 and 2) reflected on the total reflection plane R1, the light rays (light beams 3 and 4) reflected on the total reflection plane R2, the light (light beam 5) that is emitted from the light-emitting unit $1b$ of ch1 and has passed through the first lens and the incident plane IS (traveling in a straight line), and the light (light beam 6) that is emitted from the light-emitting unit $2b$ of ch2 and has passed through the second lens and the incident plane IS (traveling in a straight line), and the light beams 1 to 5 exit through (pass through) the exit plane OS. In the present embodiment, the exit plane OS serves as a contact surface that contacts the surface of a test object. For this reason, it is desired that transparent gel be provided between the exit plane OS and the surface of the test object.

In such a configuration, the two light rays with different wavelengths that are emitted from the two light-emitting units $1a$ and $2a$ in an approximately parallel state and have entered the first and second lenses are refracted by the first and second lenses, and enter the incident plane IS in an approximately parallel state. Then, these two light rays are refracted by the incident plane IS, and enter the total reflection plane R1 in an approximately parallel state. The two light rays with different wavelengths that are reflected by the total reflection plane R1 enter an approximately same point of the test object in an approximately parallel state. In such a configuration, the positions at which the two light rays with different wavelengths enter the test object are apart from each other to some extent (by about the space between the light-emitting unit $1a$ and the light-emitting unit $2a$).

In a similar manner, the two light rays with different wavelengths that are emitted from the two light-emitting units $1c$ and $2c$ in an approximately parallel state and have entered the first and second lenses are refracted by the first and second lenses, and enter the incident plane IS in an approximately parallel state. Then, these two light rays are refracted by the incident plane IS, and enter the total reflection plane R2 in an approximately parallel state. The two light rays with different wavelengths that are reflected by the total reflection plane R2 enter an approximately same point of the test object in an approximately parallel state. In such a configuration, the positions at which the two light rays with different wavelengths enter the test object are apart from each other to some extent (by about the space between the light-emitting unit $1c$ and the light-emitting unit $2c$).

In order to further improve the accuracy of the detection, it is desired that the positions at which the two light rays with different wavelengths enter the test object be the same (or made closer to each other as much as possible). In order to achieve this, it is considered to be effective to bring the optical paths of these two light rays with different wavelengths that are reflected by the total reflection plane of the prism to approximately match.

Accordingly, two reflection planes may separately be disposed on the optical paths of the two light rays from two channels with different wavelengths (see FIG. 40). However, it is difficult to bring the optical paths of these two light rays with different wavelengths to approximately match.

It may be possible to match the light exit directions of the two light rays with different wavelengths at the two lenses, but in particular, it is impossible to make the exit points of the two channels (i.e., the positions of the light-emitting units) same.

Figure 43:
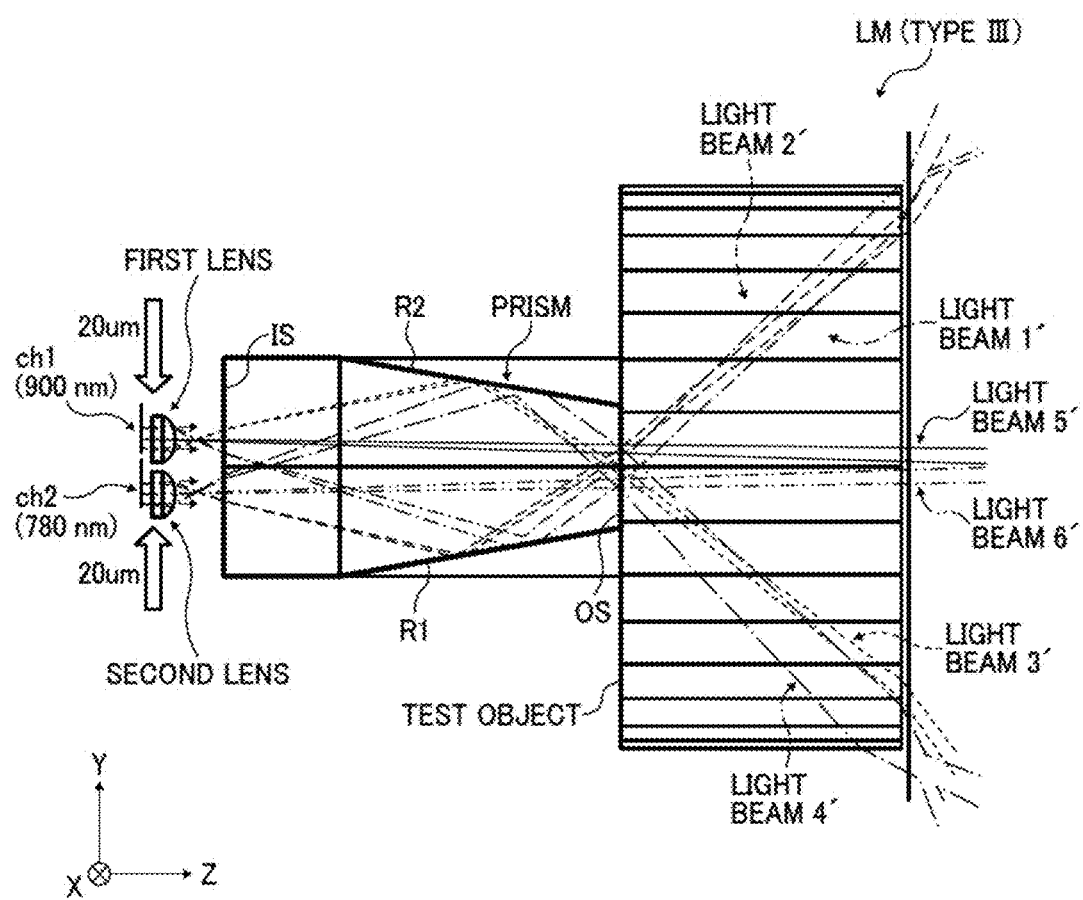
FIG. 43 is a diagram illustrating a light source module LM (type III) according to the second example of the present invention.

Next, a light source module LM (type III) according to the second example, as illustrated in FIG. 43, is described. In the light source module LM (type III), the relative positions of the multiple light-emitting units and the optical axis of the corresponding one of the lenses are different from each other between two channels. The light source module LM (type III) is different from the light source module LM (type II) illustrated in FIG. 42A only in this respect, and the light source module LM (type III) is equivalent to the light source module LM (type II) in the other respects.

In the light source module LM (type III), the space between the centers of the two channels (the space between the centers of the arrays) is about 1.4 mm. These relative positions of the two channels are made close to each other as much as possible in view of a pad portion or the like that is used when wire bonding is performed.

Note that each of the channels have 1 mm sides, and the two channels are placed with very close space (gap) of about several hundred micrometers (μm). In the present embodiment, such a close placement is achieved by modifying, for example, the collet of a die bonder device.

The light-emitting units (surface emitting lasers) of the two channels are manufactured by performing semiconductor processes with an identical mask, and the positions of the light-emitting units can be controlled with the precision of equal to or smaller than 0.5 μm.

In a similar manner to the light source module LM (type II), the surface-emitting laser array chip 1 (900 nm) and the surface-emitting laser array chip 2 (780 nm) of the light source module LM (type III) are manufactured with the same level of precision and has the same layout.

The two light rays with different wavelengths that are emitted from the two channels whose centers are about 1.4 mm apart and have passed through the corresponding lens, as described above, are reflected by the same total reflection plane of the prism, and enters the test object (for example, a living body).

In the configuration of the light source module LM (type II), the two light rays that are emitted from the associated ch1 and ch2 enter the test object (for example, a living body) at approximately equal distances (about 1.4 mm) maintaining a state where these light rays are parallel to each other. Accordingly, the gap between the two positions at which the light rays enter the test object is kept at about 1.4 mm. If the gap between these incident positions is large as described above, the resolution in the functional near-infrared spectroscopy (fNIRS), in which the cerebral blood flow is detected by performing inverse problem estimation, decreases.

In order to avoid such a situation, a method of bringing the optical paths of these two light rays with different wavelengths to approximately match to match the incident positions, without an increase in the cost of installation, was studied. As a result, a technique in which the center of each channel (the center of each array) is shifted by several micrometers (μm) to several hundreds of micrometers (μm) (preferably, several tens of micrometers (μm)) with reference to the optical axis of the corresponding one of the lenses was proposed, and this technique was provided for the light source module LM (type III).

Figure 44:
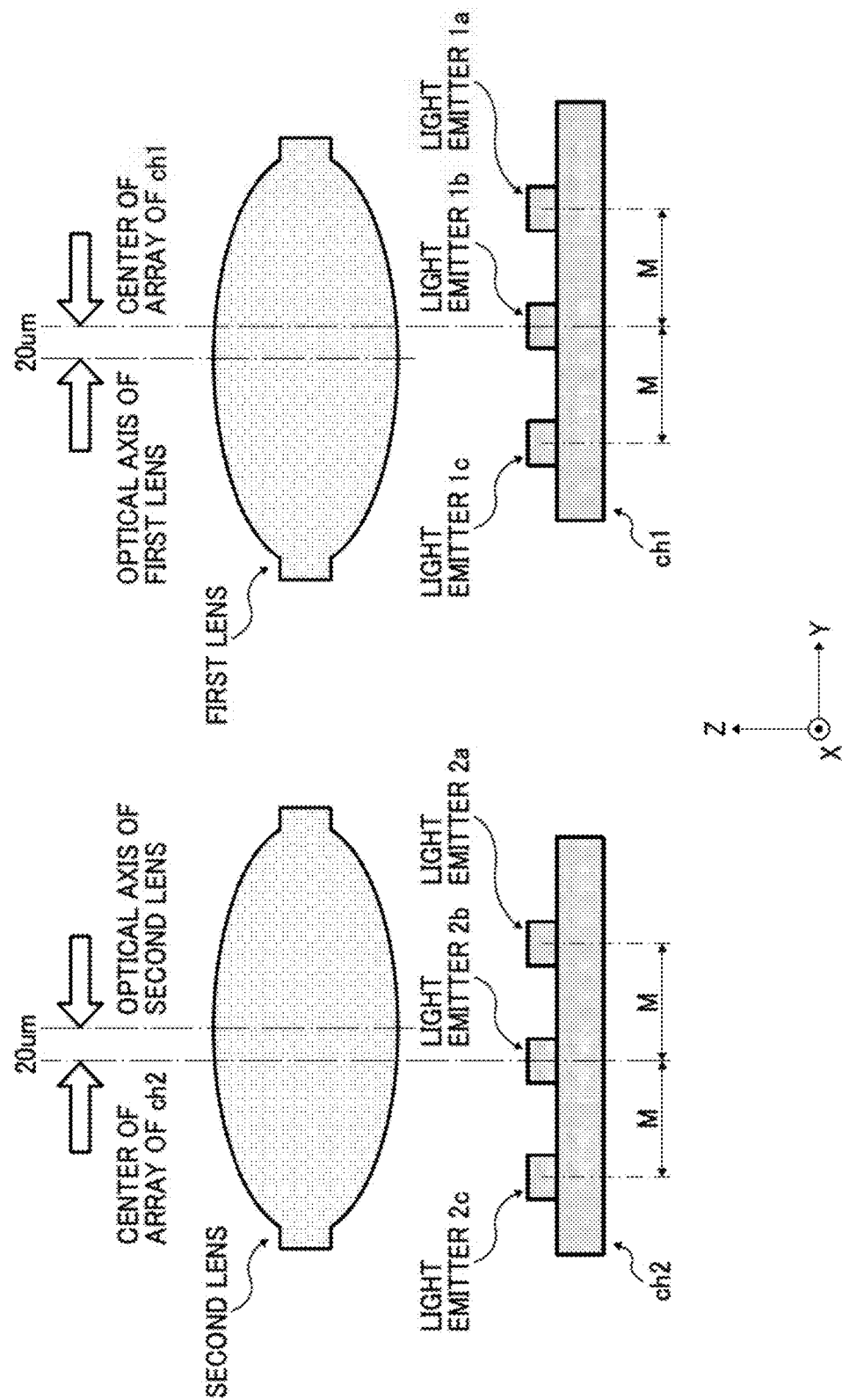
FIG. 44 is a diagram illustrating relative positions of a lens and a surface-emitting laser array chip in the light source module LM (type III) according to the second example of the present invention.

The details are described below with reference to FIG. 44. In the present embodiment, the center of each channel is displaced from the optical axis of the corresponding one of the lenses by about 20 μm. The degree of displacement is not limited to 20 μm, but may be varied as necessary.

In the present embodiment, the space between the centers of two channels (relative positions of two channels) is not changed, but the lenses that correspond to the respective channels are displaced. It is desired that the directions in which the lenses are to be shifted with reference to the corresponding channels be determined so as to be in axial symmetry (rotational symmetry) about the central axis of the prism that is an optical element in common (see FIG. 45).

Figure 45:
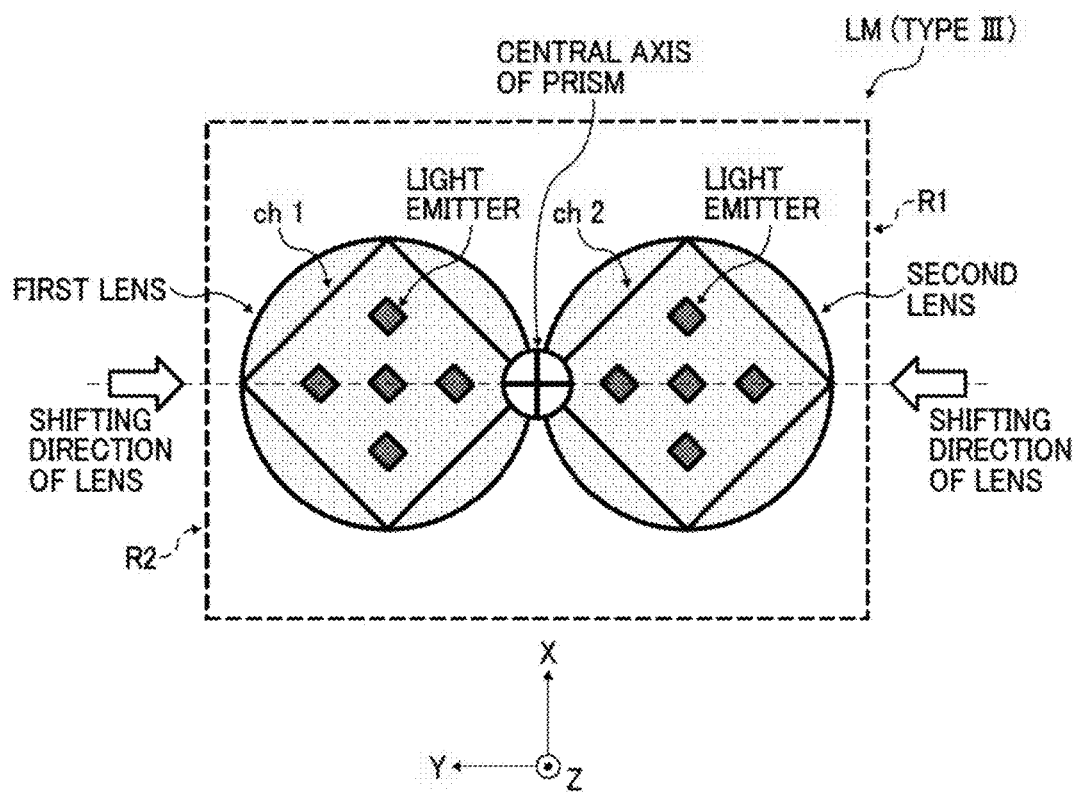
FIG. 45 is a diagram illustrating relative positions of a lens, a surface-emitting laser array chip, and a prism in the light source module LM (type III) according to the second example of the present invention.

In other words, the arrangement of the two channels and the first and second lenses are not limited to the arrangement illustrated in FIG. 45 as long as these elements are disposed in axial symmetry about the central axis of the prism (optical element in common).

In the present example, by way of example, the two channels are disposed across the central axis of the prism in the Y direction, such that the centers of the two channels are in axial symmetry (point symmetry) about the central axis of the prism. Each of the channels includes five light-emitting units (vertical-cavity surface-emitting lasers (VCSEL)), and these five light-emitting units are separately disposed at the center (center of the array) and the four vertices of the square in which one of the diagonal lines is parallel to the Y direction.

For example, the space between the centers of the two channels is 1.4 mm, and the pitch diameter of each lens is 0.8 mmφ. Moreover, the focal length f of each lens is, for example, 600 μm. In the present example, the directions in which the first and second lenses are shifted with reference to the two channels ch1 and ch2 are in the directions where the first and second lenses move closer to one another as illustrated in FIG. 45. In the present example, the first lens is displaced by about 20 μm in the −Y direction from a state in which the optical axis of the first lens passes through the center of ch1, and the second lens is displaced by about 20 μm in the +Y direction from a state in which the optical axis of the second lens passes through the center of ch2. As a result, the center of ch1 is displaced from the optical axis of the first lens by about 20 μm, and the center of ch2 is displaced from the optical axis of the second lens by about 20 μm.

In this configuration, the optical path of the light (light beam 1') that is emitted from the light-emitting unit 1a of ch and enters the total reflection plane R1 after passing through the first lens and the incident plane IS is not parallel to the optical path of the light (light beam 2') that is emitted from the light-emitting unit 2a of ch2 and enters the total reflection plane R1 after passing through the second lens and the incident plane IS, and these two optical paths get close to each other as they get close to the total reflection plane R1 (see FIG. 43). Assuming that the incident angles at which the two light rays enter the corresponding lenses are equal to each other, the angles of refraction of these light rays increase as the positions at which the light rays enter the lenses are distant from the optical axes.

In a similar manner, the optical path of the light (light beam 3') that is emitted from the light-emitting unit 1c of ch1 and enters the total reflection plane R2 after passing through the first lens and the incident plane IS is not parallel to the optical path of the light (light beam 4') that is emitted from the light-emitting unit 2c of ch2 and enters the total reflection plane R2 after passing through the second lens and the incident plane IS, and these two optical paths get close to each other as they get close to the total reflection plane R2 (see FIG. 43).

Moreover, the optical path of the light (light beam 5) that is emitted from the light-emitting unit 1b of ch1 and enters the exit plane OS after passing through the first lens and the incident plane IS gets close to the optical path of the light (light beam 6') that is emitted from the light-emitting unit 2b of ch2 and enters the exit plane OS after passing through the second lens and the incident plane IS, as these two optical paths get close to the exit plane OS (see FIG. 43).

The optical paths of the two light rays (light beams 1' and 2') with different wavelengths that are reflected by the total reflection plane R1 and not parallel to each other intersect near the exit plane OS that is a contact surface with a test object. Moreover, the optical paths of the two light rays (light beams 3' and 4') with different wavelengths that are reflected by the total reflection plane R2 and not parallel to each other intersect near the exit plane OS that is a contact surface with a test object (see FIG. 43).

Accordingly, as illustrated in FIG. 43, the optical paths of the two light rays (light beams 1' and 2') with different wavelengths that are reflected by the total reflection plane R1 approximately overlap one another, and the positions at which the two light rays enter the test object become the same. Moreover, the optical paths of the two light rays (light beams 3' and 4) with different wavelengths that are reflected by the total reflection plane R2 approximately overlap one another, and the positions at which the two light rays enter the test object become the same. Further, the position at which the two light rays (light beams 5' and 6') with different wavelengths, which heads for the exit plane OS without being reflected on either one of the total reflection planes, enters the test object are approximately the same.

The laser-beam bundle including the light beams 1' and 2', the laser-beam bundle including the light beams 3' and 4', and the laser-beam bundle including the light beams 5' and 6' are not parallel to each other, and each of the laser-beam bundles enters an approximately same point of the test object.

The light rays that are emitted from the two light-emitting units of ch1 other than the light-emitting units 1a, 1b, and 1c, as illustrated in FIG. 45, and the light rays that are emitted from the two light-emitting units of ch2 other than the light-emitting units 2a. 2b, and 2c pass through the incident plane IS, and are directly exited through the exit plane OS. As a result, these light rays enter an approximately same point of the test object in a similar manner to the laser-beam bundles as described above.

In the light source module LM (type III) described above, lenses are simply shifted (displaced) with reference to the corresponding channels to bring the optical paths of two light rays with different wavelengths to approximately match to match the incident position of these light rays. By matching the incident positions of the two light rays with different wavelengths, the position of the cerebral blood flow can be measured with high precision in a near-infrared spectroscopy (NIRS) device that performs an inverse problem estimation.

Alternatively, if a member such as a half mirror is used to achieve an advantageous effect as in the light source module LM (type III) instead of shifting lenses, it ends up with an increase in implementation cost as the number of optical components that require high-precision alignment increases.

In the light source module LM (type III), the optical axes of the first and second lenses are displaced (shifted) from the center points of the corresponding ch1 and ch2. However, no limitation is intended therein.

For example, only one of the optical axes of the first and second lenses may be displaced (shifted) from the center point of the corresponding channel, or the other optical axis may be disposed to pass through the center point of the corresponding channel.

Alternatively, a channel may be shifted with reference to the corresponding lens instead of or in addition to shifting a lens with reference to the corresponding channel.

Moreover, the directions in which the first and second lenses are shifted with reference to the corresponding ch1 and ch2 may be varied. For example, the first and second lenses may be shifted in the same direction, or the first and second lenses may be shifted in the opposite direction (i.e., the direction in which the first and second lenses get close to each other or away from each other).

The amounts of shifting (amount of displacement) of the first and second lenses with reference to the corresponding ch1 and ch2 may be equal to each other or different from each other.

In short, the relative positions of multiple light-emitting units and the optical axis of the corresponding one of the lenses are to be varied from each other between two channels, such that the optical paths of two light rays with different wavelengths that are emitted from ch1 and ch2 approximately match one another.

More specifically, it is desired that the relative positions of multiple light-emitting units and the optical axis of the corresponding one of the lenses are to be varied from each other between two channels such that the optical paths of two light rays with different wavelengths that are emitted from ch1 and ch2 and have passed through the first and second lenses gradually get close to each other and optical paths of these light rays intersect near the contact surface of the test object in the light source module LM (type III) (near the exit end in the light source module LM (type III)).

Next, the reason why the surface-emitting laser array chip is adopted as the light source of the optical sensor 10 is described. In the surface-emitting laser array chip, the multiple channels can be arranged two-dimensionally in close proximity to each other, and the light emission of the channels can be controlled in an in an independent manner. Further, the path of the exit light can be changed by disposing a small lens in the proximity of the channels.

For optical sensors provided for the DOT, precise control of the incident angle to the test object is required. As commonly-used light-emitting diodes (LED) have a wide angle of departure, a lens needs to have an aspherical surface in order to achieve collimated beam with high accuracy. Moreover, a commonly-used laser diode (LD) (end-surface emitting laser) has an asymmetrical angle of departure. For this reason, in order to achieve collimated beam with high accuracy, two lenses such as lenses with varying curvatures in length and breadth or cylindrical lenses need to be combined. Such a configuration is complicated, and advanced implementation is required.

By contrast, a surface emitting laser has an almost perfectly circular far field pattern, and only one spherical lens needs to be disposed to form a collimated beam. When the coherent light emitted from the LD is used, speckles occur in the test object (scatterer) and the scattered lights interfere with each other. Such a speckle pattern affects the measurement as a noise.

When the bloodstream inside the brain is observed, for example, by the DOT, a very large number of scatterings occur. For this reason, when the bloodstream inside the brain is observed, the measurement is not very much affected by a speckle pattern. However, the measurement is still affected by a return light where the light reflected by the surface of the skin directly returns to the light source. Such a return light may make the oscillation state inside the LD unstable, and in such a case, the stable operation is disabled. When coherent light is to be used in a stable manner, for example, in an optical disk, a wave plate or the like is used such that a specular reflection light does not become a return light. However, it is difficult to remove a return light of the reflection light from the scatterer.

In the case of a surface-emitting laser array chip, a plurality of light rays can simultaneously be emitted to a minute area, and the interference of the return light can be reduced (see, for example, JP-2012-127937-A).

Figure 46:
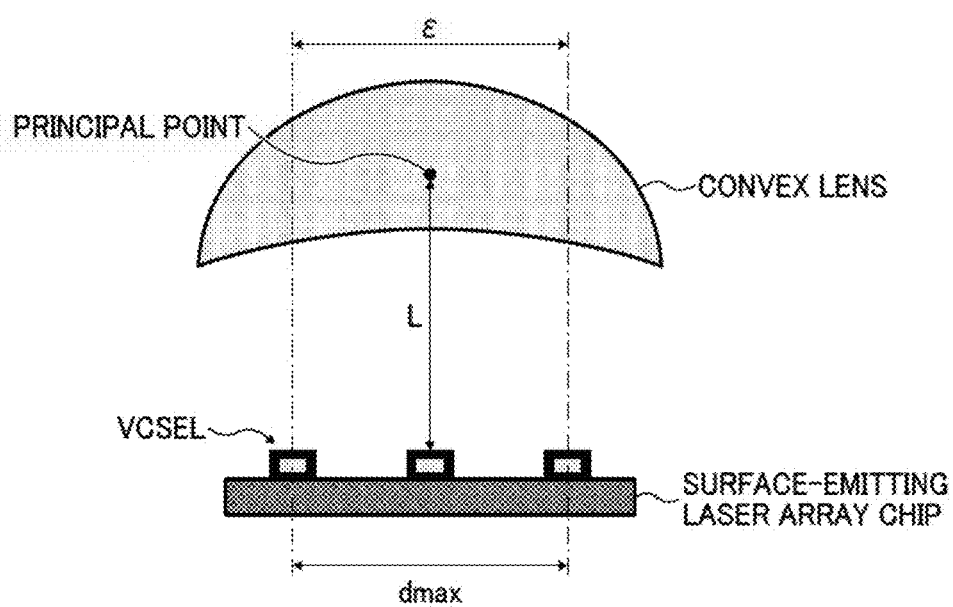
FIG. 46 illustrates a first additional configuration of the light source module according to the first and second examples of the first embodiment of the present invention.

In the present embodiment (the first and second examples), a convex lens is arranged on the optical path of the light emitted from the surface-emitting laser array chip (see FIG. 46). This convex lens may be referred to simply as a lens in the following description.

This convex lens has the 1 mm diameter, and has the 600 micrometer (μm) effective diameter ε. Moreover, the focal length f of the convex lens is 600 μm. The surface-emitting laser array chip is a chip with 1 mm angles, and the distance dmax between the centers of the two most distant channels in the surface-emitting laser array chip is 600 μm. As described above, by matching the dmax and the effective diameter ε, the diameter of the convex lens can be minimized.

In the present embodiment, the convex lens and the surface-emitting laser array chip are registered such that the distance L between the principal point (optical center) of the convex lens and the light-emitting surface (exit plane) of the surface-emitting laser array chip in the optical-axis direction of the convex lens becomes, for example, 300 μm. That is, f≠L.

In this configuration, a phenomenon (return light phenomenon) can be avoided in which the light emitted from the surface-emitting laser array chip and passed through the convex lens is reflected by a prism or the like by specular reflection and then is concentrated onto the surface-emitting laser array chip. As described above, a return light does not occur. Accordingly, the amount of light emission of each channel of the surface-emitting laser array chip can be stabilized.

When it is not necessary to consider the effect of a return light (i.e., when a higher resolution is not required for the NIRS), it is satisfactory even if f=L.

Figure 47:
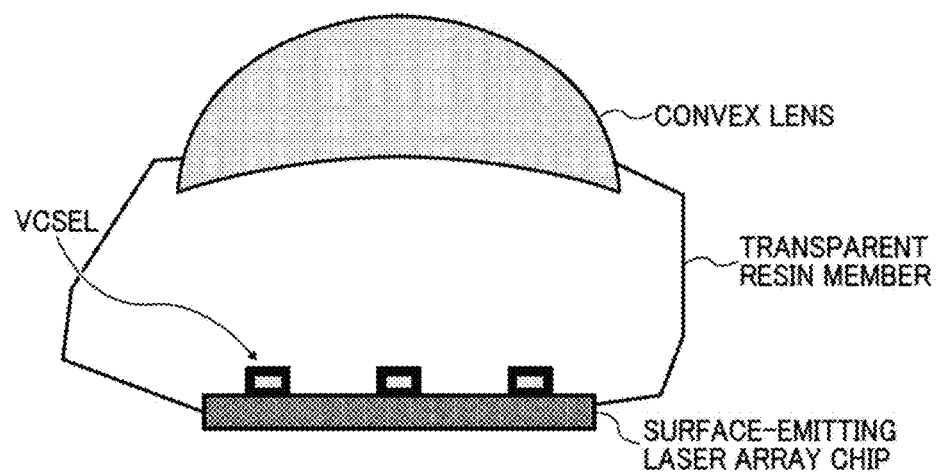
FIG. 47 illustrates a second additional configuration of the light source module according to the first and second examples of the first embodiment of the present invention.

As illustrated in FIG. 47, the space between the convex lens and the surface-emitting laser array chip is filled with a transparent resin so as not to include any airspace. In the present embodiment, the transparent resin is a resin having the refractive index equivalent to that of the convex lens (for example, a thermosetting epoxy resin). Accordingly, the refractive index does not change at the boundary of the interface between the convex lens and the surface-emitting laser array chip. The transparent resin may be formed by a metal mold before the convex lens is attached, or may be implanted after the convex lens is attached.

As the space between the convex lens and the surface-emitting laser array chip is filled with the transparent resin as described above, the reflection of the light emitted from the surface-emitting laser array chip on the surface of convex lens on the surface-emitting laser array chip side, i.e., the occurrence of the return light, can be prevented. As the occurrence of the return light is prevented, the amount of light emission of the channels can be stabilized. As the amount of the light of the channels is stabilized, the signal-to-noise ratio (S/N) of the measurement system improves, and the high-precision NIRS measurement and high resolution can be achieved.

Figure 48:
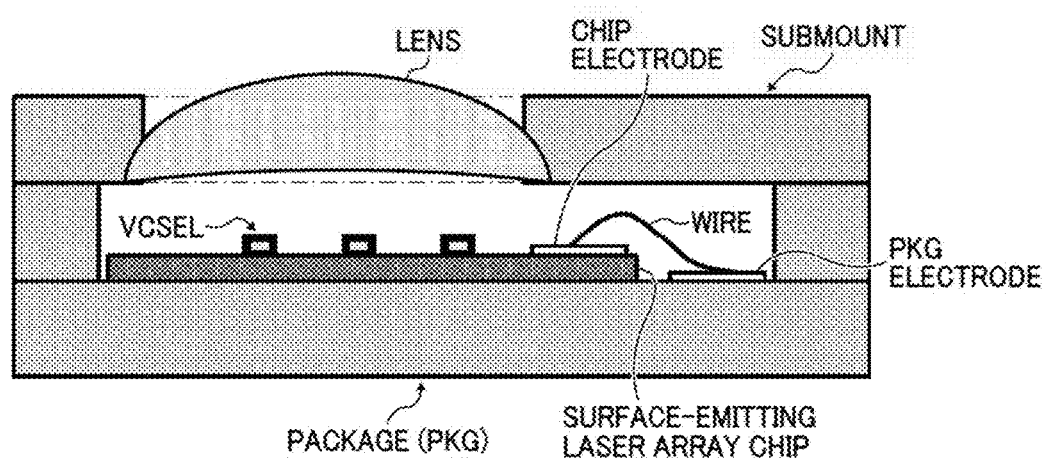
FIG. 48 illustrates a third additional configuration of the light source module according to the first and second examples of the first embodiment of the present invention.

As illustrated in FIG. 48, the surface-emitting laser array chip is mounted on the package, and the convex lens is attached to the package via the submount. In the surface-emitting laser array chip, the electrodes (chip electrodes) on the chip are electrically connected to the package (PKG) electrode on the package through a wire. The wire has a height of about several tens of micrometers, and is designed so as not to interfere with the submount. The attached position L of the convex lens (i.e., the distance between the light-emitting surface of the surface-emitting laser array chip and the principal point of the convex lens) is subject to constraints of the height of the wire. More specifically, when a wire is used in the above configuration, the wire may need to avoid the submount in the structure, or the height of the wire may need to be equal to or less than 100 μm. In other words, it is desired that −100 μm<f−L<0. Note that the illustration of the transparent resin illustrated in FIG. 47 is omitted in FIG. 48.

The light emitted from the exit plane of the surface emitting laser is approximately circular, and the divergence angle is about 5 degrees in half value width. As the laser beams of the LD known in the art is elliptic, the installation error in the rotation direction needs to be taken into consideration. However, in the surface emitting laser, such an installation error does not need to be taken into consideration. Moreover, as the light emitted from the exit plane of the surface emitting laser is approximately circular, it is easier to perform approximation or the like utilizing the symmetry of the circular shape when an optical simulation is performed to solve a reverse problem.

The laser beam emitted from the surface emitting laser is refracted by the convex lens disposed nearby. The refraction angle is determined by the relative positions of the surface emitting laser and the center of the lens (i.e., the optical axis of the lens). Accordingly, a desired refraction angle can be obtained by appropriately arranging the position of the lens and the position of the surface-emitting laser array chip of each group.

In the second example, the relative positions of the channel and the optical axis of the convex lens are determined such that the refraction angle becomes about 20 degrees. In the surface-emitting laser array chip, the light emission of the channels can be controlled in an in an independent manner. Accordingly, the direction of the light that is emitted from the light source modules LM can be changed by selecting the channel that is to emit the light.

Figure 49:
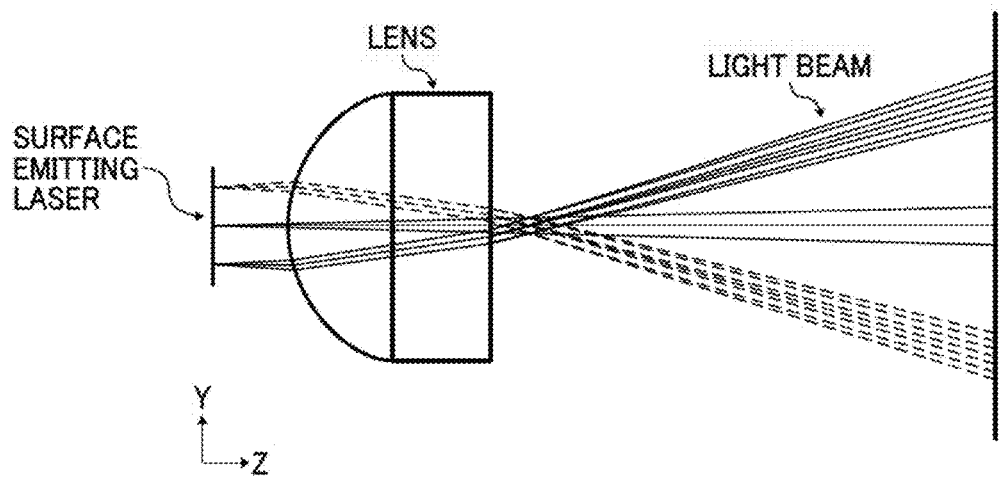
FIG. 49 illustrates an example of the light beams that are optically designed by an optical simulator, according to the first embodiment of the present invention.

FIG. 49 illustrates an example of the light beams that are optically designed by an optical simulator, according to the present embodiment. In FIG. 49, three channels (light sources) that simulate a surface-emitting laser array chip are provided, and a 1 mm lens in diameter with f=600 micrometer (μm) is disposed in the proximity of these three channels. One of the three channels is disposed on the optical axis of the lens, and the other two channels are separately disposed on two sides of the optical axis of the lens. The light rays emitted from the other two channels that are not on the optical axis are refracted by the lens, and the propagation direction (path) is bent. More specifically, the light rays emitted from the other two channels that are not on the optical axis are exited with the angle of about 20 degrees with reference to the optical axis of the lens, and the these two light rays are exited in opposite directions with reference to the optical axis.

In the present embodiment, the light source module LM is designed such that the incident angle at which the light enters the test object becomes about 55 degrees. More specifically, as illustrated in FIG. 40, in the light source module LM, the multiple light rays exiting from the convex lens in the direction with the oblique angle of about 20 degrees with reference to the optical axis are separately deflected by multiple prisms. Accordingly, the angles of the multiple light rays with reference to the optical axes of the corresponding lenses are changed from about 20 degrees to about 55 degrees, and the incident angle at which the light rays enter the surface of the test object becomes about 55 degrees.

Figure 50:
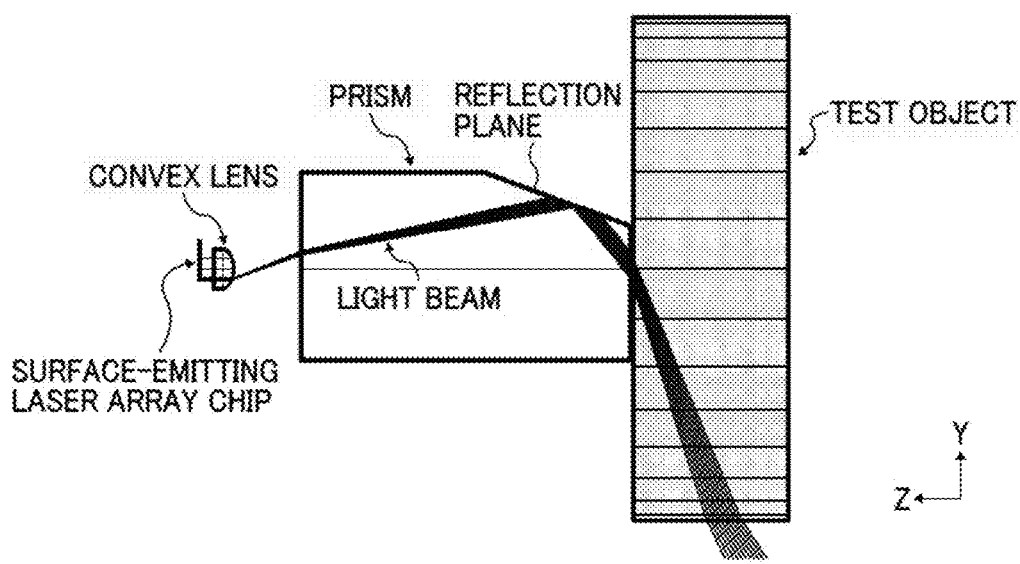
FIG. 50 illustrates an example of the result of the optical simulation according to the first embodiment of the present invention.

Note that the prism may be made of any material as long as it can reflect light. For example, the prism may be made of a glass substrate on which a metal film is formed. Alternatively, for example, a prism in which total internal reflection caused by a difference in refractive index is utilized may be adopted. FIG. 50 illustrates an example of the result of the optical simulation according to the first embodiment. The light beam emitted from the VCSEL is refracted by the convex lens, and then enters the prism.

In the present embodiment, the material of the prism is BK7. However, the prism may be made of any known optical material. The light that has entered the prism is reflected by the side (reflection plane) of the prism by total internal reflection, and enters the test object at an incident angle of about 55 degrees. In other words, the light that has passed through the convex lens is deflected by the prism in such a manner that the incident angle at which the light enters the test object becomes about 55 degrees. In this configuration, a transparent gel intervenes between the prism and the test object so as to prevent the dispersion of the light on the interface between the prism and the test object. The light rays emitted from the surface-emitting laser array chips becomes a plurality of light rays that are not parallel to each other after passing through the convex lens, and these light rays are reflected by the prisms and enter the test object. As a result, a plurality of approximately collimating light rays that are not parallel to each other enters the same point of the test object (see FIG. 50).

By the Snell law (the law of reflection), the propagation angle of the light beam in the test object changes from about 55 degrees to about 60 degrees due to the difference in refractive index between the prism and the test object.

In the optical system for which the convex lens and the prism are provided, the positions of the channels of the surface-emitting laser array chip are different from each other. Accordingly, the propagation angles of the light rays in the test object are adjustable. In the present embodiment, the centers of the channels (VCSEL) are displaced from the optical axis of the convex lens by about 200 μm. Accordingly, the propagation angles of the light rays emitted from the channels in the test object can be adjusted to about 60 degrees. As a result, the multiple light rays emitted from the multiple channels exit from a plurality of different positions on the exit plane of the convex lens as a plurality of approximately collimating light rays that are not parallel to each other.

Figure 51:
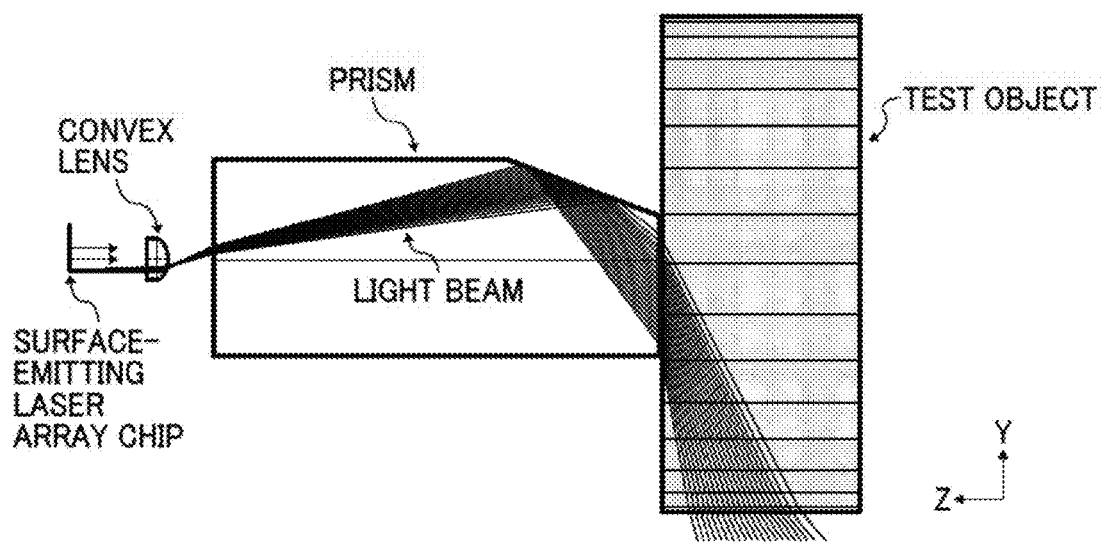
FIG. 51 illustrates an example of the result of the optical simulation according to a control sample.

FIG. 51 illustrates, as a control sample, an example of the result of the optical simulation where the lens is configured such that the focal length f=600 μm and the attached position L=1.6 mm. When the difference between L and f becomes equal to or greater than 1 mm, as illustrated in FIG. 51, the laser beam diverges too widely. In such cases where the laser beam diverges in an excessive manner as described above, the incident plane of the test object needs to be broadened. However, the practical size of the incident plane of the test object in the NIRS is actually about 92 mm at the maximum. This restriction is present because the space among the roots of the hairs of a human is about 2 mm and the hairs optically disturb the NIRS when the dimension is wider than the above. With such disturbance, the NIRS with high resolution cannot be achieved. In short, it is desired that the difference between L and f be shorter than 1 mm.

The first and second lenses illustrated in FIG. 40 are directly attached to a ceramic package on which the surface-emitting laser array chip is mounted, such that these lenses are disposed at designed positions in a precise and stable manner.

In FIG. 49, the convex surface of the lens is directed to the surface emitting laser side. However, the direction of the convex lens may be the other way around. When the lens is arranged such that the convex surface of the lens is directed to the surface emitting laser side and the planar portion of the lens is directed to the test object as illustrated in FIG. 49, the distance between the surface-emitting laser array chip and the lens can be lengthened. In the chip implementation processes, it is desired that the allowed distance be long to a certain extent. When the allowed distance is sufficiently long, the interference of parts or an arm that picks up the parts in the implementation processes can be prevented.

The lens may be any optics as long as it can refract the light. For example, a gradient index (GRIN) lens that utilizes the refractive distribution of an optical fiber may be used for the lens. When such a GRIN lens is adopted, a low-cost lens with a small spherical aberration and a small f number can be selected compared with when a spherical lens is adopted.

In the second example, the light enters the edge of the lens rather than the center of the lens. For this reason, it is desired that the spherical aberration be smaller.

As described above, each of the light source modules LM (type I, type II, and type II) according to the second example emits a plurality of bundles of light rays that are not parallel to each other (see FIG. 40, FIG. 42A, FIG. 42B, and FIG. 43). From the light source modules LM (type I and type II), two light rays with different wavelengths, where the optical paths are approximately parallel to each other and are close to each other, are emitted (see FIG. 40, FIG. 42A, and FIG. 42B). From the light source module LM (type III) according to the second example, two light rays with different wavelengths, where the optical paths are not parallel to each other and approximately overlap one another, are emitted (see FIG. 43).

Then, these bundles of light rays that are not parallel to each other emitted from the light source modules LM (type I, type II, and type III) enter an approximately same point of the test object (see FIG. 40, FIG. 42A, FIG. 42B, and FIG. 43). The two light rays emitted from the light source module LM (type III), where the wavelengths are different from each other and the optical paths approximately overlap one another, enter the same point of the test object (see FIG. 43).

For example, when the light source modules LM are disposed at about 60 mm intervals, the term "approximately same point" described above indicates an approximately same point with reference to such 60 mm. More specifically, a plurality of positions that are separated from each other by about several millimeters are considered to be approximately same points.

The term "same point" described above indicates a higher similarity than the term "approximately same point", but does not always mean exactly the same point. More specifically, a plurality of positions that are separated from each other by the degree equal to or shorter than 1 millimeter are considered to be the identical points.

The expression "optical paths approximately overlap one another" as described above indicates that the angle that the two angles that are not parallel to each other form is equal to or smaller than 10 degrees. Note that in order to increase the degree of conformity of the optical paths as much as possible, it is desired that the angle that the two angles that are not parallel to each other form be equal to or smaller than 1 degree.

In an algorithm for solving a reverse problem, an optical simulation where the position of the light source module LM is set is performed. In such an optical simulation, if the shifting of the position at which the light enters the test object is precisely set, no error occurs in the estimation of the reverse problem.

However, if it is desired that the probes be disposed with high density and with the space thereamong being equal to or wider than 10 mm as in, for example, JP-3779134-B, the multiple light source modules LM need to be disposed independently. Note that such an operation of disposing a plurality of light source modules LM is very much a complicated operation where the hairs need to be moved away on a one-hair-by-one-hair basis, and such complicated operation increases as the number of light source modules LM increases.

In the present embodiment, as will be described later in detail, the installation of only one light source module LM enables the acquisition of the amount of information that is equivalent to that obtained by the installation of a plurality of light source modules LM. Accordingly, high-resolution detection can be achieved as in the high-density probes of JP-3779134-B, without increasing complicated operation.

Figure 52A:
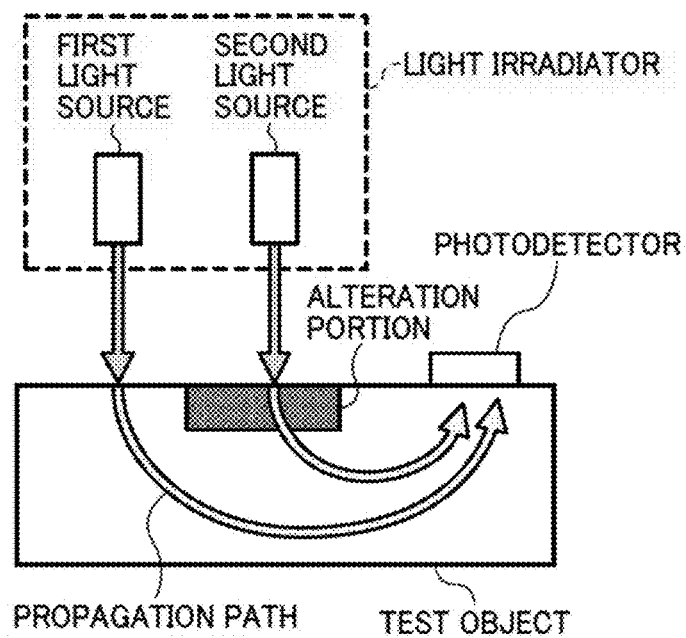
FIG. 52A is a diagram illustrating the operation of an optical sensor according to a control sample.

In the light source module according to a control sample as illustrated in FIG. 52A where a plurality of light rays that are parallel to each other enter a living body, an error occurs in the detection when an alteration portion is present near the surface of the living body. The term "alteration portion" indicates a portion with special optical properties, and includes, for example, roots of a hair and a colored skin. When such an alteration portion is present in the present control sample, the light rays emitted from the first light source and the second light source, respectively, enter different positions of the test object. For this reason, there may be some cases in which, for example, only the light emitted from the second light source passes through the alteration portion. When the difference between the first light source and the second light source is calculated, such an alteration portion may cause a noise.

Figure 52B:
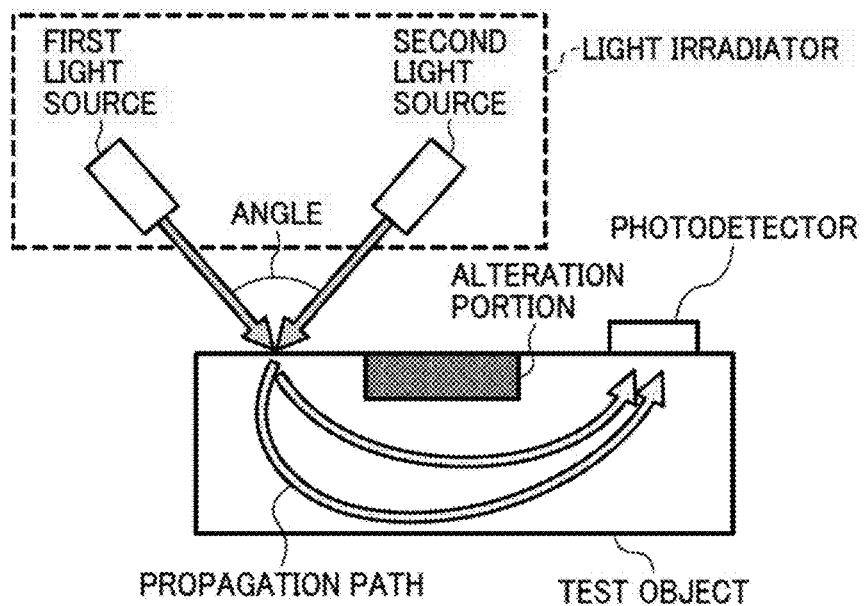
FIG. 52B is a diagram illustrating the operation of an optical sensor according to the first embodiment of the present invention.

By contrast, in the present embodiment, as illustrated in FIG. 52B, the light rays emitted from the first light source and the second light source, respectively, pass through an "approximately same point" of the surface of the skin. Accordingly, when one of the light rays emitted from the first light source and the second light source, respectively, pass through the alteration portion, the other one of the light rays also passes through the alteration portion. In a similar manner, when one of the light rays emitted from the first light source and the second light source, respectively, does not pass through the alteration portion, the other one of the light rays also does not pass through the alteration portion. More specifically, the light rays emitted from the first light source and the second light source, respectively, pass through the same optical path near the surface of the skin, and pass through different optical paths in a deeper portion. In other words, the configuration is insensitive to a difference near the surface of the skin, but is sensitive to a difference near the brain tissue. The resolution improves by reducing the noise near the surface of the skin. As described above, the term "approximately same point" allows a displacement of about several millimeters.

In the second example, a transparent gel is dripped onto the window member provided for the housing such that the transparent gel intervenes between the window member and the surface of the test object and the air is removed.

In the conventional light source module, the light that is once radiated in the air enters the surface of the skin and propagates inside the body. In such a configuration, a difference in refractive index arises between the refractive index 1.0 of the air and the refractive index 1.37 of a living body. As such a difference in refractive index arises, reflection and scattering occur. Moreover, the refractive index inside the living body in which the light propagates is smaller than that of the air outside the living body. For this reason, the propagation angle inside the living body decreases than the incident angle. The refraction of light on the interface can be understood from the Snell laws of reflection. The Snell law (the law of reflection) can be described by refractive indexes only.

Figure 53:
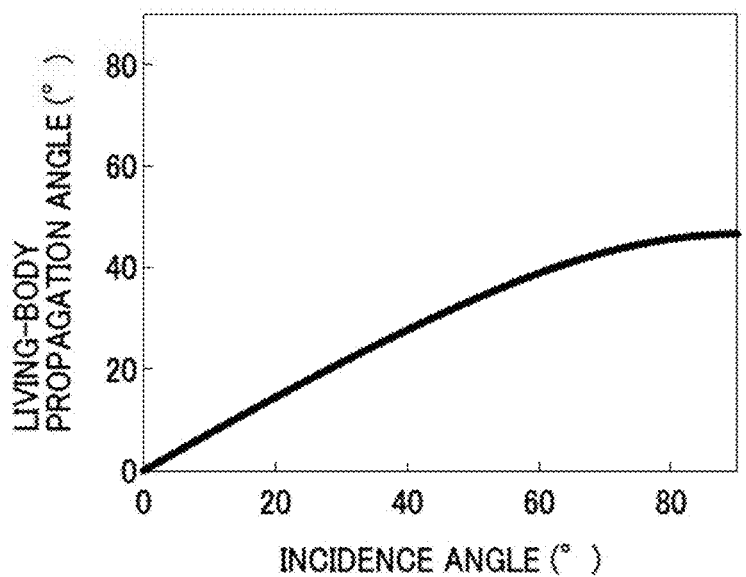
FIG. 53 is a graph illustrating the relation between the propagation angle inside the living body and the incident angle that a light forms with the surface of a living body when the light in the air enters the living body.

More specifically, the relation (refraction of light) between the propagation angle inside the living body and the incident angle on the interface between the air on the on the light entering side (refractive index 1.0) and the living body on the propagation side (refractive index 1.37) is depicted by the graph in FIG. 53. As understood from FIG. 53, even when the incident angle of the light that enters the living body is 60 degrees, the propagation angle of the light that has entered the living body is reduced to 40 degrees. Accordingly, even if a desired propagation angle of the light that has entered the living body is equal to or greater than 60 degrees, such a propagation angle cannot be achieved by the incident light from the air. In other words, it is difficult to form a propagation angle of large degree inside the living body from the light that has once released into the air.

Figure 54:
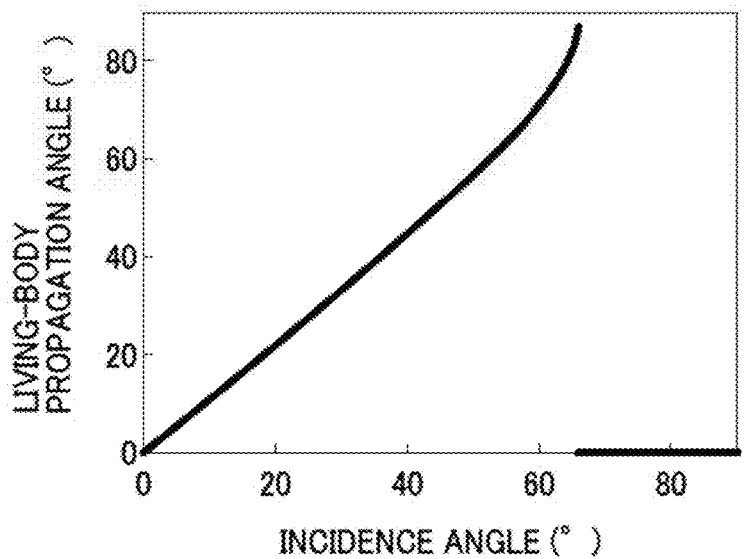
FIG. 54 is a graph illustrating the relation between the propagation angle inside the living body and the incident angle, which a light forms with the surface of a living body when the light in the resin enters the living body, according to the second example of the first embodiment of the present invention.

In order to deal with such a situation, in the second example, the refractive index of the transparent resin that makes up the window member of the light source module LM is designed to be greater than the refractive index 1.37 of the living body (for example, equal to or greater than 1.5) (see FIG. 54). In this configuration, when the light is emitted from the light source module LM with the incident angle of 60 degrees, the propagation angle of the light that directly enters the living body becomes greater than 70 degrees inside the living body. When the angle is smaller in the design, the light source module LM can be downsized.

In the light source module LM (type I) according to the second example, as illustrated in FIG. 40, the light that is emitted from the surface emitting laser in the direction parallel to the optical axis of the lens is refracted by the lens, and travels in a direction inclined by about 20 degrees with reference to the optical axis of the lens and enters the window member. The window member is designed to have the refractive index of about 1.5. The light that has passed through the lens is refracted when it enters the window member. However, such refraction is not large as the incident angle is not acute. The light that has entered the window member is deflected by the reflection plane of the prism, and travels in a direction inclined by about 55 degrees with reference to the optical axis of the lens. This angle of 55 degrees is the angle inside the window member of the refractive index 1.5, and as illustrated in FIG. 54, the propagation angle inside the living body (of the refractive index 1.37) is about 60 degrees.

In order for the light emitted from the light source module LM to propagate inside a pseudo living body in a direct manner, it is necessary to remove the airspace that exists in the interface between the pseudo living body and the light source module LM. In the present embodiment, transparent gel is used to remove such airspace. The transparent gel used here is an aqueous glycerin solution that goes well with a pseudo living body. The volatility of the transparent gel is controlled so as not to evaporate during the inspection while the light source module LM is closed by a lid, and the volatility of the transparent gel is controlled so as to evaporate or soak into the pseudo living body at an appropriate timing after the inspection is done. The optical properties of the transparent gel are controlled to become transparent near a wavelength of 780 nm, and the refractive index is adjusted to be close to that of the surface of pseudo living body. In the present example, the refractive index is adjusted to be about 1.37. Due to this adjustment, the difference in refractive index on the bumps and dips of the surface of the pseudo living body can be attenuated, and a state of no reflection can be achieved. Accordingly, the reflection on the surface of the pseudo living body can be almost eliminated. There are physical bumps and dips on interface with the pseudo living body, but there are no optical bumps and dips. Accordingly, no scattering occurs. As a result, the light emitted from the light source module LM can precisely be propagated inside the pseudo living body in an appropriate propagation direction according to the exit angle. As known in the art, the propagation inside the pseudo living body causes scattering strongly. However, the scattering on the surface of the skin is not small. According to the configuration as described above, the anisotropy of the light can be secured to a large degree. As the anisotropy can be secured to a large degree, the incident angles of the multiple light rays emitted from the light source module LM on the pseudo living body can be varied widely, and as will be described later, the incident angles at which the multiple light rays enter the detection module DM can be varied widely.

Figure 55:
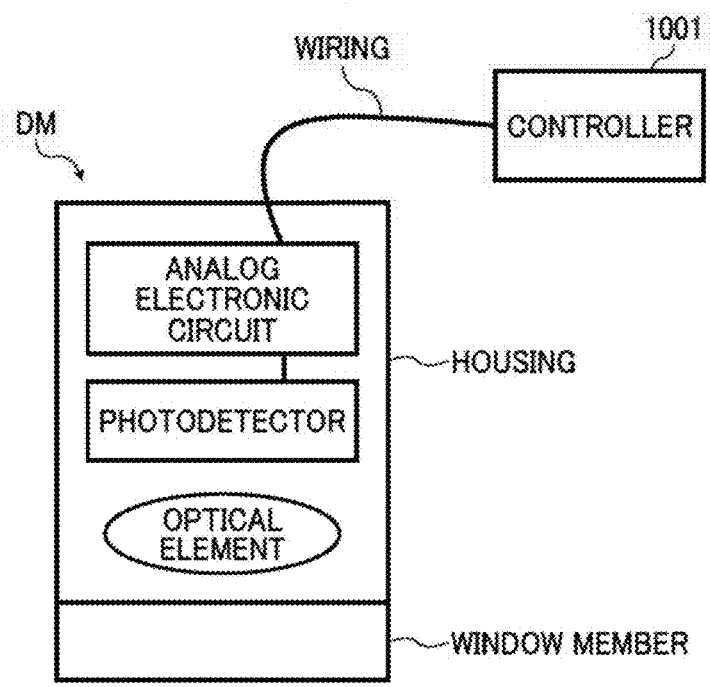
FIG. 55 is a first diagram illustrating an outline of the configuration of a detection module according to the second example of the first embodiment of the present invention.

As illustrated in FIG. 55, the detection module DM includes the housing, an optical element, a flexible circuit board on which a photoreceptor and an analog electronic circuit are mounted, a wiring connected to the flexible circuit board, and a connector.

Figure 56:
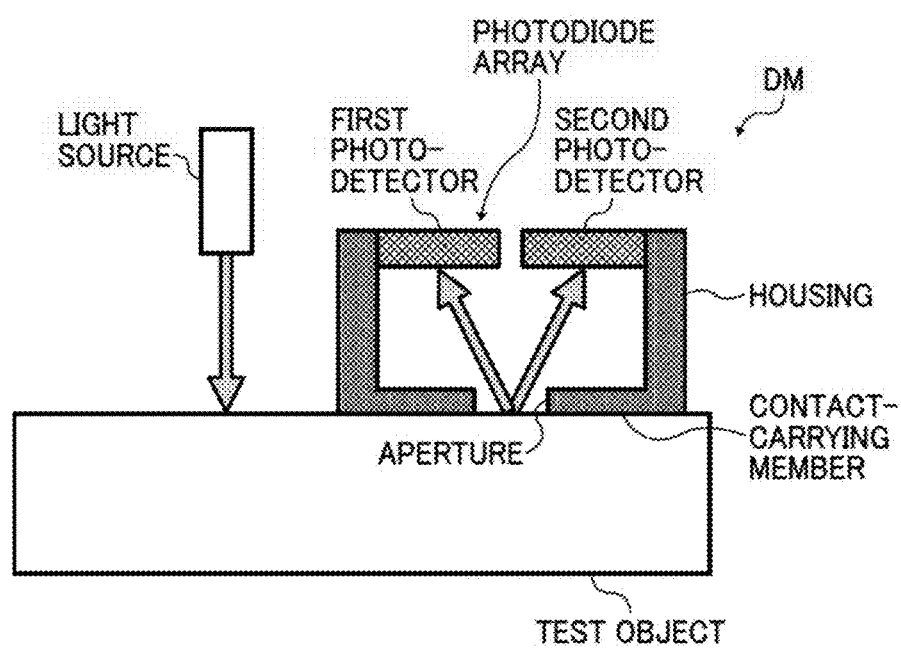
FIG. 56 is a second diagram illustrating an outline of the configuration of a detection module according to the second example of the first embodiment of the present invention.

As illustrated in FIG. 56, in the detection module DM, the light that is emitted from the light source to the test object propagates inside the test object, and the light is split into a plurality of light rays and are guided to a plurality of photoreceptors.

In the related art (see, for example, JP-2011-179903-A), in the DOT making use of fluorescence, a photoreceptor is arranged in accordance with a plurality of light rays emitted from a test object with varying angles. However, in this arrangement of a photoreceptor, the light of all the exit angles from the test object enters the photoreceptor.

By contrast, the detection module DM according to the present embodiment separately detects the split light rays that have entered the test object at an "approximately same point". As described above in regard to the light source module LM, the detection module DM can be designed when an optical simulation is performed. For this reason, a difference in position in the order of millimeter is no object in the precision of the "approximately same point".

Figure 57:
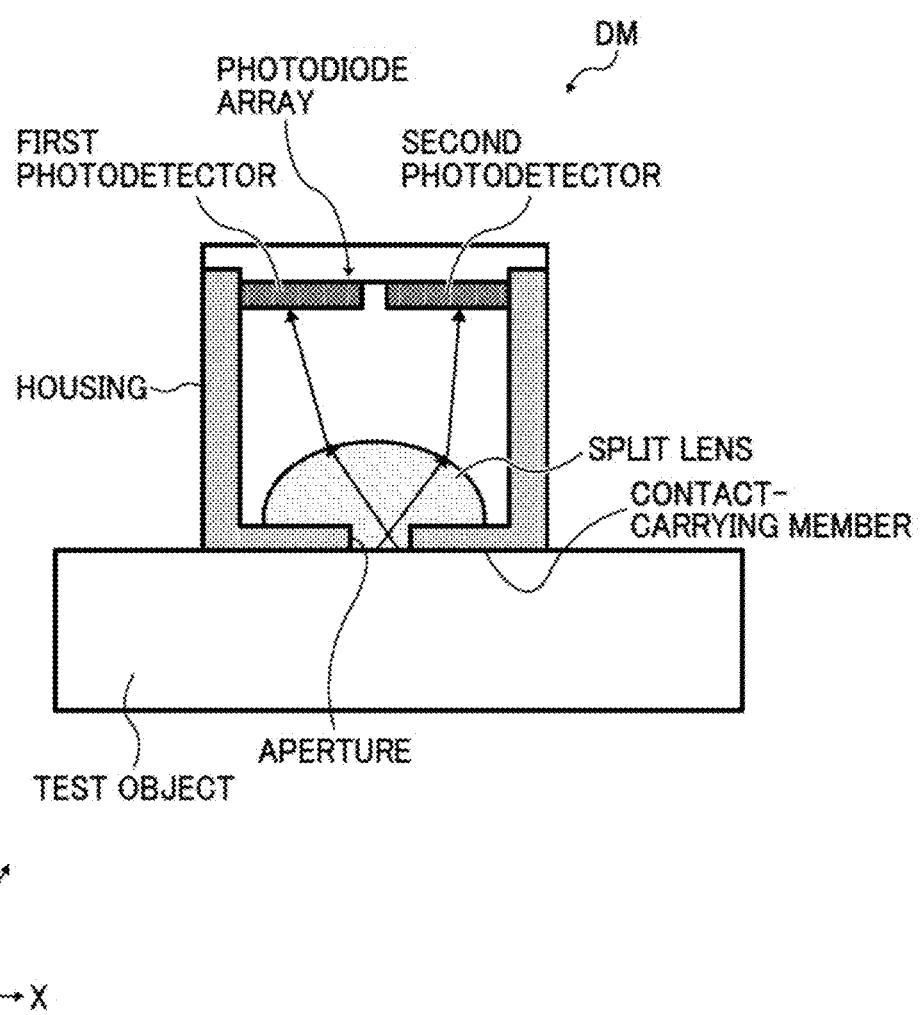
FIG. 57 is a third diagram illustrating an outline of the configuration of a detection module according to the second example of the first embodiment of the present invention.

Next, the detection module DM is described in detail. As illustrated in FIG. 57, the detection module DM includes a black-resin housing, a contact-carrying member consisting of an elastic body attached to a front end of the housing, a transparent split lens accommodated in the housing, and four photoreceptors. The housing has apertures at the front end of the housing and at the other end of the housing in contact with the contact-carrying member.

In the present embodiment, black rubber is used for the contact-carrying member in order to enhance the imperviousness to light. From the aperture of the contact-carrying member, a center portion (about φ1 mm) of the split lens stick out by about several hundreds of micrometers to the outside of the housing. As this portion contacts the surface of the living body, no air optically exists therein. Accordingly, refraction of Fresnel or scattering is prevented.

The stability of the detection module DM also further improves when the above-described transparent gel is used. Accordingly, the transparent gel is used for the detection module DM. The split lens is composed of a transparent resin, and its refractive index is about 1.8. The split lens is attached to the housing.

The aperture is a circular hole with the size of about 1 mm that penetrates the leading end and the contact-carrying member of the housing, and serves to limit the position of the light that propagates inside the test object and exits from the test object. The light rays that exit from the aperture are oriented to a plurality of different directions. The incident positions are determined by the aperture, and then the incident light is split into a plurality of light rays by the split lens. Accordingly, these multiple light rays can separately be detected.

Note that the aperture implements the configuration that the light rays exiting from the test object enter the photoreceptor from an "approximately same point" as described above.

The light rays that have passed through the aperture are refracted into different directions by the split lens according to the propagation directions of these light rays. Accordingly, the positions at which the light rays enter the photoreceptor are different from each other.

The split lens is a spherical lens, and has an about 3 mm diameter and an about 3 mm focal length f.

In the second example, the number of the partitions of the light by the split lens is four, and a photodiode array having four two-dimensionally arranged photoreceptors (photodiodes) is used. Note that in FIG. 57, only two of the four photoreceptors (photodiodes), i.e., the first and second photoreceptors, are illustrated.

In the present example, the photodiode array has a square shape where the sides have about 3 mm length, and each of the photodiodes has a square shape where the sides have 1.4 mm length. As illustrated in FIG. 57, an angle $\theta 2$ is defined, and the distance between the photodiode array and the aperture is about 5 mm.

One side of the lens is planar, and the other side of the lens is spherical. The planar side contacts the pseudo living body. As the position of the aperture is displaced from the focal point of the lens, the lens cannot form parallel light rays. The lens is used to limit the light that enters the photodiode array.

A simplified optical simulation is performed on this optical system, and the following result is obtained. The light with approximately $-10°<\theta 2<5°$ enters the second photoreceptor, and the light with approximately $-50°<\theta 2<10°$ enters the first photoreceptor. In other words, the light that has propagated inside the pseudo living body and exited from the aperture is split into a plurality of light rays according to the exit angles, and each of these multiple light rays enters one of the four photoreceptors.

In the second example, a spherical lens is used for the split lens. However, an aspherical lens may be used for the split lens to widen the angle of detection. The split accuracy and the number of partitions correlates with the estimation accuracy of an inverse problem as will be described later. For this reason, an optical system is determined by a desired level of estimation accuracy. In the present embodiment, a spherical lens is adopted and the number of partitions is four.

The photodiodes are electrically wired, and are connected to an operational amplifier. A semiconductor operational amplifier is used for the operational amplifier, and the operational amplifier supplies source voltage of 5 volts. As the detectable amount of light is very small, the amplification factor of the operational amplifier is high, and two-stage amplification is adopted. The amplification factor of about five digits is applied in the first stage, and the amplification factor of about three digits is applied in the second stage.

Figure 58:
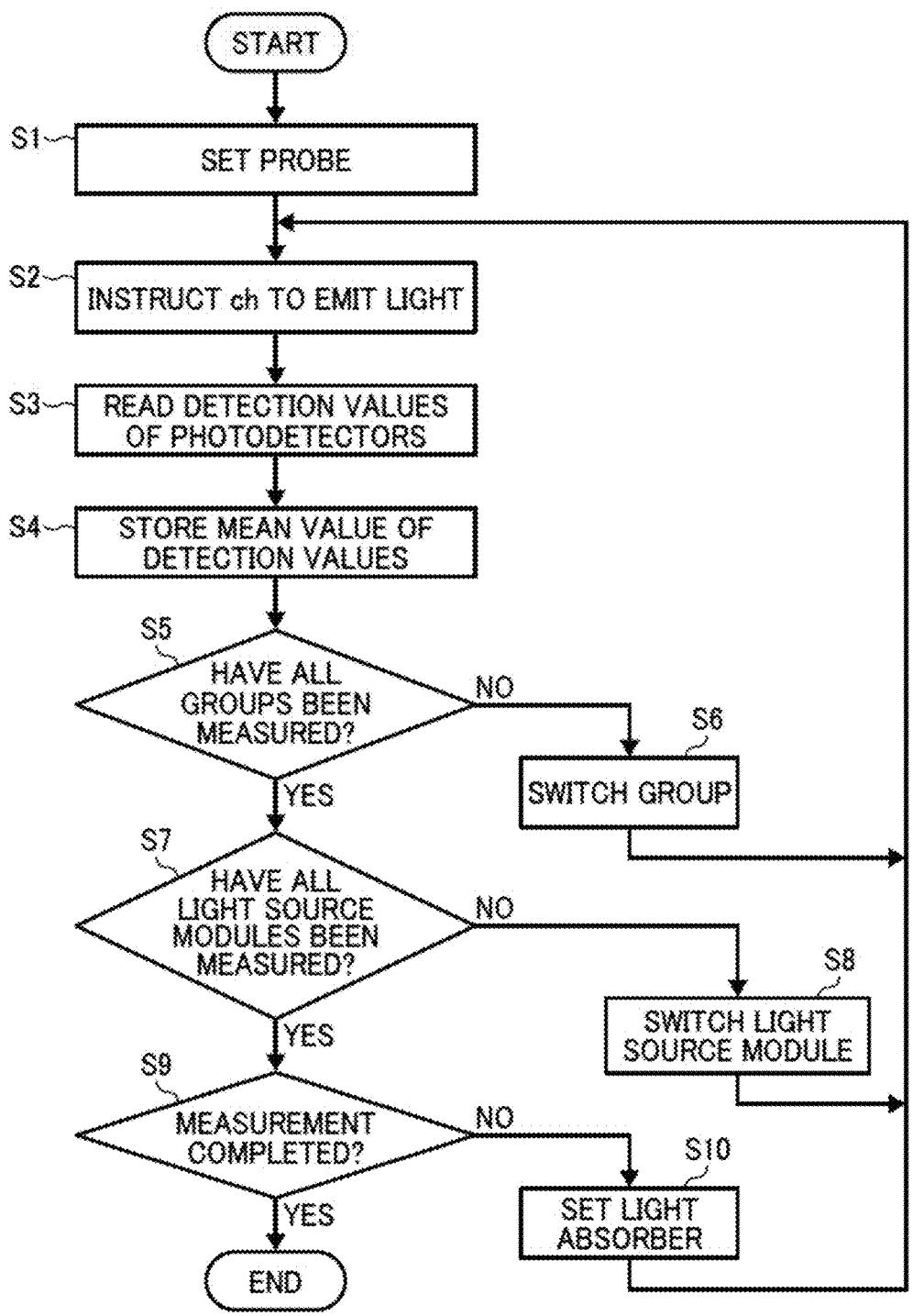
FIG. 58 is a flowchart of a method of detecting an optical property (position measuring method) according to the second example of the first embodiment of the present invention.

The method of measuring the position of the light absorber in the pseudo living body (method of detecting optical properties of the test object) according to the second example is described with reference to the flowchart depicted in FIG. 58.

Firstly, the probes (i.e., the light source modules LM and the detection modules DM) are set (inserted) into the pseudo living body (step S1). In so doing, a transparent gel is applied to between the acrylic watertank and each of the probes, and each of the probes is carefully set to a position determined by a fixation member so as not to mix bubbles into the transparent gel.

In the present embodiment, the number of probes is sixteen, including eight light source modules LM and eight detection modules DM, and the light source modules LM and the detection modules DM are alternately arranged in a grid pattern with equal pitches (see FIG. 39). The pitch in the grid pattern (space among points of the grid pattern) is 30 mm, and the space between each of the light source modules LM and detection modules DM is 30 mm.

In this state, a desired one of the channels of the light source module LM is instructed to emit light (step S2). The light source module LM is instructed to emit light on a group-by-group (four channels) basis, and the light-emission intensity is determined such that the current value becomes about 4 mW. The light emitting period is about 10 msec, and the detection values of all the photodiodes are read during the light emitting period, and the pieces of data (detection values) obtained at 1 msec intervals are averaged (step S3). Then, the averaged detection values is stored in the storage unit (step S4). In a similar manner, the 10 msec light emission, the measurement, and the data storage are repeated for the next group (steps S5, S6, and S2 to S4). Note that in each one of the light source modules LM, in a similar manner, the light emission of the four channels of the surface-emitting laser array chip of the oscillation wavelength of 780 mm and the light emission of the four channels of the surface-emitting laser array chip of the oscillation wavelength of 900 nm are performed in sequence.

However, in the data processing described below, the two wavelengths are treated in almost the same way. Accordingly, in the present embodiment, the measurement performed with two varying wavelengths is equivalent to the repeated measurement at the same position. When the changes in the real bloodstream are detected, the difference between the two wavelengths is used for the detection of oxyhemoglobin and reduced hemoglobin in a separate manner. However, in the present embodiment, measurement is performed one time using two surface-emitting laser array chips with varying oscillation wavelengths. Accordingly, the noise due to the variations in chips can be reduced.

After the light emission and measurement of all the groups of one of the light source modules LM are completed, the light emission of the next light source module LM is performed (steps S7, S8, and S2 to S6). In a similar manner to the above, the light source module LM is instructed to emit light on a group-by-group (4ch) basis. After the light emitting and measurement of all the light source modules LM are completed, a light absorber is set (steps S9 and S10). In order to set the light absorber at a desired position precisely with high reproducibility, an optical stage is used. After the light absorber is set as described above, the steps from the light emission of the channels to the storage of the detection values of the photodiodes are performed again (steps S2 to S9).

The stored data is labeled as $r(s, i, n)$ ($i=1, 2, 3, \ldots M$; $n=1, 2, 3, \ldots K$) with the light absorber and $r(0, i, n)$ ($i=1, 2, 3, \ldots, M$; $n=1, 2, 3, \ldots, K$) without the light absorber. "i" denotes the numbers assigned to the respective detection modules DM. "n" denotes the numbers assigned to the respective groups. Next, the difference $\Delta r(i, n)$ of the respective groups is calculated.

The method of calculating the position of the light absorber (the optical properties of the pseudo living body) according to the result of the measurement obtained by the measurement method as described above is similar to the method of calculating the position of the light absorber (the optical properties of the pseudo living body) according to the result of the measurement obtained by the measurement method as depicted in the flowchart of FIG. 15, and thus its description is omitted.

Figures 59, 60:
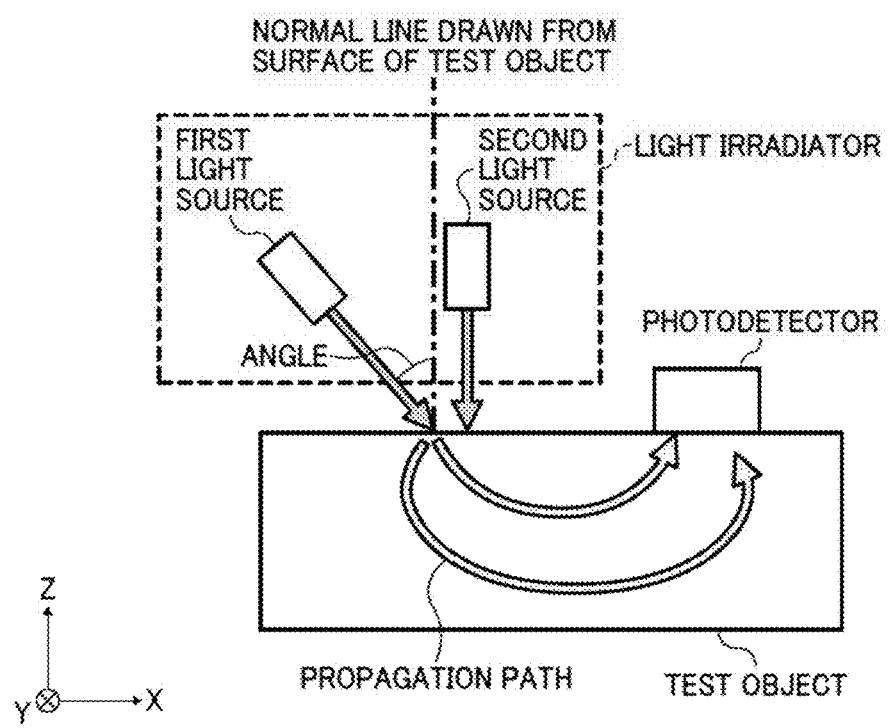
FIG. 59 is a diagram depicting the result of an inverse problem estimation according to the second example of the first embodiment of the present invention.
FIG. 60 is a diagram illustrating the operation of an optical sensor according to the first embodiment of the present invention.

As a result, the result of estimation as illustrated in FIG. 59 can be derived. FIG. 59 also depicts, as a control sample, the results of the detection in which only the center one of the five groups of the surface-emitting laser array chip (see FIG. 41) is controlled to emit light and the detection value of only one of the four photodiodes of the photodiode array is used. In the other respects, the numeric values are all processed in the same way as the present embodiment. The configuration of this control sample is almost equivalent to that of the conventional NIRS DOT device.

By contrast, in the present embodiment, the Bayes estimation is adopted as described above, and both the position and depth of the light absorber are detectable. In the results depicted in FIG. 59, a circular sign is given for a case where the position of the light absorber is successfully detected. In the present embodiment, as the distance in the depth direction of the light absorber (i.e., the Z-axis direction in FIG. 25) becomes longer, the distance to the light source module LM becomes longer, and the amount of the light that can propagate decreases. For this reason, as the depth of the position of the light absorber becomes deeper, it becomes more difficult to perform detection successfully. In the present embodiment, detection was successful up to the depth of about 6 mm. In the control sample, a known NIRS DOT device is used, and the detection in the depth direction was not successfully performed even with the application of the Bayes estimation. In order for the DOT to detect the three-dimensional position including the depth of the light absorber with high accuracy, the layout of probes with high density is required as known in the art. However, in the present embodiment, with the layout of probes with low density, the three-dimensional position of the light absorber was successfully detected with high accuracy.

As described above, the optical sensor 10 according to the present embodiment (the first and second examples) includes an irradiation system including a plurality of light source modules LM (light irradiators) to irradiate an object to be measured (test object) with light, and a detection system that detects the light that is emitted from the irradiation system and propagated inside the object to be measured. Then, each of the multiple light source modules LM emits multiple bundles of light rays that are not parallel to each other to an approximately same point of the object to be measured.

In the above configuration, as illustrated in FIG. 60, the multiple bundles of light rays that are not parallel to each other, which are emitted to an approximately same point of the object to be measured (scatterer), have different incident angles with reference to the object to be measured, and take varying propagation paths.

Accordingly, the amount of information obtained for the inside of the object to be measured increases, and higher resolution can be achieved. Moreover, as the resolution is improved, the density of the probes (i.e., the number of probes for each unit of dimension) can be reduced for the same desired resolution. Accordingly, attachability improves.

Accordingly, the optical sensor 10 can achieve higher resolution without degrading attachability to the object to be measured.

Note that the multiple bundles of light rays that are not parallel to each other but enter an approximately same point of the object to be measured indicates that the multiple bundles of light rays form angles with each other. In other words, as there exist angles formed by the multiple bundles of light rays, the propagation paths of the multiple bundles of light rays in the test object can be varied. By contrast, if the multiple bundles of light rays that enter an approximately same point of the object to be measured are parallel to each other (for example, if the multiple light rays are parallel to the normal line to the surface of the test object), the propagation paths of the multiple bundles of light rays in the object to be measured become the same.

The light source module LM according to the present embodiment includes a surface emitting laser array having a plurality of surface emitting lasers (light-emitting units), and a convex lens disposed in the optical path of a plurality of light rays emitted from the surface emitting lasers to form a plurality of light rays that are not parallel to each other. The distance between the surface emitting laser array and the principal point of the convex lens does not match the focal length of the convex lens.

Accordingly, the return light can be prevented from concentrating on the surface emitting laser, and the fluctuations in the output of the surface emitting laser can be prevented. As a result, the amount of the light emission of the surface emitting laser can be stabilized, and the accuracy of detection of the optical sensor 10 improves. Further, the resolution of the NIRS can be improved.

By contrast, if the surface emitting laser array is at the focal point of the convex lens, the light reflected from an external reflection plane is concentrated onto the surface emitting laser by the convex lens, and the laser oscillation becomes unstable. This phenomenon is called, for example, return light or self-mixing. If this phenomenon occurs when a surface emitting laser array is used as the light source of an optical sensor, the amount of light emission becomes unstable. See JP-2011-14228-A and JP-2012-132740-A for the detail.

The space between the convex lens and the surface emitting laser array is filled with a transparent resin whose refractive index is equivalent to that of the convex lens.

As a result, the refractive index does not change at the boundary of the interface between the convex lens and the surface emitting laser array, and the return light can be prevented. As a result, the amount of the light emission of the surface emitting laser array can be stabilized, and further, the resolution of the NIRS can be improved.

The detection system includes a plurality of detection modules DM each of which includes a plurality of photoreceptors (photodiodes) configured to receive the multiple light rays separately that are emitted from the light source module LM to the object to be measured and have propagated inside the object to be measured.

In this configuration, data of two different propagation paths inside the object to be measured can separately be obtained.

The detection module DM is disposed between the object to be measured and a plurality of photoreceptors (photodiodes), and has the housing and the contact-carrying member on which an aperture is formed. Moreover, some of each of the multiple light rays that have propagated inside the object to be measured passes through the aperture.

In this configuration, the light can be taken into the housing from an approximately same point of the object to be measured. More specifically, only light rays with limited incident angles enter the housing. Accordingly, each of a plurality of photoreceptors can receive light.

Moreover, the detection module DM includes the split lens (light-receptive lens) that separately guides some of the multiple light rays passed through the aperture to the multiple photoreceptors.

In this configuration, some of each of the multiple light rays passed through the aperture can separately enter the multiple photoreceptors with a stable amount of light. In other words, the detection module DM can receive the multiple light rays separately that are emitted from the light source module LM to the object to be measured and have propagated inside the object to be measured.

The light source module LM includes a window member that contacts the object to be measured and is composed of a material (transparent resin) whose refractive index is greater than that of the object to be measured. Accordingly, the propagation angle (refraction angle) of the light inside the object to be measured can be increased with reference to the incident angle on the object to be measured. As a result, compared with cases in which, for example, the light in the air enters the object to be measured, the propagation angle can be increased even with the same degree of incident angle. Accordingly the difference in propagation angle between the two light rays inside the object to be measured increases than the difference in incident angle between the two light rays that enter an approximately identical point of the object to be measured with varying incident angles, and the propagation paths of the multiple light rays in the test object can be varied significantly. As a result, an even higher resolution can be achieved.

The light source module LM includes a plurality of two-dimensionally disposed surface emitting lasers and an irradiation lens (lens) disposed in the optical path of a plurality of light rays emitted from the multiple surface emitting lasers.

In this configuration, the directions of travel of the light rays emitted from the multiple surface emitting lasers can be changed to desired directions (i.e., the directions towards the positions at which the corresponding prisms are disposed).

Moreover, the light source module LM includes a prism (reflection member) disposed on the optical path of the light that has passed through the irradiation lens, and the prism reflect the light towards a prescribed direction.

In this configuration, the direction of travel of the light emitted through the irradiation lens can further be changed to a desired direction. In other words, the incident angle on the object to be measured can be designed to a desired angle.

As described above, the optical sensor 10 is an optical sensor with a relatively simple configuration that effectively utilizes the anisotropy of the propagation of light to achieve high resolution. It is expected that the optical sensor to be applied to various kinds of fields such as the field of the DOT.

The optical examination device 100 includes the optical sensor 10, and a controller (optical properties calculator) that calculates the optical properties of the object to be measured based on the detection results of the optical sensor 10.

In this configuration, the accuracy of the detection at the optical sensor 10 is high, and thus the optical properties of the object to be measured can be calculated with high accuracy.

The optical sensor 10 according to the present embodiment (the first and second examples) includes an irradiation system including a plurality of light source modules LM (light irradiators) to irradiate an object to be measured (for example, a living body) with light, and a detection system that detects the light that is emitted from the irradiation system and propagated inside the object to be measured. Each of the multiple light source modules LM can emit multiple light rays with different wavelengths to an approximately same point of the object to be measured.

In this configuration, the data inside the object to be measured can precisely be obtained.

More specifically, the position of the cerebral blood flow can be measured with high precision in a near-infrared spectroscopy (NIRS) device that performs an inverse problem estimation.

The light source module LM (type III) includes two channels (whose wavelengths in exiting light are different from each other) that separately emit two light rays with different wavelengths, the first and second lenses that are separately disposed in the optical paths of the two light rays with different wavelengths that are emitted from the two channels described above, and a prism for common use that is disposed in the optical paths of the two light rays with different wavelengths that have passed through the two lenses described above. Then, the optical paths of the two light rays with different wavelengths that are reflected on the prism approximately overlap one another. Note that the expression "optical paths approximately overlap one another" indicates that the angle that the optical paths of a desired pair of light rays forms is equal to or less than 10 degrees, where such a desired pair of light rays are chosen from a plurality of light rays with different wavelengths that are reflected on a prism.

As described above, with a relatively simple configuration, two light rays with different wavelengths can irradiate an identical point of the object to be measured.

In the light source module LM (type III), a prism includes reflection planes (total reflection planes R1 and R2) that reflect two light rays with different wavelengths that have passed through the first and second leases, and the optical paths of the two light rays with different wavelengths from the first and second lenses to the reflection planes are not parallel to each other.

As described above, the configuration can be simplified and the cost can be reduced compared with cases in which two light rays with different wavelengths are separately reflected on two reflection planes.

In the light source module LM (type III), the number of optical components and the cost of installation can be reduced compared with cases in which a plurality of optical elements are used instead of the prism.

In the light source module LM (type III), the optical paths of the two light rays with different wavelengths from the first and second lenses to the reflection planes of the prism get close to each other as the light rays get close to the reflection planes of the prism. For this reason, these light rays can be reflected on the reflection planes towards an object to be measured in a state where the optical paths of these light rays are made close to each other.

In the light source module LM (type III), the two light rays with different wavelengths that are reflected on the reflection planes of the prism intersect near the exit end of the light source module LM (type III). Accordingly, these two light rays can enter an identical point of the object to be measured with reliability.

In the light source module LM (type III), each of the two channels includes a plurality of light-emitting units that are arranged in an array, and the relative positions of these multiple light-emitting units and the optical axis of the corresponding one of the lenses differ among a plurality of light sources. Accordingly, the two light rays with different wavelengths that are emitted from two light-emitting units that correspond to each other between two channels can be emitted from the first and second lenses in a state where the two light rays are not parallel to each other.

In the light source module LM (type III), the center of each of the channels (center of array) is shifted from the optical axis of the corresponding one of the lenses. Accordingly, when it is assumed that two light-emitting units that correspond to each other between two channels is a pair, the relative positions of all the pairs of light-emitting units and the optical axes of the lenses can be varied.

The space between the first and second lenses and the corresponding two channels may be filled with a transparent resin whose refractive index is equivalent to that of the first and second lenses (see FIG. 47).

The first and second lenses may have a convex shape on the sides of the corresponding channels (see FIG. 49).

The optical element in common between the light source module LM (type II) and the light source module LM (type III) is not limited to a prism, but may be any member as long as it includes at least one reflection plane that can reflect a plurality of light rays with different wavelengths.

The optical examination method according to the first embodiment of the present invention is a method of performing an optical examination on a test object, using an optical sensor 10 including an irradiation system including a plurality of light source modules LM to irradiate an object to be measured with light, and a detection system including a plurality of detection modules DM to detect the amount of light that is emitted from the irradiation system to the object to be measured and propagated inside the object to be measured. The method includes a step of obtaining a first detection light quantity distribution that is the detection light quantity distribution (light quantity distribution) obtained for each of the multiple optical models that simulate a test object, by performing the simulation where the optical sensor 10 is virtually used, a step of obtaining, using the optical sensor 10, the second detection light quantity distribution (light quantity distribution) that is the distribution of the amount of the light detected on the test object, and a step of comparing the first detection light quantity distribution with the second detection light quantity distribution to select an optical model suited to the test object from the multiple optical models.

In such a configuration, the detection light quantity distribution of the test object can be evaluated with reference to the detection light quantity distribution of the optical model suited to the test object. Accordingly, an examination (for example, the acquisition of the internal information of a test object) can be performed with minimal error.

Accordingly, the accuracy of the examination improves.

Moreover, the optical examination method according to the first embodiment further includes a step of obtaining the internal information of the test object using the first detection light quantity distribution of the selected optical model and the second detection light quantity distribution. Accordingly, the internal information of the test object can precisely be obtained.

In the above information obtaining step, the positions of light absorbers inside the test object are estimated. Accordingly, the estimation accuracy of the positions of the light absorbers (i.e., the estimation accuracy of the reverse problem in the present embodiment) improves.

Moreover, the simulation as described above in the present embodiment is the Monte Carlo simulation. Accordingly, the estimation accuracy of the reverse problem in the present embodiment further improves.

Each of the optical models includes a virtual layer (for example, a hair layer) that may exist between the surface of the test object and the light source module LM and the detection module DM (the light source module LM and the detection module DM may collectively be referred to as probes). Accordingly, an error in the amount of detection light due to the contact failure between the surface of the test object and the probes, due to the involvement by hairs, can be reduced.

Prior to the step of selecting as described above, the optical examination method according to the first embodiment further includes a step of correcting the first detection light quantity distribution. Accordingly, the accuracy of the selection of the optical model improves.

In the simulation described above, the multiple light source modules LM and detection modules DM are virtually installed in the optical models in such a manner that at least two detection modules DM are adjacent to each one of the light source modules LM. In the step of correcting the first detection light quantity distribution, the amounts of the light rays that are emitted from the light source modules LM to an optical model and have propagated through the optical model in the above simulation, which are detected by the at least two detection modules DM that are adjacent to the light source module LM, are compared with each other. Based on the results of the comparison, at least one of the amounts of the detection light detected by the at least two photodetectors can be corrected.

In such a configuration, the error in the amounts of the light that is emitted from the light source modules LM to an optical model and has propagated through the optical model in the above simulation, which are detected by the multiple detection modules DM, can be reduced. In other words, the error due to a contact failure or the like caused between a detection module DM and the surface of an object to be measured in the above simulation can be reduced.

In the simulation described above, the multiple light source modules LM and detection modules DM are virtually installed in the optical models in such a manner that at least two light source modules LM are adjacent to each one of the detection modules DM. In the step of correcting the first detection light quantity distribution, the amounts of the light rays that are emitted from at least two light source modules LM that are adjacent to the detection modules DM to an optical model and have propagated through the optical model in the above simulation, which are detected by the at least two detection modules DM, are compared with each other. Based on the results of the comparison, the amount of the light that is emitted from at least one light irradiator of at least two light source modules LM, which is detected by the detection module DM, can be corrected.

In such a configuration, the error in the amounts of the light rays that are emitted from a plurality of light source modules LM to an optical model and have propagated through the optical model in the above simulation, which are detected by the multiple detection modules DM, can be reduced. In other words, the error due to a contact failure or the like caused between a light source module LM and the surface of an optical model in the above simulation can be reduced.

In the simulation described above, the multiple light source modules LM and detection modules DM are virtually installed in the optical models in such a manner that the light source modules LM and the detection modules DM are adjacent to each other in both the first and second directions that intersect. Here, it is assumed in an optical model that two light source modules LM that are adjacent to each other are the first and second light source modules LM and two detection modules DM that are adjacent to each other and adjacent to each of the first and second light source modules LM are the first and second detection modules DM. In the step of correcting the first detection light quantity distribution, the amounts of the light rays 1 and 2 that are emitted from the first light source module LM to an optical model and have propagated through the optical model in the above simulation, which are detected by the first and second detection modules DM, are compared with the amounts of the light rays 3 and 4 that are emitted from the second light source module LM to the optical model and have propagated through the optical model, which are detected by the first and second detection modules DM. Based on the results of the comparison, at least one of the amounts of the detection light 1, 2, 3, and 4 can be corrected.

In such a configuration, the error in the amounts of the detection light due to a difference in the state of installation of four probes that are adjacent to each other in the above simulation can be reduced.

The optical examination device 100 according to the first embodiment of the present invention is an optical examination device that examines a test object and includes the optical sensor 10 including an irradiation system including a plurality of light source modules LM to irradiate an object to be measured with light, and a detection system including a plurality of detection modules DM to detect the amount of light that is emitted from the irradiation system to the object to be measured and propagated inside the object to be measured, and a control system including a controller 1001 that controls the irradiation system and obtains the amount of the light detected by the detection system, where the control system uses the optical sensor 10 to obtain the first detection light quantity distribution that is the distribution of the amount of the light detected on a test object, and compares the obtained first detection light quantity distribution with the second detection light quantity distribution that is obtained by simulation where the optical sensor 10 is virtually used, where the second detection light quantity distribution is the distribution of the amount of the light detected on each of a plurality of optical models that simulate various types of test object, to select an optical model suited to the test object from the multiple optical models.

In such a configuration, the detection light quantity distribution of the test object can be evaluated with reference to the detection light quantity distribution of the optical model suited to the test object. Accordingly, an examination (for example, the acquisition of the internal information of a test object) can be performed with minimal error.

Accordingly, the accuracy of the examination improves.

The control system obtains the internal information of the test object using the second detection light quantity distribution of the selected optical model and the first detection light quantity distribution. Accordingly, the internal information of the test object can precisely be obtained.

Moreover, the control system estimates the positions of light absorbers inside the test object. Accordingly, the estimation accuracy of the positions of the light absorbers (i.e., the estimation accuracy of the reverse problem in the present embodiment) improves.

Further, the control system uses the detection light quantity distribution (the second detection light quantity distribution) of at least one optical model including the optical model selected from the multiple optical models to correct the detection light quantity distribution of the test object (the first detection light quantity distribution). Accordingly, the accuracy of the selection of the optical model improves.

As a result, in the first embodiment, the error at a contact-carrying member can be reduced as a plurality of light rays enters an identical point of the object to be measured. Accordingly, the internal information of the object to be measured (for example, the amount of cerebral blood flow) can be detected with precision. Moreover, as the same point of the object to be measured is irradiated with a plurality of light rays, for example, the number of optical models that simulate a contact failure can be reduced, and the accuracy of the selection improves. As the error in the selection is reduced, the internal information (for example, of the cerebral blood flow) can be detected with high accuracy.

The optical examination method according to the first embodiment may be described in a simplified manner as follows. "A method of performing an optical examination on a test object, using an optical sensor, the method including a step of obtaining a first detection light quantity distribution that is the detection light quantity distribution obtained for each of the multiple optical models that simulate a test object, by performing the simulation where the optical sensor 10 is virtually used, a step of obtaining, using the optical sensor 10, the second detection light quantity distribution that is the distribution of the amount of light detected on the test object, and a step of comparing the first detection light quantity distribution with the second detection light quantity distribution to select an optical model suited to the test object from the multiple optical models."

Second Embodiment

Next, a second embodiment of the present invention is described. In the present embodiment, a method of adapting the probes described above in the first embodiment to an actual human body is described. In the present embodiment, the test object is changed from the phantom (the watertank filled with whitish water) to the human head, and the light absorber is changed to the bloodstream in the brain.

In the present embodiment, the distribution of the bloodstream inside the brain is to be estimated with high accuracy. As known in the art, in the present embodiment, a test subject (test object) is measured and the shape is modeled based on the obtained data, and then the Monte Carlo simulation is performed. Moreover, the magnetic resonance imaging (MRI) is used to measure the shape of the head of the test subject. More specifically, the shapes of the four sites of the head including the scalp, the skull, the cerebrospinal fluid, and the cerebral cortex are measured from the images.

Such three-dimensional data is required for high-precision detection in the present embodiment. However, such three-dimensional data may be substituted, for example, by preparing a plurality of model brains (optical models) of standard shape and selecting one of these model brains appropriately. For each of the sites, a normal scattering coefficient, anisotropy, and absorption coefficient are known, and thus these known values are used. The probes are precisely attached to the head by fixtures, and the attached positions are also precisely measured. An optical simulation is performed using the accurate shapes and the layout of the elements and the values of the sites. As described above, if high-precision measurement can be done without MRI images, the cost of the examination can be lowered.

Figure 61:
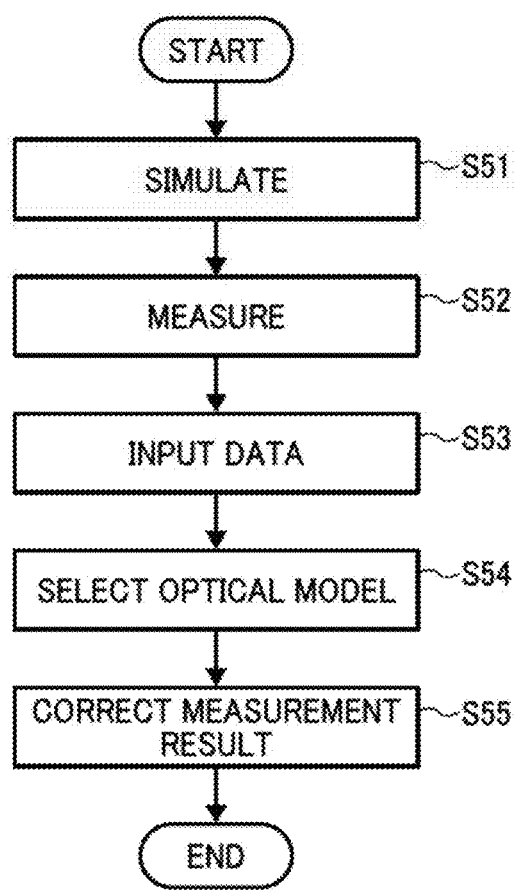
FIG. 61 is a flowchart of an optical examination method (i.e., measurement result correction processes) according to a second embodiment of the present invention.

In the present embodiment, measurement results are corrected according to the steps depicted in the flowchart of FIG. 61.

In a similar manner to the first embodiment, optical simulation is performed for a plurality of optical models in the present embodiment (step S51). Also in the present embodiment, the Monte Carlo simulation is performed. Several sets of four light source modules LM and four detection modules DM are fixed on the forehead of a head via folders. It is assumed that each of the light source modules LM has five directions and each of the detection modules DM has four directions. The conditions of angles or the like are assumed to be the same as those of the first embodiment as described above. The optical simulation is to be calculated for all the propagation angles and detection angles of all the pairs of probes (i.e., all the pairs of the light source modules LM and detection modules DM).

As described above, the Monte Carlo simulation is performed for each of the eight kinds of optical models illustrated in FIG. 17 to FIG. 24. In the Monte Carlo simulation, the optical constants depicted in FIG. 28 are used. Note that as the hair in the present embodiment has a thickness of about 100 micrometers (μm) as known in the art, the absorption coefficients are adjusted to a voxel of 1 millimeter (mm) for the Monte Carlo simulation. Moreover, a plurality of optical models are to be prepared, for example, for the varying positions of the hair. For example, the hair may have a grid pattern directly below a light source module LM or detection module DM or have one layer between the light source module LM or detection module DM. FIG. 29 depicts the detail of the eight optical models. In FIG. 29, the seven optical models 2 to 8 are depicted with reference to the optical model 1 that serves as the standard. In the Monte Carlo simulation, it is desired that various kinds of optical models be prepared, and no limitation is indicated by these eight optical models 1 to 8.

By performing the simulation, as illustrated in FIG. 32B, a light quantity distribution where no cerebral blood flow is considered can be prepared. In FIG. 32B, the amount of the detection light of the light that enters a detection module DM in the direction A when the direction at which the light enters an optical model from the light source module LM1 is (1) is a standardized to be 1. FIG. 32B indicates an example of light quantity distribution where detection is performed for each item of the matrix with reference to the standardized light quantity. In FIG. 32B, 3×3 matrix is depicted. However, in the present embodiment, the matrix includes 16×20 rows and columns as the detection module DM has four probes in four directions and the light source module LM has four probes in five directions. In the light quantity distribution according to the present embodiment, varying results can be obtained in the optical simulation for each of the eight optical models 1 to 8 depicted in FIG. 29. The light quantity distribution of each of the optical models is compared with the result of the measurement performed on a test object, i.e., the light quantity distribution obtained by performing the physical measurement (step S52) to select an optical model that is most suited to the test object. In the present embodiment, an optical model whose light quantity distribution is most harmonized is selected. In so doing, calibration is to be performed in advance of the physical measurement. Such calibration is performed using a black box in which polyoxymethylene (POM) resins are disposed and a guide is attached to guide the probes to desired positions. Due to such calibration, a high degree of reproducibility can be achieved.

Figure 62:
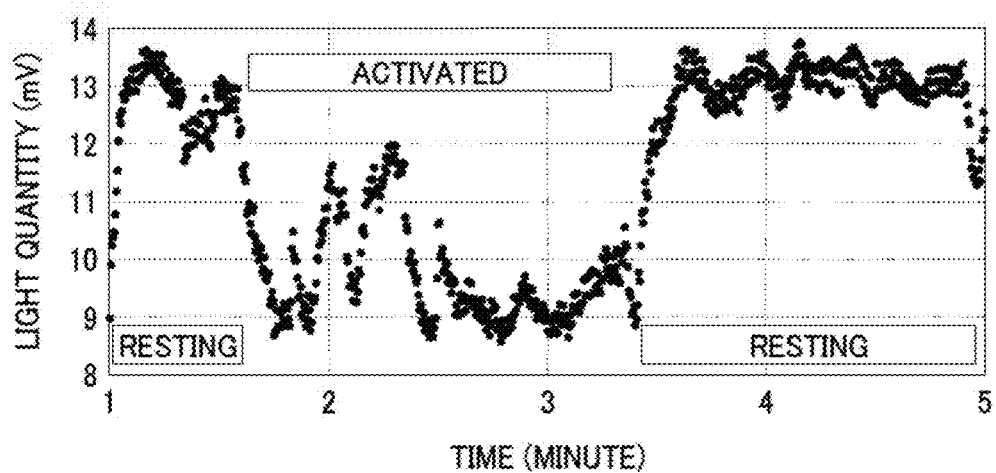
FIG. 62 is a graph illustrating the changes in light quantity in a resting state and activated state, according to the second embodiment of the present invention.

It is desired that the duration in time of the measurement (step S52) on a test object be equal to or longer than 20 seconds. The graph illustrated in FIG. 62 illustrates the results of the detection performed at probes attached to an area near the frontal lobe (forehead area). The vertical axis indicates the voltage value (light quantity) that is initially detected by photodiodes and then is converted from the current to the voltage. The horizontal axis indicates time, and a language fluency test is performed from the point 1.5 minutes after the start of the measurement to the point 3.5 minutes after the start of the measurement.

While such a language fluency test, the frontal lobes of the brain are stimulated and enter an activated state. In such an activated state, the cerebral blood flow is intensified and the light quantity in the section of activated state is decreased. In other words, the amount of propagated light is reduced due to the cerebral blood flow activated in the propagation path of the light, and the amount of detection light is decreased. At that time, the light quantity at the forehead area varies from 9 millivolts (mV) to 14 mV. If attention is focused on a resting state 3.5 minutes after the start of the measurement, the light quantity oscillates between 12.7 mV and 13.5 mV.

Figure 63:
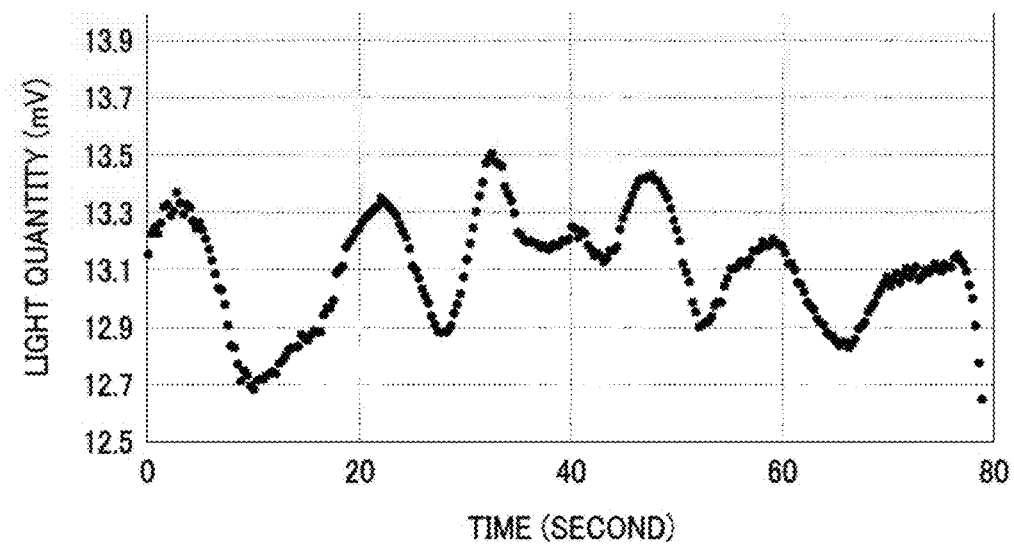
FIG. 63 is a graph illustrating the changes in light quantity in a resting state, according to the second embodiment of the present invention.

FIG. 63 is a graph illustrating the changes in light quantity in a resting state, according to the second embodiment of the present invention. In other words, the resting state illustrated in FIG. 62 is magnified in FIG. 63. The horizontal axis is converted into seconds. The cycle of the oscillation is about 20 seconds. It is known that the cerebral blood flow is measured like pulsation from such oscillation in the resting mode of the brain. In order to correct the oscillations in the resting mode, the measurement is to be maintained for equal to or longer than 20 seconds. The accuracy of the measurement improves by maintaining the measurement for equal to or longer than 20 seconds.

In the present embodiment, the largest value in light quantity is adopted from the period of 20 seconds. It is considered that the light quantity reaches a peak when the cerebral blood flow is reduced. Such a state where the cerebral blood flow is reduced is assumed in the optical models as described above. In other words, the state where the cerebral blood flow is reduced is best suited to the optical models. The harmonization with the optical models improves by adopting the largest value of the light quantity in the period of 20 seconds, and the precision of the correction improves.

In the next step S54, one of the optical models is selected. In order to select appropriate one of the optical models, the model is selected where each of the values in the matrix has the smallest error. More specifically, the difference in the matrix value is calculated between ((1), A) in the physical measurement and ((1), A) in the virtual measurement. Next, the difference in the matrix value is calculated between ((2), B) in the physical measurement and ((2). B) in the virtual measurement. This calculation is repeated in sequence, and the sum total of the squares of the differences in the values of the corresponding matrix elements between the physical measurement and the virtual measurement is calculated. Then, the optical model with the smallest value in the above sum total is determined to be the optimum one.

In the present embodiment, data whose expected effect due to the correction is greater than the others is selected in the selection of the model, and the value of such data is input (step S53). The "data whose expected effect due to the correction is greater than the others" (this data may be referred to as "input data" in the following description) includes, for example, the gender, the age, the height, the weight, the length of the periphery of a head, the thickness of hair, the density of hairs, and the color of skin of the test object. By taking into considerations these conditions, the precision of the selection from the eight optical models 1 to 8 as illustrated in FIG. 29 improves.

Figure 64:
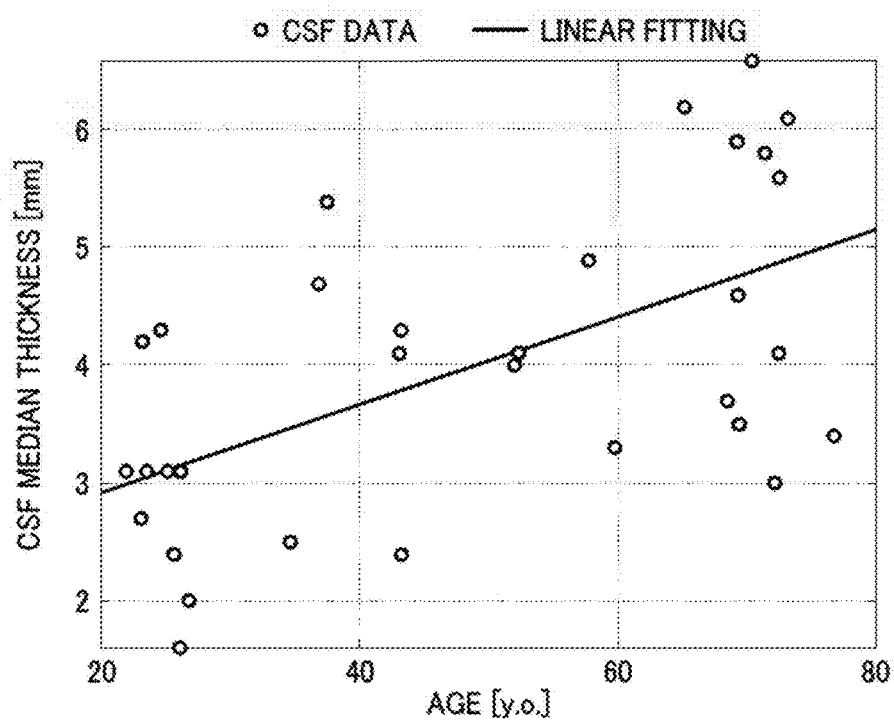
FIG. 64 is a graph illustrating the relation of the age and the thickness of the cerebrospinal fluid (CSF) layer, according to the second embodiment of the present invention.

For example, FIG. 64 depicts an example in which the correlation is examined between the age and the thickness of the layer of the cerebrospinal fluid (bone marrow fluid layer). By inputting the age, to some extent, the thickness of the layer of the cerebrospinal fluid can be predicted. In the present embodiment, for example, if the age is 50, thickness of the layer of the cerebrospinal fluid can be predicted to be about 4 mm from the median line drawn in the graph of FIG. 64. According to this fact, a different penalty is given to 4 mm patterns and 5 mm patterns of the layer of the cerebrospinal fluid in the models. By so doing, the accuracy of the selection improves. More specifically, when the age is 50, different values are given to the thickness of the layer of the cerebrospinal fluid as follows. The value "1" is set to the 4 mm model, and the value "1.2" is set to the 5 mm model. Moreover, the value "1.4" is set to the 6 mm model and the value "1.2" is set to the 3 mm model. Such set values are integrated into the values in the selection according to the first embodiment where the least squares are calculated for the errors between the light quantity distribution of a test object obtained by the physical measurement and the light quantity distribution of the optical model obtained by the simulation. Accordingly, when the age is 50, there is a high probability that the model in which the thickness of the cerebrospinal fluid is 4 min is selected.

A penalty is given to some optical models in a manner similar to that described above.

Next, one example method of correcting measurement results using a value of the periphery of a head is described. The periphery of a head is measured using a tape measure or the like in advance of the main measurement, and the value of the result is input. Assuming that the head is approximately circular, the radius of curvature is calculated and obtained from the periphery of the head. For example, when the length of the periphery of the head is 57 centimeters (cm), the radius of curvature is about 9 cm.

A penalty may be given only based on such a radius of curvature. However, in the present embodiment, a method in which the shapes of the skull, skin, and the bone marrow fluid calculated from the periphery of the head is adopted.

As known in the art, a person whose periphery of his/her head is large tends to have a thicker skull. This tendency simply indicates that a person with a larger body (a person with a greater periphery for his/her head) has thicker bones to maintain his/her body. In other words, it is considered that a radius of curvature correlates with the thickness of skull.

In particular, in the present embodiment, optical models are adopted in which linear transformation is performed such that thickness of skull will be 5 mm and 6 mm when the radius of curvature is 8 cm and 10 cm, respectively.

Figure 65:
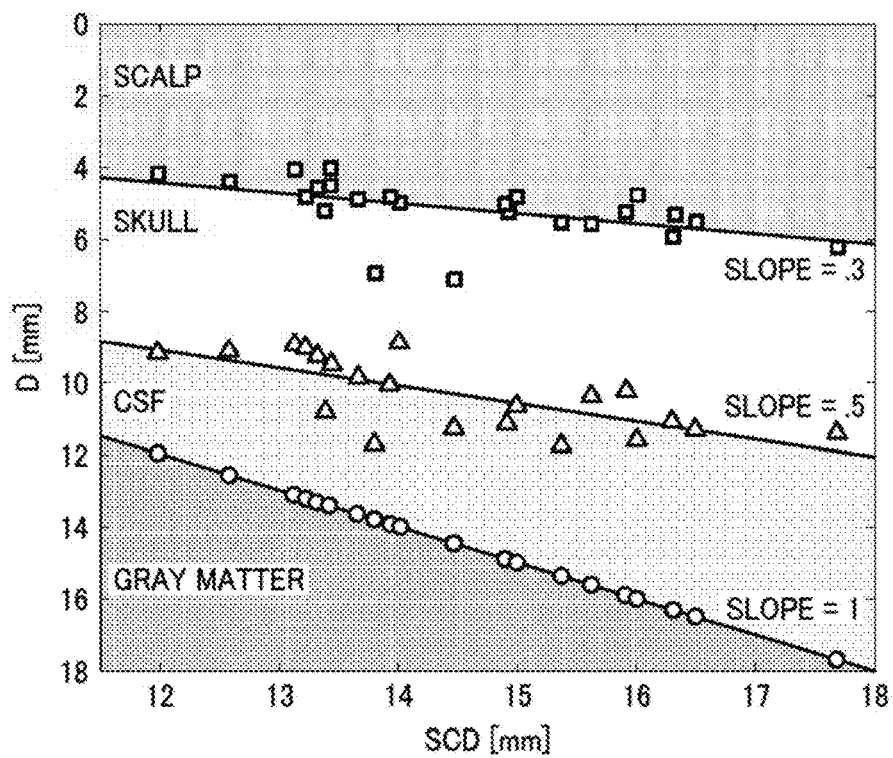
FIG. 65 is a graph illustrating the correlation between the thickness of three layers and the distance between the surface of the scalp and the surface of the brain, according to the second embodiment of the present invention.

In the four-layer model (a five-layer model from which a hair layer is removed), for example, the data as illustrated in FIG. 65 is taken into consideration. In FIG. 65, the correlation among the thickness of skin, the thickness of skull, and the thickness of the cerebrospinal fluid when the distance between the surface of the skin and the surface of the brain are assumed to be constant in the MRI images of about thirty people is taken into consideration.

Due to this configuration, a model that is considered to be the optimum one according to the periphery of the head and models that deviate from such an optimum model theoretically exist. A penalty is given to such an optimum model in a similar manner to an optical model where the correlation is examined between the age and the thickness of the layer of the cerebrospinal fluid as described above. As described above, the correlation may be examined between the input data and optical models to improve the accuracy of the selection of an optimum optical model. The use of the input data enables the correction to be carried out with high precision. The correction based on the correlation between the age and the thickness of the layer of the cerebrospinal fluid (bone marrow fluid) as described above is balanced with the correction of the present method. By so doing, the correction in view of the age and the size of a body can be achieved.

Figure 66:
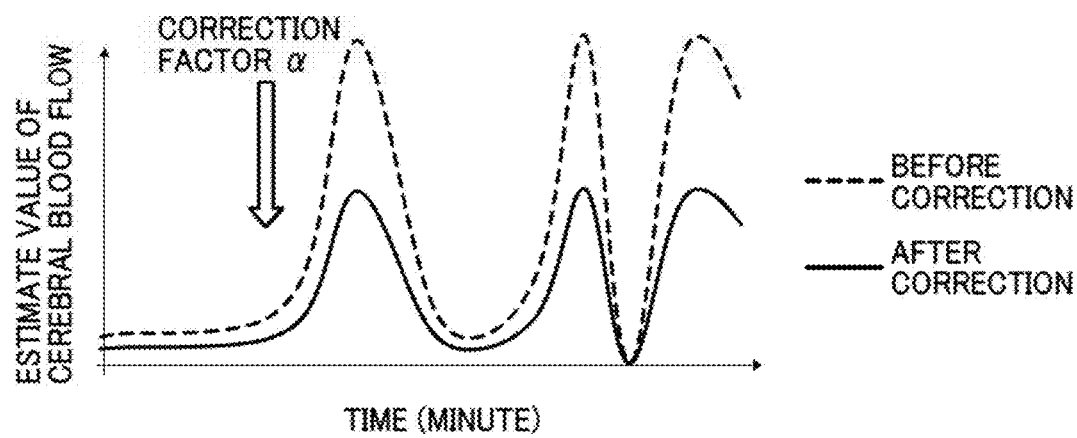
FIG. 66 is a graph illustrating the image of the correction of the amount of light, according to the second embodiment of the present invention.

After an optical model is selected, the detection values (measurement results) are corrected (step S55). FIG. 66 is a graph illustrating the image of the correction of the amount of light (detection values), according to the second embodiment of the present invention. In FIG. 66, the estimated amount of the cerebral blood flow is set to the vertical axis, and the horizontal axis serves as the time axis. For example, in FIG. 66, the value detected by one channel of a detection module DM attached to a forehead is illustrated. More specifically, such a detection value is obtained in a state where one channel, of the light source (surface emitting laser array) of a light source module LM, closest to a detection module DM emits light.

The term "before correction" in FIG. 66 indicates the amount of the light detected by a detection module DM. The indication of the amount of change in the vertical axis direction is similar to that of FIG. 62 as described above. However, the vertical axis is inverted compared with that of FIG. 62 so as to be consistent with the amount of cerebral blood flow. Accordingly, the vertical axis indicates a higher value when the amount of light is smaller. In FIG. 66, correction is performed such that the maximum light quantity value becomes zero in the first 20 seconds. The time periods during which a maximum value is indicated in the graph of FIG. 66 are time periods during which the cerebral blood flow increases at the forehead. The maximum value is determined by the optical properties of a test object. In the present embodiment, a correction factor α is defined, and such a correction factor α is simply applied to the changes in light quantity. By so doing, as illustrated in FIG. 66, although the shape of the plot stays similar and the rate of change does not change, the magnitude of the change is corrected.

As an optical model suited to the test object is selected by the methods as described above, a correction factor is determined for each optical model.

Such a correction factor is determined to serve as a reference, and the amount of cerebral blood flow can relatively be evaluated in view of the reference.

Also in the present embodiment, the optical model 1 illustrated in FIG. 17 is set to be the "standard configuration". Then, it is assumed in the present embodiment that the selected optical model is, for example, the optical model 2 illustrated in FIG. 18. The optical model 2 is selected when hairs exist directly below a light source module LM or a detection module DM. Note that when a hair only exists directly below either one of the pair of probes (the light source module LM or the detection module DM), another optical model may additionally be set.

As the irradiation light is absorbed by hairs in the optical model 2, the actually obtained amounts of light is small in the first place. For this reason, the changes in light quantity caused when the cerebral blood flow increases are expected to be small.

Figure 67:
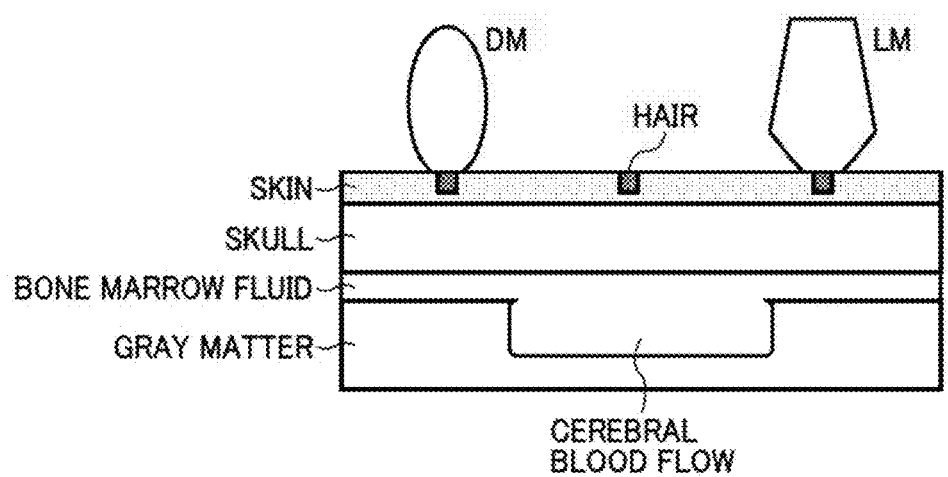
FIG. 67 illustrates an optical model in view of the cerebral blood flow, according to the second embodiment of the present invention.

In such an optical model, an optical simulation may be performed upon assuming that the cerebral blood flow exist, as illustrated in FIG. 67. Such an optical simulation where it is assumed that the cerebral blood flow exist is performed for all the optical models 1 to 8. In the optical simulation, how much the value detected by the detection module DM changes with reference to the "standard configuration" can be calculated and obtained. Then, the degree of the change is set as a correction value, and an optical model can be selected accordingly.

By performing correction, the amount of cerebral blood flow can be evaluated relative to the "standard configuration". Due to such a relative evaluation, the amount of cerebral blood flow can be compared with any test subject. FIG. 68 is a diagram depicting correction factors for each optical model, according to the second embodiment of the present invention. In other words, FIG. 68 depicts a simplified example of the relative evaluation described above. The correction factor is determined for each of the optical models with reference to "1". For example, when a hair intervenes as in the optical model 2, the correction factor is made greater than "1". By contrast, when a test subject has a white skin as in the optical model 3, the correction factor is made smaller than "1".

Figure 69:
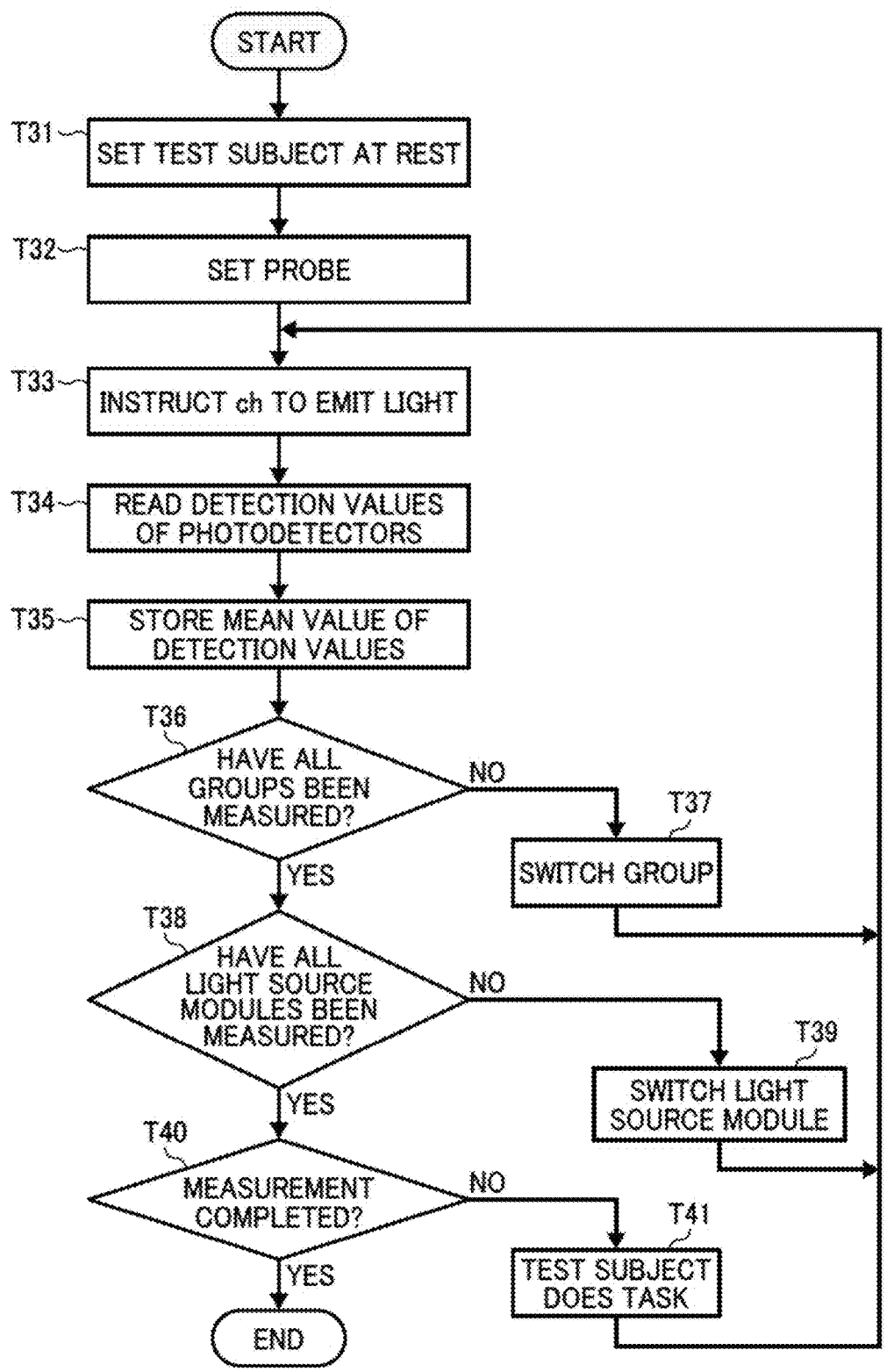
FIG. 69 is a flowchart of a method of detecting an optical property (position measuring method) according to the second embodiment of the present invention.

In the following description, a method of measuring the bloodstream inside the brain is described below with reference to the flowchart illustrated in FIG. 69. Firstly, the test subject is set at rest (step T31), and the probes (the detection module DM and the light source module LM) are set to the head (step T32). In so doing, each of the probes is carefully set (disposed) to a prescribed position using a fixation member so as not to clamp a hair or the like between the probe and the scalp. In this state, the channels of the light source module LM are instructed to emit light (step T33). The light source module LM is instructed to emit light (emit pulses of light) on a group-by-group basis, and the light-emission intensity is determined such that the current value becomes about 4 mW. The light emitting period is about several milliseconds, and the detection values of all the photodiodes are read and averaged during the light emitting period (step T34). Then, the averaged detection value is stored in the recording medium (step T35).

In a similar manner, the light emission of several milliseconds, the measurement, and the data storage are repeated for the next group (steps T36, T37, and T33 to T35). After the light emitting and measurement of all the light source modules LM are completed, the test subject is asked to do a task (steps T38 to T41). In the present embodiment, a commonly-used language fluency task is used. For a detailed description of such a language fluency task, see JP-2012-080975-A.

In the following description, cases in which the present method of measuring the bloodstream inside the brain is applied to the optical topography (registered trademark) in actual practice are described. As the regulations concerning remuneration for medical services in Japan were revised in April, 2014, the differential diagnosis of depression using the optical topography is now covered by the Japanese Health Service.

Figure 70:
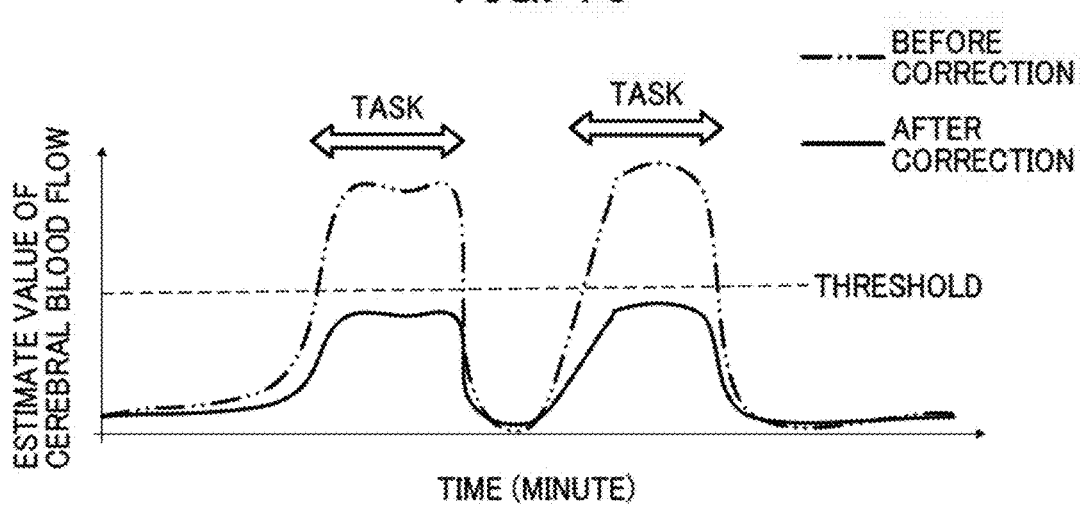
FIG. 70 is a diagram illustrating the image of the correction of the correction of the amount of light (depression sufferers), according to the second embodiment of the present invention.

As illustrated in FIG. 70, even if the cerebral blood flow appears to be large during a task (for example, language fluency test) before correction, the estimated value of the cerebral blood flow may decrease by performing correction with reference to the "standard configuration".

Figure 19:
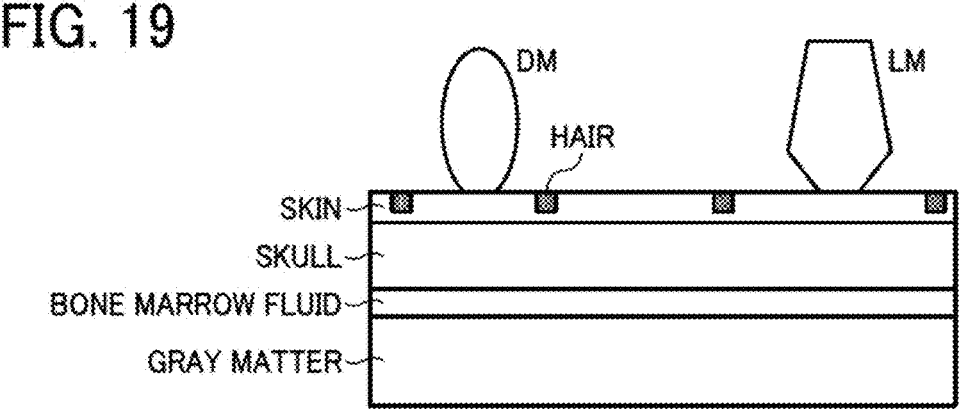
FIG. 19 illustrates an optical model 3 according to the first embodiment of the present invention.
Figure 21:
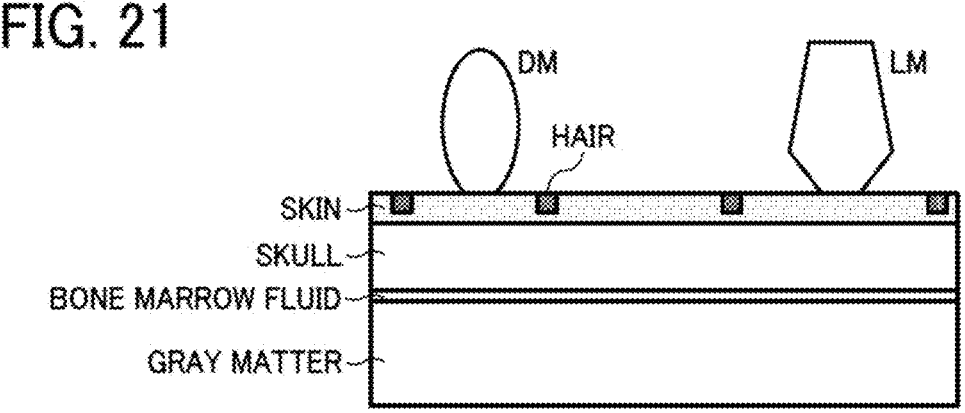
FIG. 21 illustrates an optical model 5 according to the first embodiment of the present invention.

This is dependent on the selected optical model. For example, such correction is effectively made when a hair exists near the detection module as illustrated in FIG. 18, when the color of skin is white as illustrated in FIG. 19, or when the bone marrow fluid layer is as thin as the twenties as illustrated in FIG. 21. When the estimated value for the cerebral blood flow does not reach a prescribed threshold, there is a possibility that the test subject suffers from depression.

Figure 20:
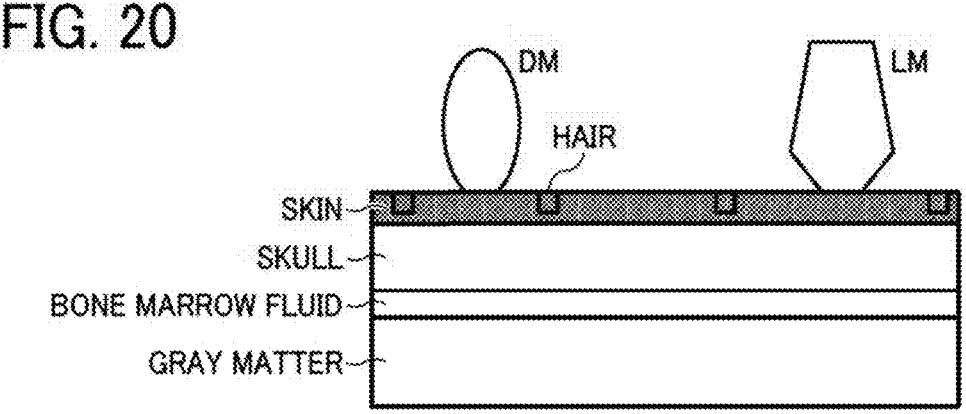
FIG. 20 illustrates an optical model 4 according to the first embodiment of the present invention.
Figure 22:
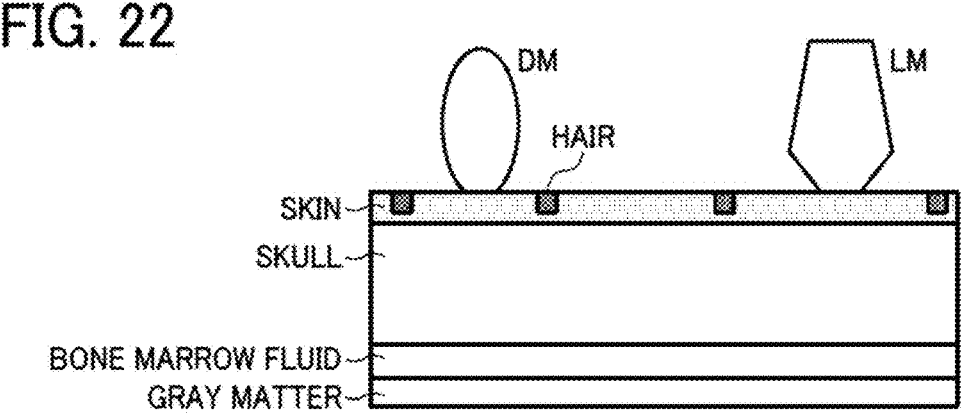
FIG. 22 illustrates an optical model 6 according to the first embodiment of the present invention.
Figure 23:
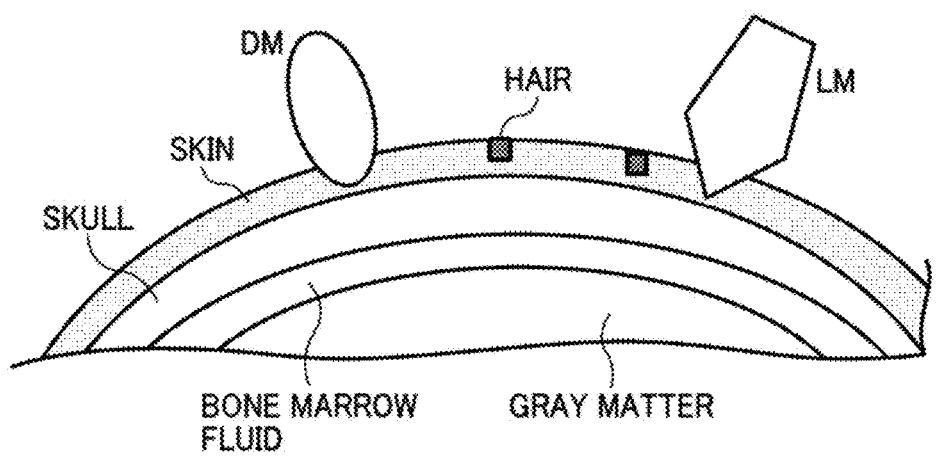
FIG. 23 illustrates an optical model 7 according to the first embodiment of the present invention.
Figure 24:
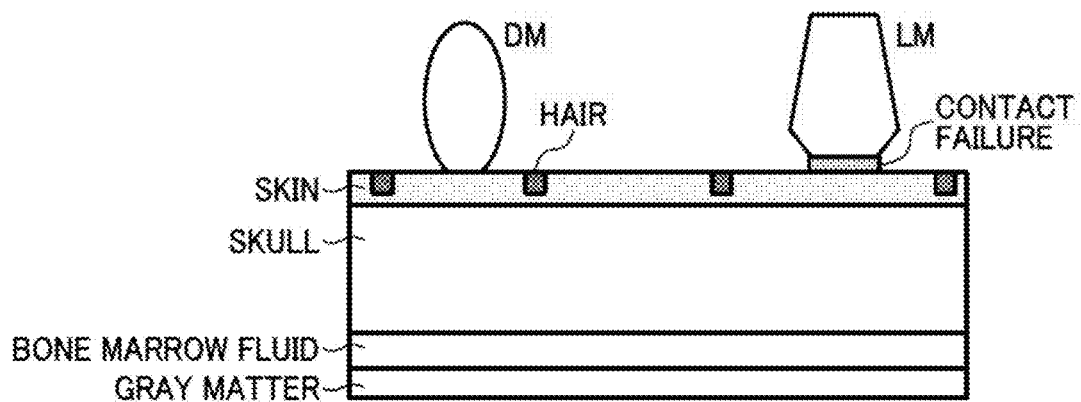
FIG. 24 illustrates an optical model 8 according to the first embodiment of the present invention.
Figure 71:
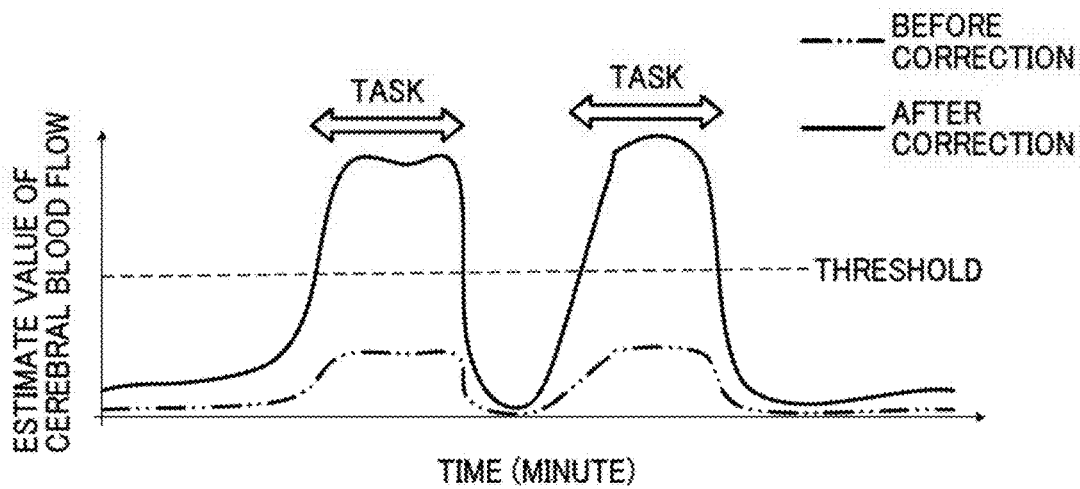
FIG. 71 is a diagram illustrating the image of the correction of the correction of the amount of light (able-bodied people), according to the second embodiment of the present invention.

By contrast, for example, when the color of skin is black as illustrated in FIG. 20 or when the size of the body is large and the skull is thick as illustrated in FIG. 22, the amount of cerebral blood flow may be detected to be seemingly small. However, if correction is made with reference to the "standard configuration", the test subject may be determined to have a value exceeding a threshold and belong able-bodied people. In other words, it is expected that the accuracy of the diagnosis of depression improves due to the correction as described above (see FIG. 71).

While a task (for example, a language fluency task) is being done by a test subject, the brain is activated, and a cerebral blood flow occurs only at the activated site. The bloodstream includes oxyhemoglobin and reduced hemoglobin, and light absorption occurs due to the bloodstream. In the present embodiment, the amount of the cerebral blood flow occurred at some sites are used just as an index to be compared with the values of the "standard configuration" to determine whether or not a disorder is present. In the clinical diagnosis of disorders or diseases, there is a demand to know more specifically how much and at what site of the brain the cerebral blood flow is occurring.

As described above, the optical examination method according to the second embodiment of the present invention is a method of performing an optical examination on a test object, using the optical sensor 10 including an irradiation system including a plurality of light source modules LM to irradiate an object to be measured with light, and a detection system including a plurality of detection modules DM to detect the amount of light that is emitted from the irradiation system to the object to be measured and propagated inside the object to be measured, and the method includes a step of obtaining a first detection light quantity distribution that is the detection light quantity distribution (light quantity distribution) obtained for each of the multiple optical models that simulate a test object, by performing the simulation where the optical sensor 10 is virtually used, a step of obtaining, using the optical sensor 10, the second detection light quantity distribution (light quantity distribution) that is the distribution of the amount of the light detected on the test object, and a step of selecting, based on the results of the comparison between the first and second detection light quantity distributions, an optical model suited to the test object from the multiple optical models. The method further includes a step of correcting the second detection light quantity distribution using the first detection light quantity distribution of at least one optical model (at least the optical model 1) including an optical model suited to the test object, selected from the multiple optical models.

In such a configuration, the second detection light quantity distribution that reflects the internal information (optical properties) of the test object can precisely be corrected.

In the step of correcting the second detection light quantity distribution, the correction factor α is calculated and obtained from the first detection light quantity distribution of the above at least one optical model, and the second detection light quantity distribution is corrected using the correction factor α. Accordingly, the second detection light quantity distribution can be corrected in a simplified manner.

Moreover, if at least one of the information of the gender, age, height, weight, the length of the periphery of the head, the thickness of the hairs, the density of the hair, and the color of the skin of a test object is used in the step of correcting the second detection light quantity distribution, the second detection light quantity distribution can be corrected with further improved precision.

Further, if detection is performed for 20 seconds or longer and the maximum value of the amounts of the detection light is used to calculate the second detection light quantity distribution in the step of obtaining the second detection light quantity distribution, the second detection light quantity distribution can be obtained with precision.

Third Embodiment

Next, a third embodiment of the present invention is described. In the third embodiment, the light source modules LM and detection modules DM that are equivalent to those of the first embodiment as described above are used for probes, and the layout of the probes is different from different from the other embodiments. Other than the layout of the probes, the configuration of the third embodiment is equivalent to that of the first embodiment as described above, and thus redundant description is omitted here.

In the second example of the first embodiment as described above, as illustrated in FIG. 39, two detection modules DM and two light source modules LM are disposed such that each of them is at the vertices of a roughly-drawn square. However, in the above layout, the optical path between each of the light source modules LM and detection modules DM becomes long at a point indicated by "X" in FIG. 39. For this reason, there is some concern that the amount of light received by the detection module DM is insufficient and the accuracy of detection may deteriorate due to the increased noise at that point.

Figure 72:
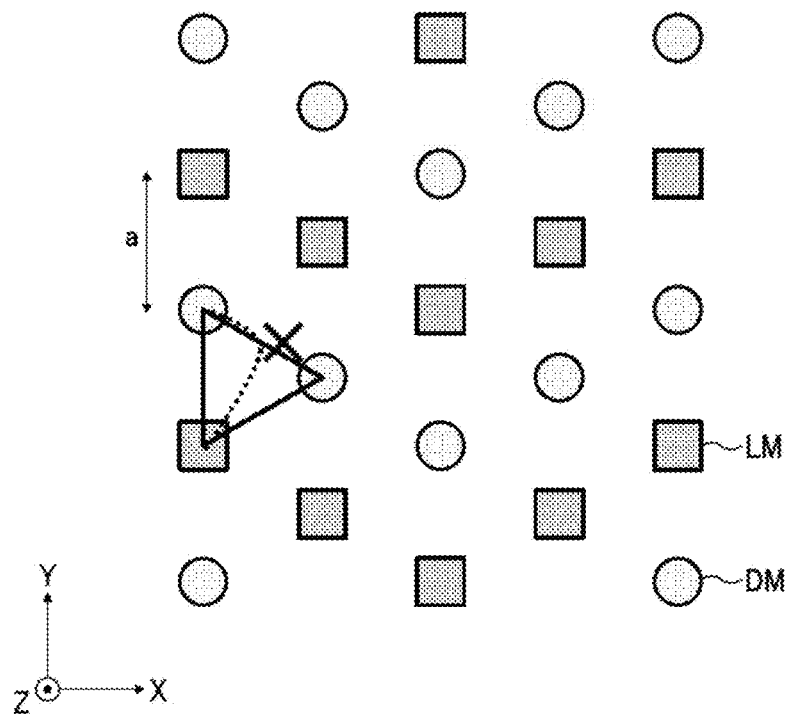
FIG. 72 is a diagram illustrating the arrangement of a plurality of light source modules and a plurality of detection modules in an optical sensor according to a third embodiment of the present invention.

In order to deal with such a situation, the layout of probes has been diligently studied, and it is found that the layout as illustrated in FIG. 72 is optimal. In FIG. 72, the multiple light source modules LM and detection modules DM are disposed for a test object such that two of either one of the light source modules LM and the detection modules DM are at two vertices of a regular triangle separately and one of the other one of the light source modules LM and the detection modules DM is at the remaining vertex of the regular triangle.

Here, for the purpose of simplification, the longest distances between the light source modules LM and the detection modules DM are compared with each other. Note that it is assumed that the space (pitch) between each of the light source modules LM and detection modules DM is "a". At the position of "X" in FIG. 39, the distance indicated by the broken lines is $\sqrt{2}a$ (about 1.414a). By contrast, the position of "X" in FIG. 72, the distance indicated by the broken lines is $(1+\sqrt{3})/2$ (about 1.366a). In short, when the longest distances between the light source module LM and the detection module DM are compared with each other between the two layouts of the probes in FIG. 39 and FIG. 72, the layout of the probes illustrated in FIG. 72 is shorter and thus is more desirable.

An inverse problem estimation was performed in the layout of the probes of FIG. 72 in a similar manner to the first embodiment, and as a result, it was found that the detectable area is widened in the layout of the probes according to the present embodiment.

Fourth Embodiment

Next, a fourth embodiment of the present invention is described. In the fourth embodiment, the layout of the multiple light source modules LM and multiple detection modules DM equivalent to that of the first embodiment as described above is adopted, and the layout of the channels of the light source module LM and the layout of the photodiodes of the detection module DM are different from those of the other embodiments. Other than the layout of the channels and the photodiodes, the configuration of the third embodiment is equivalent to that of the first embodiment as described above, and thus a redundant description is omitted here.

In the second example of the first embodiment, as illustrated in FIG. 39, the multiple light source modules LM and detection modules DM are arranged for the test object so as to be next to each other in both the X direction and the Y direction that are orthogonal to each other.

However, as described above, in the above layout, the optical path between each of the light source modules LM and detection modules DM becomes long at the point indicated by "X". For this reason, there is some concern that the amount of light received by the detection module DM is insufficient and the accuracy of detection may deteriorate due to the increased noise at that point.

Figure 73:
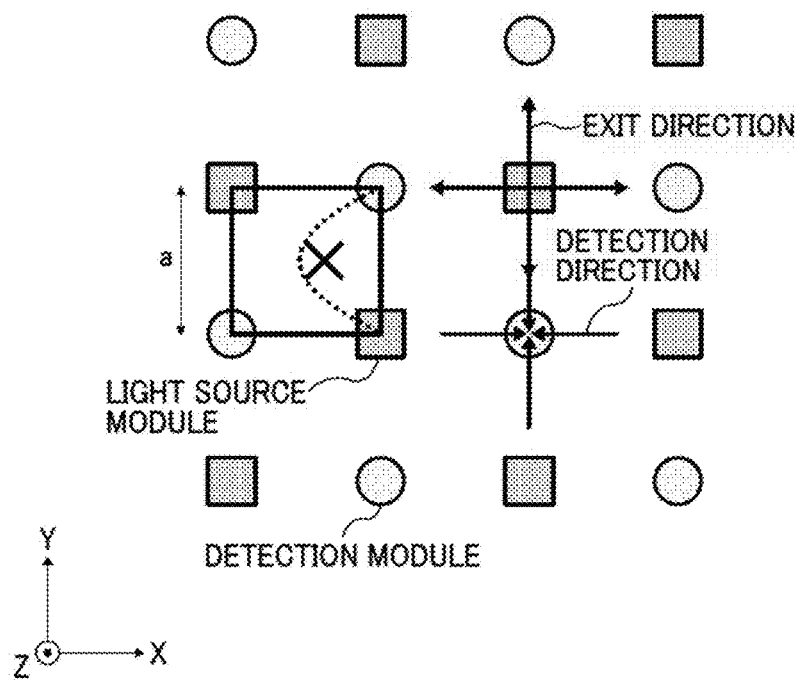
FIG. 73 is a diagram illustrating the exit directions of a plurality of light source modules and the detection directions of a plurality of detection modules in an optical sensor according to a control sample.

In the control sample illustrated in FIG. 73, the multiple light source module and the multiple detection module are arranged for the test object so as to be next to each other in both the X direction and the Y direction that are orthogonal to each other, and both the exit directions and the detection directions (i.e., the direction at which the light enters the photoreceptor) are parallel to the X direction and the Y direction. The lens that is disposed near the surface emitting laser has an optical property of point symmetry. Accordingly, the exit directions depend on the position of the surface emitting laser and the position of the group. As the lens that has an optical property of point symmetry, the detection directions depend on the division layout of the photodiode array.

Figure 74B:
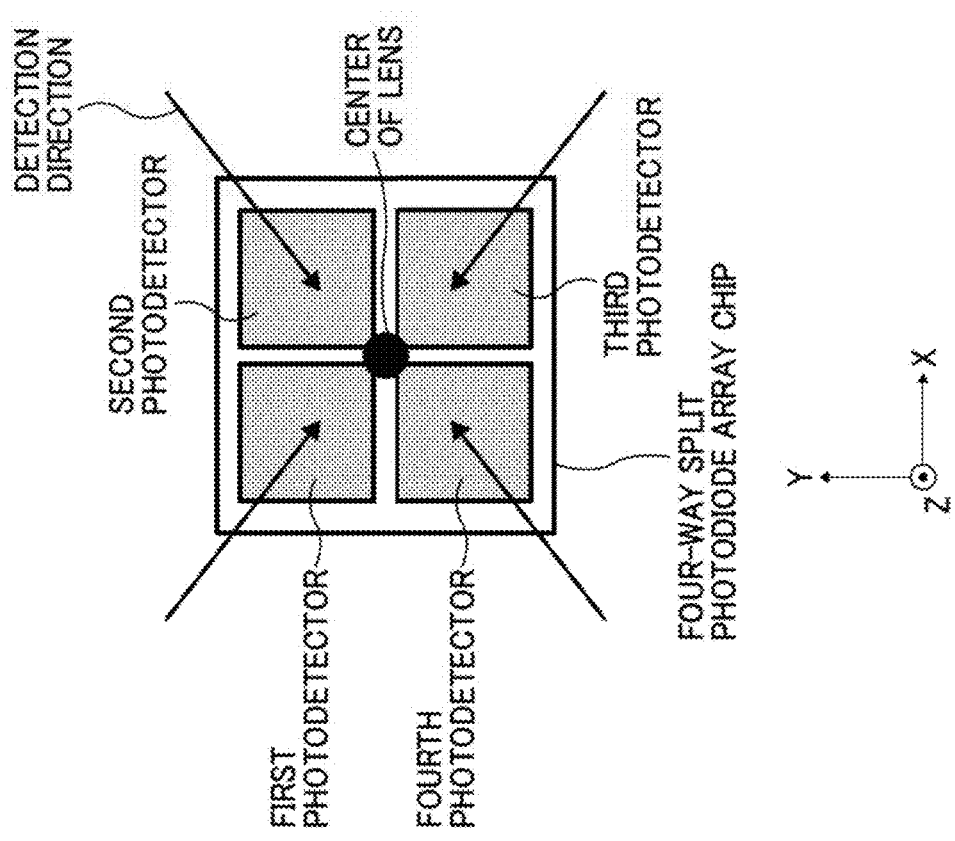
FIG. 74B is a diagram illustrating the detection directions of the four photodiodes of the photodiode array according to the fourth embodiment of the present invention.
Figure 74A:
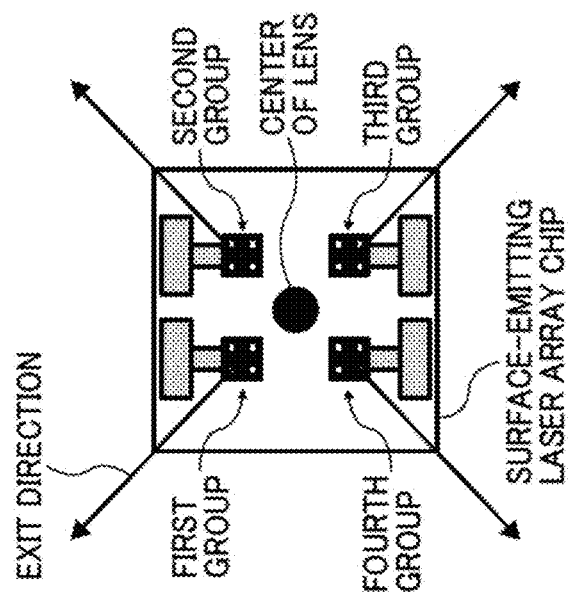
FIG. 74A is a diagram illustrating the exit directions of the four groups of the surface-emitting laser array chip according to a fourth embodiment of the present invention.
Figure 75:
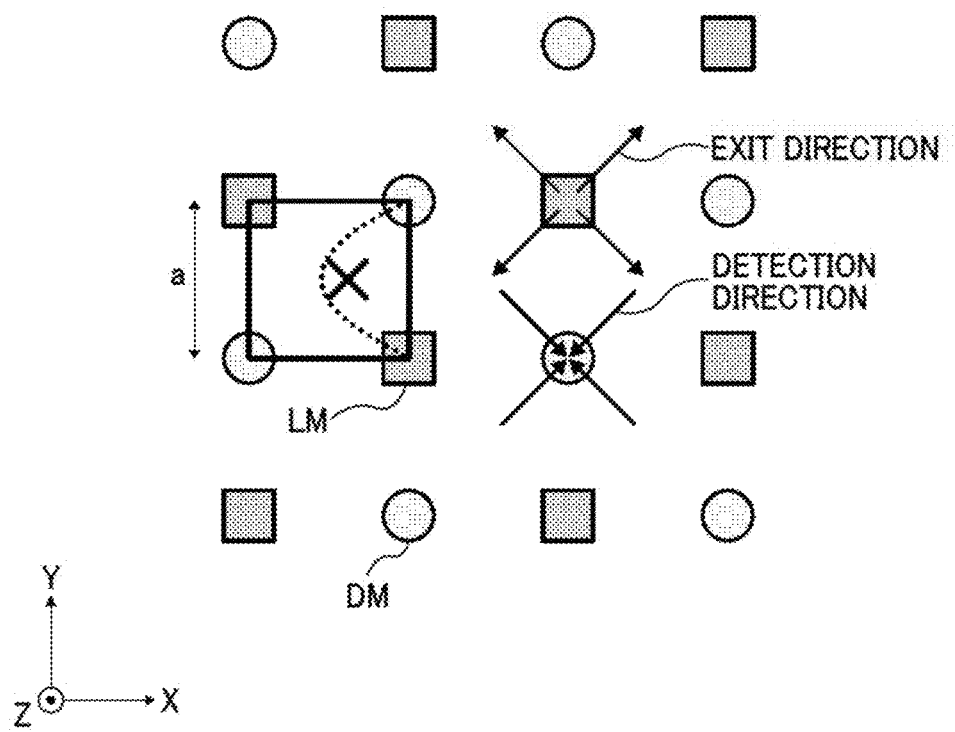
FIG. 75 is a diagram illustrating the exit directions of a plurality of light source modules and the detection directions of a plurality of detection modules in an optical sensor according to the fourth embodiment of the present invention.

In view of the above circumstances, the surface-emitting laser array chip is designed as illustrated in FIG. 74A, such that the exit directions are inclined with reference to the X direction and the Y direction in a planar view (when viewed from the +X direction). This happens because the center points of the groups are inclined with reference to the center of the lens. In a similar manner to the above, the center of the lens may be disposed at the center of the four-way split photodiode array chip (photodiode array chip) of the detection module DM, such that the detection directions (the incident directions at which the light enters the photoreceptors) become as illustrated in FIG. 74B. The detection directions and the exit directions of the above configuration are illustrated in FIG. 75 with the layout of the probes. The exit directions and the detection directions are inclined with reference to the X direction and the Y direction in a planar view (when viewed from the +X direction).

In such cases, as in the sensitivity distribution described above, the light is anisotropic. Accordingly, in the above configuration according to the fourth embodiment, a higher sensitivity is expected at the point X in FIG. 75.

An inverse problem estimation was performed in the layout of the probes of FIG. 74A and FIG. 74B in a similar manner to the first embodiment, and as a result it was found that the detectable area is widened in the layout of the probes according to the present embodiment.

Fifth Embodiment

Figure 80:
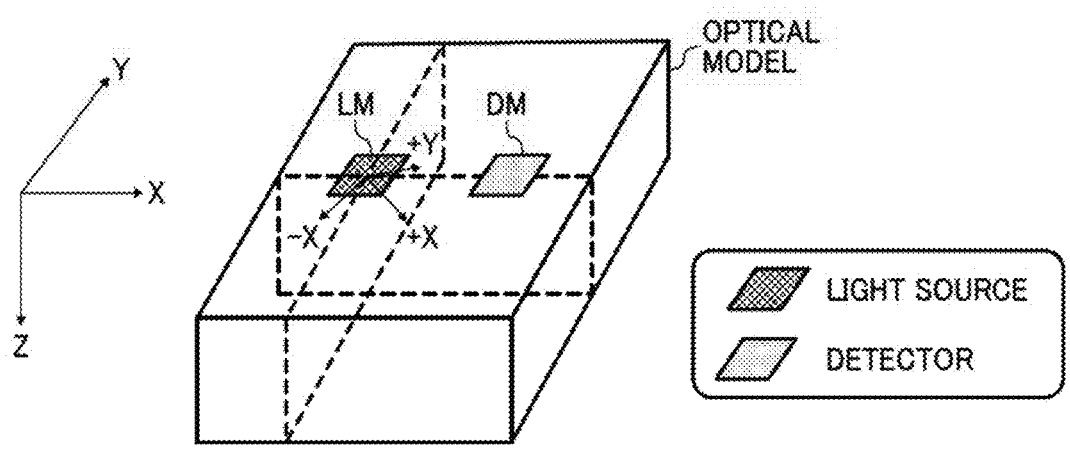
FIG. 80 is a diagram illustrating the arrangement of a light source module LM and a detection module DM on an optical model, according to a fifth embodiment of the present invention.

Next, a fifth embodiment of the present invention is described. FIG. 80 is a diagram illustrating a state in which a light source module LM and a detection module DM are virtually attached to an optical model (virtual model), according to a fifth embodiment of the present invention. In the present embodiment, an optical model indicates a rectangular-parallelepiped optical model (for example, the standard model) that simulates the brain of a living body.

In the following description, an XYZ three-dimensional rectangular coordinate system as illustrated in, for example, FIG. 80, is referred to where appropriate. In the optical model according to the present embodiment, the plane on which probes are virtually attached is parallel to the XY plane.

As illustrated in FIG. 80, the light source module LM and the detection module DM are aligned in the X direction. In the present embodiment, it is assumed that the incident angles that a plurality of (for example, three) light rays that are emitted from the light source module LM and are not parallel to each other form with the optical model is approximately 45 degrees. In the present embodiment, the incident angles are determined in view of the Snell law (the law of reflection) where the refractive index of the optical model is considered.

More specifically, the incident direction which the first light of three light rays that are emitted from the light source module LM (hereinafter, these light rays are referred to as "first to third lights") forms with the optical model is the direction that forms the angle of approximately 45 degrees with reference to the +Z direction and −X direction on the XZ plane, and the direction of the orthogonal projection vector of the incident direction with reference to the XY plane is in the −X direction.

The incident direction which the second light forms with the optical model is the direction that forms the angle of approximately 45 degrees with reference to the +Z direction and +X direction on the XZ plane, and the direction of the orthogonal projection vector of the incident direction with reference to the XY plane is in the +X direction.

The incident direction which the third light forms with the optical model is the direction that forms the angle of approximately 45 degrees with reference to the +Z direction and +Y direction on the YZ plane, and the direction of the orthogonal projection vector of the incident direction with reference to the XY plane is in the +Y direction.

In view of the above, for the sake of explanatory convenience, it is assumed in the following description according to the present embodiment that the incident direction of the first light is in the −X direction, the incident direction of the second is in the +X direction, and that the incident direction of the third light is in the +Y direction.

Figure 81:
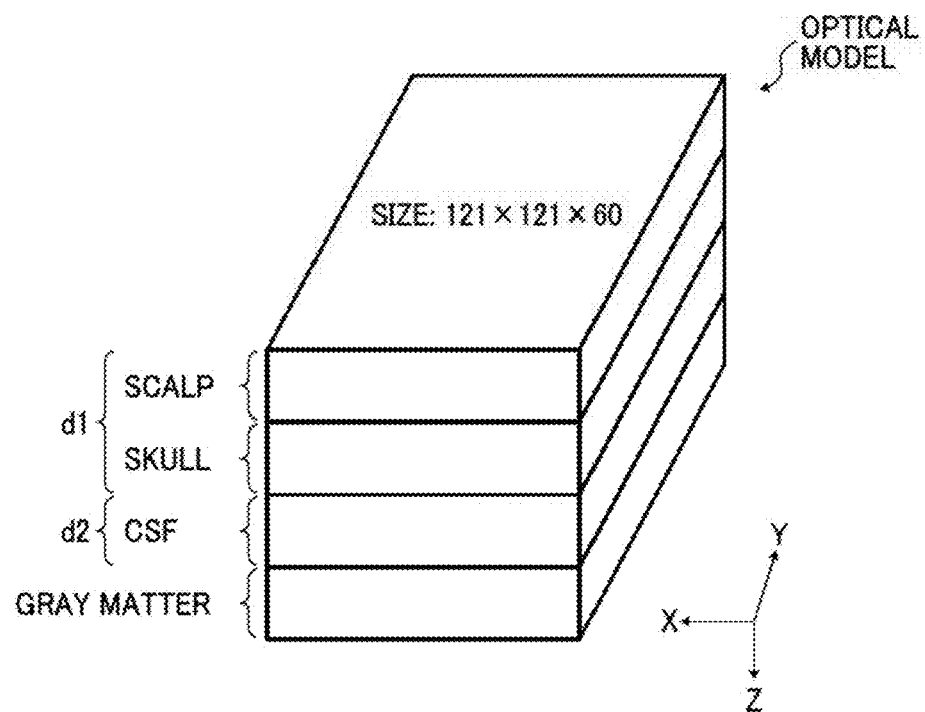
FIG. 81 illustrates an optical model according to the fifth embodiment of the present invention.
Figures 82, 83:
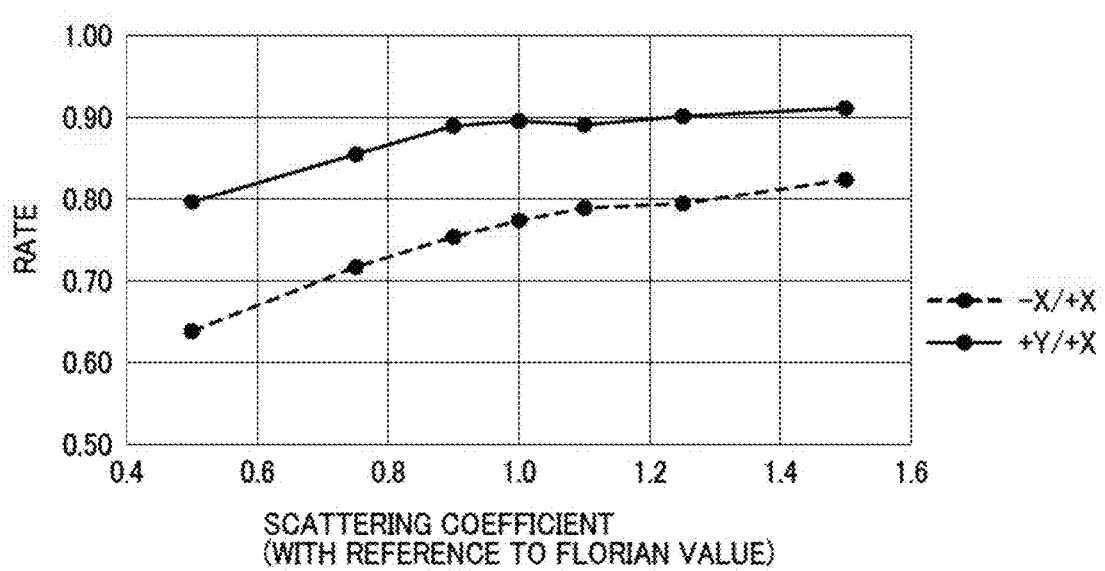
FIG. 82 is a diagram illustrating the optical constants of each layer in an optical model, according to the fifth embodiment of the present invention.
FIG. 83 is a graph illustrating the relation between the scattering coefficient and the rate of the amount of light of two different incident directions, according to the fifth embodiment of the present invention.

Also in the fifth embodiment, the calculations equivalent to the Monte Carlo simulation as described above are performed. As illustrated in FIG. 81, the optical model according to the present embodiment includes the four layers of a scalp layer, a skull layer, a cerebrospinal fluid (CSF) layer, and a gray matter layer. FIG. 82 is a diagram illustrating the optical constants of each of the layers in the optical model, according to the fifth embodiment of the present invention. As illustrated in FIG. 82, optical constants are set to each of the layers. Note that it is assumed that the sum of the thickness of the scalp layer and the thickness of the skull layer is d1, and the thickness of the cerebrospinal fluid layer is d2 (see FIG. 81).

In the optical model according to the present embodiment, the number of photons 1E9 is calculated to detect the number of photons (light quantity) that enters the detection module DM. In so doing, the calculation is performed for each incident direction of the first to third lights, and the ratio of the number of photons of the incident directions is plotted. Here, it is assumed that the number of photons (light quantity) of the first light is −X, the number of photons (light quantity) of the second light is +X, and that the number of photons (light quantity) of the third light is +Y.

FIG. 83 is a graph illustrating the relation between the scattering coefficient and the rate of the amount of light of two different incident directions, according to the fifth embodiment of the present invention. More specifically, in FIG. 83, −X/+X and +Y/+X obtained by varying the scattering coefficient of the layered product of, for example, the scalp layer and the skull layer with reference to the reference value (17.5) as depicted in FIG. 82 are plotted. FIG. 83 indicates that the −X/+X changes from about 0.62 to about 0.81 when the scattering coefficient is changed from the reference value of 0.5 times to 1.5 times. Note that it is assumed in the present embodiment that d1=9 mm and d2=3 mm. When the scattering coefficients of the cerebrospinal fluid layer or the gray matter layer are varied, a tendency similar to that of FIG. 83 is observed.

Figure 84:
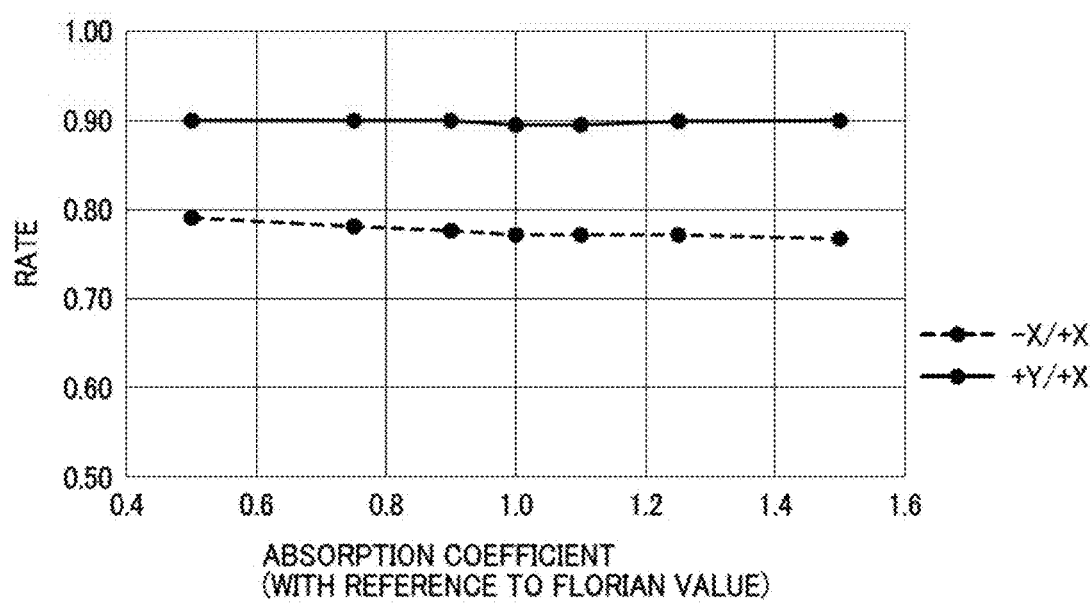
FIG. 84 is a graph illustrating the relation between the absorption coefficient and the rate of the amount of light of two different incident directions, according to the fifth embodiment of the present invention.

FIG. 84 is a graph illustrating the relation between the absorption coefficient and the rate of the amount of light of two different incident directions, according to the fifth embodiment of the present invention. FIG. 84 indicates that results similar to the graph with the scattering coefficients are obtained for absorption coefficients. In a similar manner to the above, it is assumed in the graph of FIG. 84 that d1=9 mm and d2=3 mm.

Figure 85A:
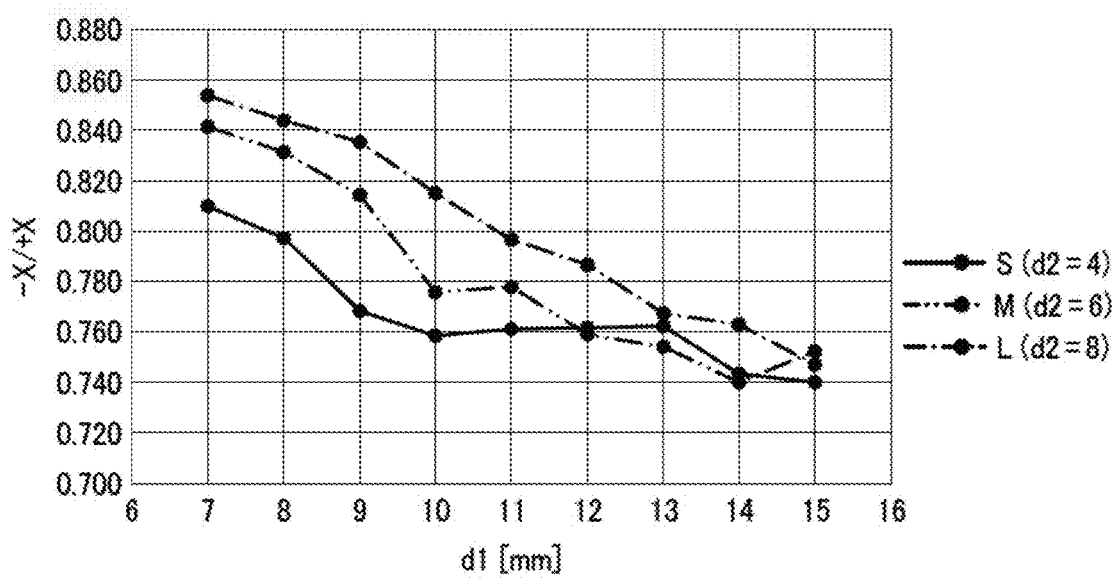
FIG. 85A and FIG. 85B are graphs each illustrating the relation between the sum of the thickness of scalp and the thickness of skull and the rate of the amount of light of two different incident directions, according to the fifth embodiment of the present invention.
Figure 85B:
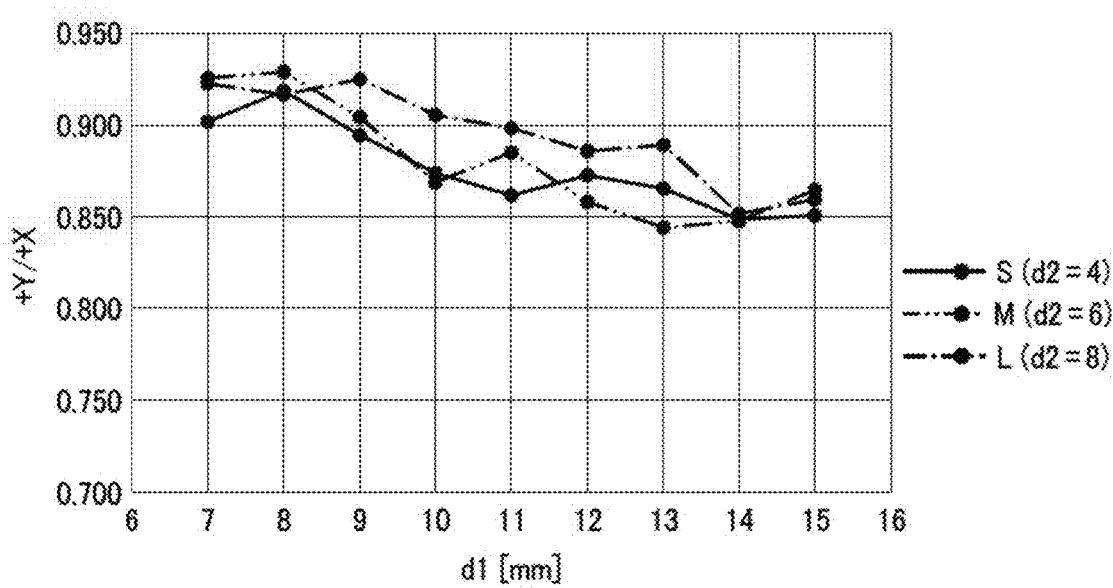

FIG. 85A and FIG. 85B are graphs each illustrating the relation between the sum of the thickness of scalp and the thickness of skull and the rate of the amount of light of two different incident directions, according to the fifth embodiment of the present invention. FIG. 85A and FIG. 85B indicate that the −X/+X and the +Y/+X change also when the thickness d1 or the thickness d2 varies.

As described above, the −X/+X and the +Y/+X change as the parameters for each layer of the optical model vary, and the range of such changes is about 0.6 to 0.95.

In view of the above, it is considered that the detection values of the −X/+X and the +Y/+X change may be used to correct the parameters for each layer of the optical model such that the parameters have values better suited to a living body (values matching or being close to the values unique to the living body).

However, the detection values include only two variables for the −X/+X and the +Y/+X change while there are four variables (parameters) (including the thickness d1, the thickness d2, the scattering coefficients, and the absorption coefficients). This indicates an unbalanced state, and the problem may mathematically appear defective. Still, for example, an inverse problem estimation may be used to perform an estimation in a simplified manner.

However, there is a problem that in an inverse problem estimation, an error occurs with a high probability. For this reason, a method in which the number of detection values can be increased and the variables can be determined as desired was studied. For example, as a simplified method, the periphery of the head of a test object may be measured, and the thickness d1 of the layered product of the scalp and the skull may be detected.

FIG. 86 is a diagram illustrating the correlation between the thickness of three layers and the distance between the surface of the scalp and the surface of the brain (cortex), according to the related art (see Plos one e26377 Volume 6 Issue 10 (2011) Florian B. Heaussinger). For example, in drawing of FIG. 86 cited from the research paper, a method is suggested in which a large amount of data is obtained and the thickness of the skull is calculated and obtained from the periphery of the head.

Alternatively, the thickness of the skull may be detected using an ultrasonic sensor. Alternatively, the thickness of each site of the skull may be detected using the computerized tomography (CT) scanner or the MRI images.

As described above, in addition to the use of the optical sensor 10, there are some methods of detecting the parameters of the optical model. In particular, the thickness d1 and d2 can be detected with high accuracy using such methods. If d1 and d2 are determined, the remaining factors are the scattering coefficients and the absorption coefficients.

In such a configuration, the variables include the two parameters (scattering coefficients and absorption coefficients), and the detection values include the −X/+X and the +Y/+X. However, these detection values are not independent from each other. For this reason, another independent detection value is desired.

In view of the above circumstances, in the optical sensor 10 that includes a plurality of light source modules LM and a plurality of detection modules DM, in addition to the multiple exit angle method (in which a plurality of light rays that are not parallel to each other are emitted to the same point of an object to be measured), it is desired that a multiple distance method be used in which there are variety of multiple distances between the light source modules LM and the detection modules DM.

See, for example, JP-5202736-B for such a multiple distance method. In such a multiple distance method, values unique to a test object, for example, the bone density or the color of skin, are used as the optical constants. For this reason, the dependency on the sites of the head is low. In other words, the function of correction is substantially satisfactory as long as any one portion of the head is detected and the detection results are corrected.

When the multiple exit angle method and the multiple distance method are used in combination, for example, a plurality of light source modules LM and a plurality of detection modules DM of the multiple exit angle method may alternately be arranged in a grid pattern at prescribed intervals (for example, 30 mm), or a plurality of detection modules DM may additionally be arranged with reference to the light source modules LM that are firstly arranged at prescribed intervals (for example, 5 mm) (see FIG. 87). Alternatively, a plurality of light source modules LM may additionally be arranged with reference to the detection modules DM that are firstly arranged at prescribed intervals (for example, 5 mm) (see FIG. 87).

By so doing, the gap (distance) among the light source modules LM and the detection modules DM has a plurality of variations, and the multiple exit angle method and the multiple distance method can be used in combination.

FIG. 88 is the equation related to light propagation of the multiple distance method, according to the related art (see 11 Feb. 2002/Vol. 10, No. 3/OPTICS EXPRESS 159). When the multiple distance method is adopted, the equation related to light propagation as depicted in FIG. 88 is used. In the equation, $\varphi$(rs rd) indicates the amounts of the light that propagates from rs (light source) to rd (photodetector). $\mu s'$ denotes the scattering coefficient converted from the anisotropy, and pa denotes the absorption coefficient. rs denotes the position of the light source, and rd denotes the position of the photodetector. D, S, and $\upsilon$ denote coefficients. FIG. 89A and FIG. 89B indicate the results of plotting the rates of the amount of light in the equation related to the light propagation depicted in FIG. 88, where $\mu s'$ is the variable.

The rates of the amount of light in FIG. 89A indicate the values in the multiple distance method, and the rates of the amount of light in FIG. 89B indicate the values in the multiple exit angle method (−X/+X). Note that the values in the multiple distance method indicate the ratio of the total amount of the light received by a detection module DM where the distance from a light source module LM is 5 mm (total detection value: the sum of a plurality of detection values) to the total amount of the light received by a detection module DM where the distance from a light source module LM is 30 mm (total detection value: the sum of a plurality of detection values).

In FIG. 89A, for example, three candidates (0.50, 1.00, and 1.50) for the absorption coefficient pa are indicated.

In FIG. 89A, the graphs of the rates of the amount of light of the multiple distance method are upward-sloping as the scattering coefficient $\mu s'$ increases, for any of the absorption coefficients $\mu a$. In FIG. 89A, when the rates of the amount of light, i.e., the values in the present multiple distance method, are, for example, 80, the scattering coefficient $\mu s'$ can be narrowed down to one of the value (0.65) indicated by arrow (1), the value (1.00) indicated by arrow (2), and the value (1.45) indicated by arrow (3).

On the other hand, in FIG. 89B, the graphs of the rates of the amount of light (−X/+X) of the multiple exit angle method are downward-sloping as the scattering coefficient $\mu s'$ increases, for any of the absorption coefficients pa.

In view of the above, the scattering coefficient $\mu s'$ where the rate of the amount of light in FIG. 89A is, for example, 80, and the rate of the amount of light in FIG. 89B is, for example, 65 is approximately estimated to be the value (1.00, equal to the reference value) indicated by arrow (2) among the values indicated by arrows (1) to (3). In other words, the scattering coefficient $\mu s'$ can be obtained if the values of the multiple exit angle method and the multiple distance method are known.

As described above, as the scattering coefficient changes, the rate of the amount of light changes differently between the multiple exit angle method and the multiple distance method. For this reason, the rates of the amount of light according to the multiple exit angle method and the rates of the amount of light according to the multiple distance method can be used as independent variables. It is considered that they can be used as independent variables because the exiting position (emitting position) appears to be shifting widely in the multiple exit angle method as the scattering coefficient $\mu s'$ decreases.

Figure 90A:
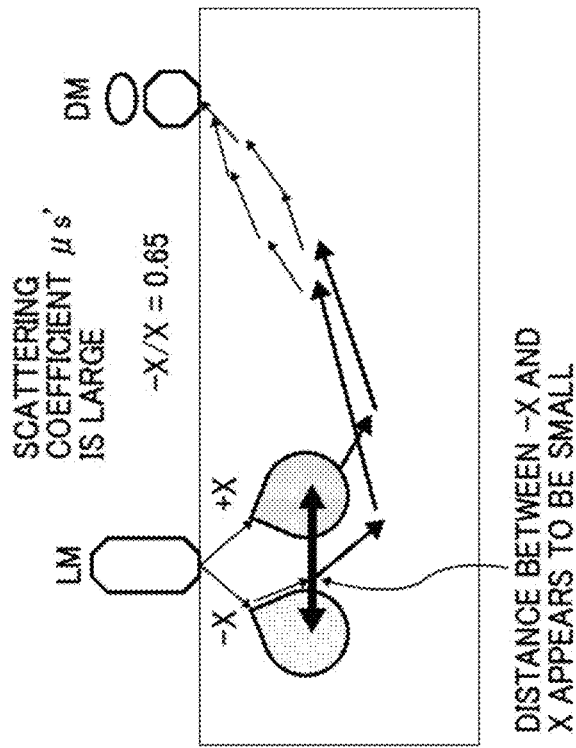
FIG. 90A is a diagram illustrating the propagation of light when the scattering coefficient is small, according to the fifth embodiment of the present invention.
Figure 90B:
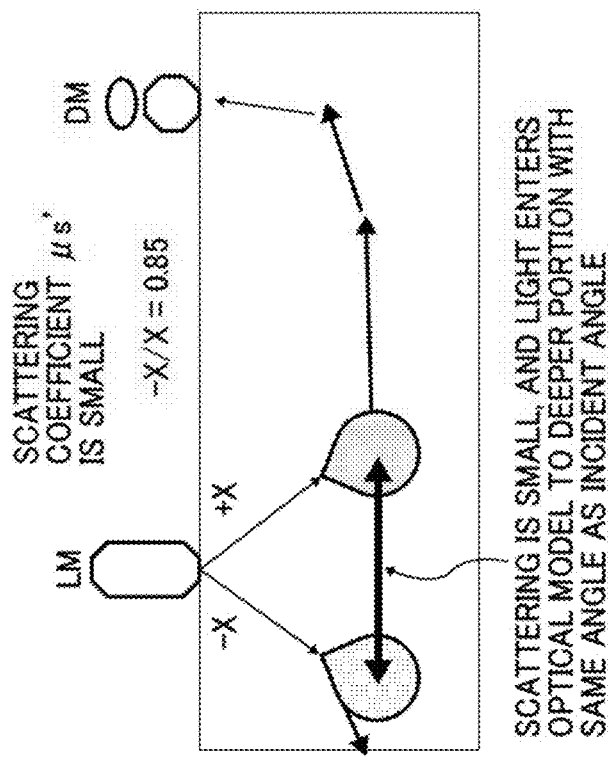
FIG. 90B is a diagram illustrating the propagation of light when the scattering coefficient is large, according to the fifth embodiment of the present invention.

FIG. 90A is a diagram illustrating the propagation of light when the scattering coefficient is small, according to the fifth embodiment of the present invention. FIG. 90B is a diagram illustrating the propagation of light when the scattering coefficient is large, according to the fifth embodiment of the present invention. FIG. 90A and FIG. 90B illustrate the physical phenomenon as described above, by way of example. As illustrated in FIG. 90A, when the scattering coefficient $\mu s'$ is small, two light rays (the two light rays whose incident directions are in the −X direction and the +X direction, respectively), which are not parallel to each other and emitted from a light source module LM and enter the same point of an optical model, enter a deep portion of the optical model. Accordingly, the positions with the maximum distance that the light can reach in the optical model are widely apart from each other, and the −X/+X (the rate of the amount of light) increases.

By contrast, as illustrated in FIG. 90B, when the scattering coefficient $\mu s'$ is large, two light rays (the two light rays whose incident directions are in the −X direction and the +X direction, respectively), which are not parallel to each other and emitted from a light source module LM and enter the same point of an optical model, disperse at a shallow portion of the optical model. Accordingly, the positions with the maximum distance that the light can reach in the optical model are not very much apart from each other, and the −X/+X (the rate of the amount of light) becomes small.

In other words, as the scattering coefficient $\mu s'$ is smaller, the positions with the maximum distance that the two light rays that are not parallel to each other can reach in the optical model are widely apart from each other, and the −X/+X (the rate of the amount of light) increases.

The foregoing represent the findings obtained as the multiple exit angle method is dealt with for the first time. It is believed unlikely that such a phenomenon would be considered obvious by those working in the art. The dependency on the scattering coefficient in the multiple exit angle method is approximately opposite that of the multiple distance method.

For this reason, as illustrated in FIG. 89A and FIG. 89B, the values obtained in the multiple exit angle method and the values obtained in the multiple distance method can be used as independent variables.

It is also considered that as the absorption coefficient is smaller, the positions with the maximum distance that the two light rays that are not parallel to each other can reach in the optical model are widely apart from each other. For this reason, the absorption coefficient can be calculated in a similar manner to the scattering coefficient (by plotting the rates of the amount of light with a plurality of absorption coefficients as in FIG. 89A and FIG. 89B where the horizontal axis is to be replaced with the absorption coefficient).

Accordingly, in a similar manner to the optical models as described above, the scattering coefficient and the absorption coefficient of a test object (for example, a living body) can be obtained by using the multiple exit angle method and the multiple distance method in combination.

In particular, the rate of the amount of light of, for example, −X/+X and +Y/+X takes an approximately constant value regardless of the state of the attachment of the probes on a test object (such a state includes, for example, the involvement of a foreign substance between the test object and each of the probes), and thus the error in detection can be reduced. Accordingly the scattering coefficients and the absorption coefficients can be obtained with precision.

In other words, as the values obtained in the multiple exit angle method are independent from the values obtained in the multiple distance method, the scattering coefficients and the absorption coefficients, which are two major parameters of the optical properties of the test object, can be obtained with precision. Then, by replacing the scattering coefficients and the absorption coefficients of the optical model that serves as a reference (for example, the standard model) with the obtained scattering coefficients and absorption coefficients, respectively, the optical model can be corrected to an optical model that is better suited to the test object. Further, by using the corrected optical model, the individual difference can be corrected, and the amount of cerebral blood flow can accurately be quantified. The correct diagnosis can be made based on the quantified amount.

As described above, the optical examination method according to the fifth embodiment of the present invention is a method of performing an optical examination on a test object, using the optical sensor 10 including an irradiation system including at least one light source module LM (light irradiator) configured to irradiate an identical point of an object to be measured with a plurality of light rays that are not parallel to each other, and a detection system including at least one detection module DM (photodetector) to separately detect the amounts of the multiple light rays that are emitted from the irradiation system to the object to be measured and have propagated inside the object to be measured, and the method includes a step of obtaining, using the optical sensor 10, the first detection light quantity distribution that is the distribution of the amount of the light detected on the test object, and a step of correcting, using the ratio of a plurality of detection values of a detection module DM included in the first detection light quantity distribution, an optical model that simulates the test object.

In such a configuration, the error can be reduced by using the ratio of a plurality of detection values. The error in detection value occurs due to, for example, dust or hairs existing on the interface between the test object and the front end of each of the probes. For this reason, the error in detection value greatly varies depending on the condition of the contact between the probes and the test object. By contrast, the value of the "ratio" of two detection values obtained under the same condition of the contact between the probes and the test object is approximately constant regardless of the error. Accordingly, the error factor due to the condition of contact can be eliminated. The changes in such a "ratio" correlates with the changes in the parameters of the test object (for example, the scattering coefficients and the absorption coefficients). More specifically, the "ratio" decreases according to an increase in the scattering coefficient or absorption coefficient (see FIG. 89B).

As a result, the values of the parameters for the test object (for example, the scattering coefficients and the absorption coefficients) can be narrowed down with precision. In other words, useful information for the correction of an optical model can be obtained.

When the multiple light rays that are not parallel to each other include two light rays where the directions of the orthogonal projection vectors of the incident directions with reference to the test object have directions opposed to each other, the difference between the optical path lengths of the two light rays to the detection module DM can be expanded to a maximum. As a result, the difference in the detection value at the detection module DM between the two light rays can be increased to a maximum, and the accuracy of the detection improves.

It is desired that the detection system include a plurality of detection modules DM, and that the step of obtaining the first detection light quantity distribution include a sub-step of disposing a plurality of detection modules DM and light source modules LM on a test object such that the distances between at least two of the detection modules DM and one of the light source modules LM are different from each other. Moreover, it is desired that in the step of correcting the optical model, the optical model be corrected by further using the ratio of the sum of a plurality of detection values of one of the above at least two detection modules DM to the sum of a plurality of detection values of the other detection module DM.

It is desired that the irradiation system include a plurality of light source modules LM, and that the step of obtaining the first detection light quantity distribution that is the distribution of the amount of the light detected on the test object include a sub-step of disposing a plurality of light source modules LM and detection modules DM on a test object such that the distances between at least two of the light source modules LM and one of the detection modules DM are different from each other. Moreover, it is desired that in the step of correcting the optical model the optical model be corrected by further using the ratio of the sum of a plurality of detection values that the detection module DM separately detects a plurality of light rays, which are emitted from one of the above at least two light source modules LM and have propagated through the test object, to the sum of a plurality of detection values that the detection module DM separately detects a plurality of light rays, which are emitted from the other one of the above at least two light source modules LM and have propagated through the test object.

The changes in the "ratio" of the sum of a plurality of detection values detected by one detection module DM to the sum of a plurality of detection values detected by another detection modules DM correlates with the changes in the parameters of the test object (for example, the scattering coefficients and the absorption coefficients). More specifically, the "ratio" increases according to an increase in the scattering coefficient or absorption coefficient (see FIG. 89A).

In such a configuration, the value best suited to the test object can be selected from the values of the narrowed down parameters of the test object as described above (for example, the scattering coefficients and the absorption coefficients).

In such a configuration, the optical model can be corrected to an optical model that is better suited to the test object.

Accordingly, the accuracy of the examination improves.

Note that it is desired that the optical examination method according to the fifth embodiment further include a step of obtaining the second detection light quantity distribution that is the detection light quantity distribution obtained for the corrected optical model by performing a simulation where the optical sensor 10 is virtually used, and a step of obtaining estimating) the internal information of the test object (for example, the position of a light absorber) using the first and second detection light quantity distributions.

In this configuration, the internal information of the test object can precisely be obtained.

For example, except for the first and second embodiments as described above, an optical model suited to a test object can be selected from a plurality of optical models by a modification that adopts the multiple exit angle method and the multiple distance method in a similar manner to the fifth embodiment.

In other words, the optical examination method according to such a modification is a method of performing an optical examination on a test object, using the optical sensor 10 including an irradiation system including at least one light source module LM (light irradiator) and a detection system including at least one detection module DM to detect an amount of light that is emitted from the irradiation system to an object to be measured and has propagated inside the object to be measured, and the method includes a step of obtaining a first detection light quantity distribution that is the detection light quantity distribution obtained for each of the multiple optical models that simulate a test object, by performing the simulation where the optical sensor 10 is virtually used, a step of obtaining, using the optical sensor 10, the second detection light quantity distribution that is the distribution of the amount of the light detected on the test object, and a step of selecting, based on the first and second detection light quantity distributions, an optical model suited to the test object from the multiple optical models.

In the optical examination method according to the modification, the step of obtaining the second detection light quantity distribution that is the distribution of the amount of the light detected on the test object includes a sub-step of emitting a plurality of light rays that are not parallel to each other from a light source module LM to an identical point of the test object, and a sub-step of detecting, using a detection module DM, each of the amounts of a plurality of light rays that have propagated through the test object, and in the step of selecting, the ratio of a plurality of detection values of the detection module DM in the sub-step of detecting is used to select the optical model suited to the test object.

In such a configuration, the values of the parameters for the test object (for example, the scattering coefficients and the absorption coefficients) can be narrowed down with precision.

Accordingly, the accuracy of the examination improves.

In the optical examination method according to the modification, when the multiple light rays that are not parallel to each other include two light rays where the directions of the orthogonal projection vectors of the incident directions with reference to the test object have directions opposed to each other, the difference between the optical path lengths of the two light rays to the detection module DM can be expanded to a maximum. As a result, the difference in the detection value at the detection module DM between the two light rays can be increased to a maximum, and the accuracy of the detection improves.

In the optical examination method according to the modification, it is desired that the detection system include a plurality of detection modules DM, and that the step of obtaining the second detection light quantity distribution that is the distribution of the amount of the light detected on the test object further include, prior to the sub-step of emitting, a sub-step of disposing a plurality of detection modules DM and light source modules LM on a test object such that the distances between at least two of the detection modules DM and one of the light source modules LM are different from each other. Moreover, it is desired that in the step of selecting the optical model, the optical model suited to the test object be selected by further using the ratio of the sum of a plurality of detection values of one of the above at least two photodetectors to the sum of a plurality of detection values of the other photodetector.

It is desired that the irradiation system include a plurality of light source modules LM, and the step of obtaining the second detection light quantity distribution that is the distribution of the amount of the light detected on the test object further includes, prior to the sub-step of emitting, a sub-step of disposing a plurality of light source modules LM and detection modules DM on a test object such that the distances between at least two of the light source modules LM and one of the detection modules DM are different from each other. Moreover, it is desired that in the step of selecting the optical model, the optical model suited to the test object be selected from a plurality of optical models using the ratio of the sum of a plurality of detection values that the detection module DM separately detects a plurality of light rays, which are emitted from one of the above at least two light source modules LM and have propagated through the test object, to the sum of a plurality of detection values that the detection module DM separately detects a plurality of light rays, which are emitted from the other one of the above at least two light source modules LM and have propagated through the test object.

The changes in the "ratio" of the sum of a plurality of detection values detected by one detection module DM to the sum of a plurality of detection values detected by another detection modules DM correlates with the changes in the parameters of the test object (for example, the scattering coefficients and the absorption coefficients). More specifically, the "ratio" increases according to an increase in the scattering coefficient or absorption coefficient (see FIG. 89A).

In such a configuration, the value best suited to the test object can be selected from the values of the narrowed down parameters of the test object as described above (for example, the scattering coefficients and the absorption coefficients).

By so doing, an optical model suited to the test object can be selected from the multiple optical models.

Accordingly, the accuracy of the examination improves.

It is desired that the optical examination method according to the modification further include a step of obtaining (estimating) the internal information of the test object (for example, the position of a light absorber) using the first detection light quantity distribution of the selected optical model and the second detection light quantity distribution.

In this configuration, the internal information of the test object can precisely be obtained.

In the fifth embodiment and the modification as described above, light source modules LM and detection modules DM according to the multiple exit angle method are used to achieve the multiple distance method. However, instead of or in addition to such configurations, light irradiators or photodetectors that are designed for exclusive use in the multiple distance method may be used. The light irradiator that is designed for exclusive use in the multiple distance method is satisfactory as long as it can emit at least one ray of light to an object to be measured. The photodetector that is designed for exclusive use in the multiple distance method is satisfactory as long as it can detect at least one ray of light that has propagated through the object to be measured.

In the first, second, and fifth embodiments, and the modification as described above, the position of a light absorber is estimated. However, instead of or in addition to such configurations, the size of a light absorber may be estimated. Apart from the blood, the term "light absorber" is anything that absorbs light, for example, a cancer cell and a polyp.

In the first and second embodiments and the modification as described above, eight optical models are used. However, the number of optical models may be equal to or less than seven, or equal to or greater than nine. In any case, it is desired that parameters for the optical properties indicating the characteristics of a test object, in the absence of or in the in the presence of the cerebral blood flow, be the characteristics of an optical model.

In the first and second embodiments and the modification as described above, the layer structure (the number of layers) of each optical model is in five layers. However, the number of layers may be equal to or less than four, or equal to or greater than six. In such a configuration, it is desired that the layer structure include at least one layer that serves as error factor, for example, a hair layer.

Figure 78:
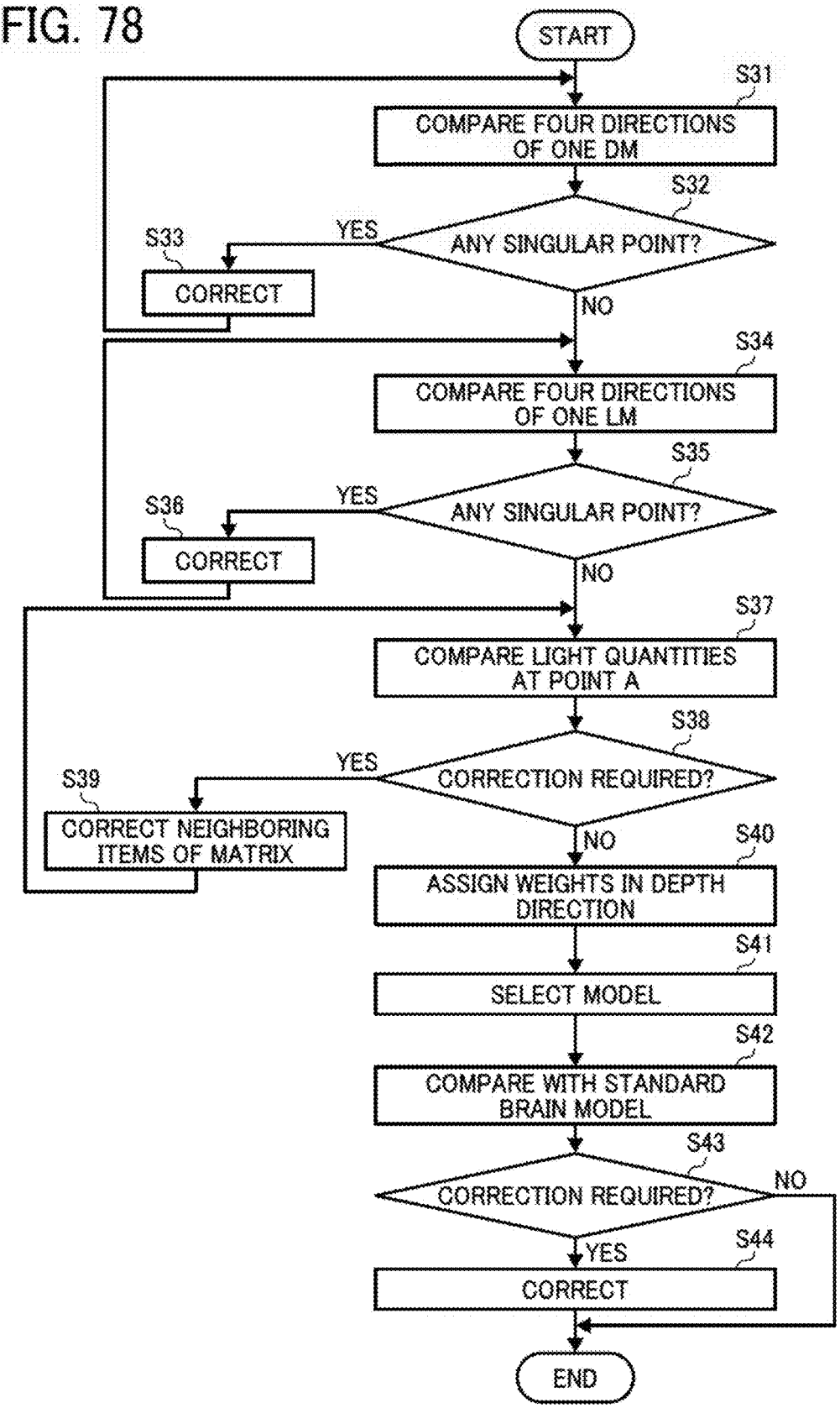
FIG. 78 is a first diagram illustrating the additional processes in the model selection processes of FIG. 33.

In a similar manner to the second embodiment, the optical examination method according to the first embodiment and the modification as described above may further include, prior to the step of obtaining the internal information of the test object (for example, the light absorber position estimation processes), a step of correcting the second detection light quantity distribution using the first detection light quantity distribution of at least one optical model (at least the optical model 1) including an optical model suited to the test object, selected from the multiple optical models (i.e., the optical models 1 to 8) (see the steps S42 to S44 in FIG. 78).

In such a configuration, the second detection light quantity distribution that reflects the internal information (optical properties) of the test object can precisely be corrected, and further, the estimation accuracy of the positions of the light absorbers also improves.

Figure 79:
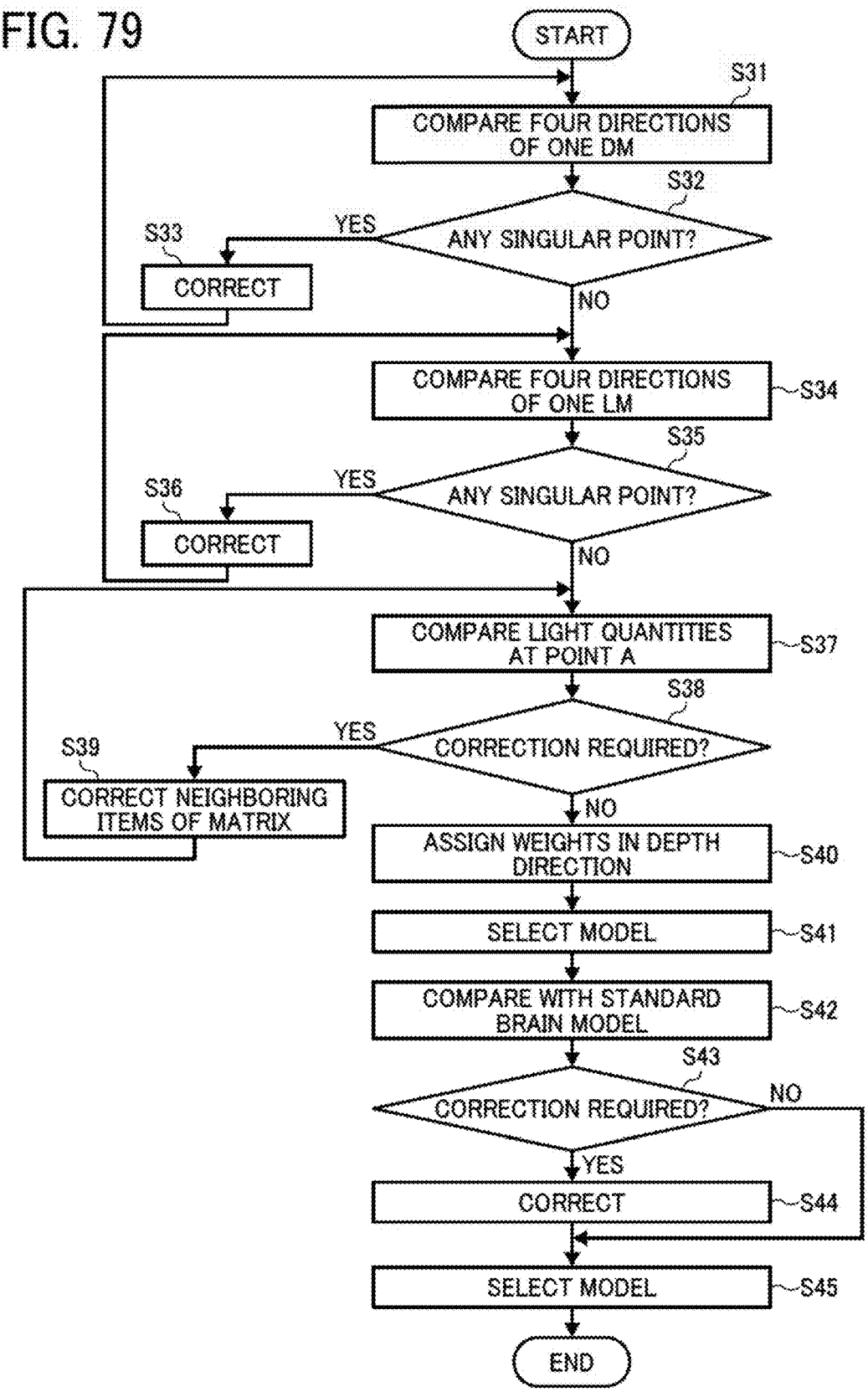
FIG. 79 is a second diagram illustrating the additional processes in the model selection processes of FIG. 33.

In the optical examination method according to the first embodiment and the modification as described above, after the step of correcting the second detection light quantity distributions, an optical model may be selected again (see step S45 of FIG. 79). In such cases, the accuracy of the selection of the optical model further improves.

In the optical examination method according to the first embodiment and the optical examination method according to the modification as described above, in a similar manner to the optical examination method according to the second embodiment, in the step of correcting the second detection light quantity distribution, the correction factor may be calculated and obtained from the first detection light quantity distribution of the above at least one optical model, and the second detection light quantity distribution may be corrected using the obtained correction factor. In such a configuration, the second detection light quantity distribution can be corrected in a simplified manner.

In the optical examination method according to the first embodiment and the optical examination method according to the modification as described above, in a similar manner to the optical examination method according to the second embodiment, if at least one of the information of the gender, age, height, weight, the length of the periphery of the head, the thickness of the hairs, the density of the hairs, and the color of the skin of a test object is used in the step of correcting the second detection light quantity distribution, the second detection light quantity distribution can be corrected with further improved precision.

In the optical examination method according to the first embodiment and the optical examination method according to the modification as described above, in a similar manner to the optical examination method according to the second embodiment, if 20 seconds or longer detection is performed and the maximum value of the amounts of the detection light is used to calculate the second detection light quantity distribution in the step of obtaining the second detection light quantity distribution, the second detection light quantity distribution can be obtained with precision.

The optical examination method according to the second embodiment and the optical examination method according to the modification as described above, in a similar manner to the optical examination method according to the first embodiment, may further include, prior to the step of selecting an optical model as described above, a step of correcting the first detection light quantity distribution. In a similar manner to the above, in such cases, the accuracy of the selection of the optical model improves.

Figure 33:
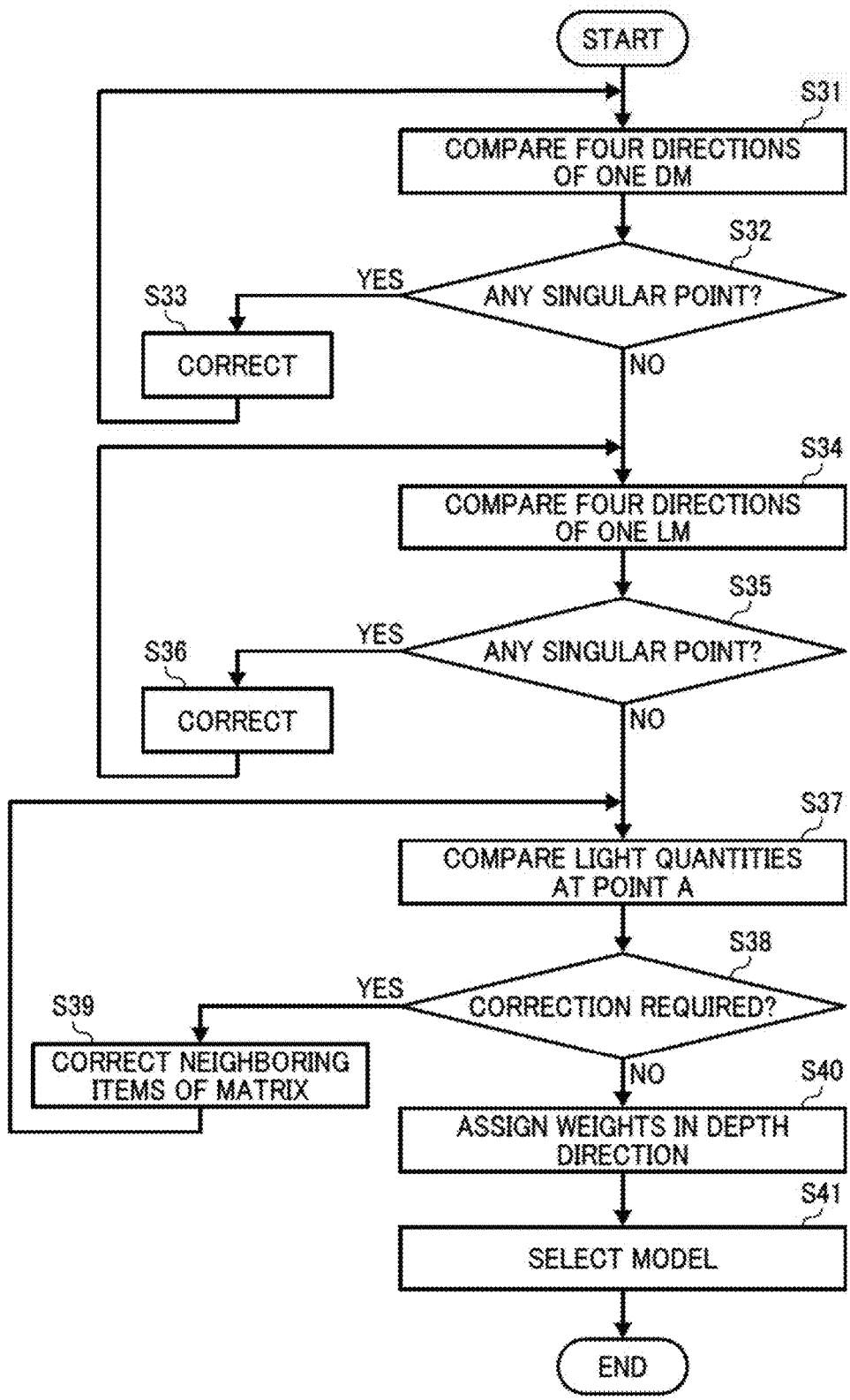
FIG. 33 is a flowchart of model selection processes in the optical examination method according to the first embodiment of the present invention.

In the optical examination method according to the second embodiment and the optical examination method according to the modification as described above, in a similar manner to the optical examination method according to the first embodiment, in the step of correcting the first detection light quantity distribution the amounts of the light rays that are emitted from the light source modules LM to an optical model and have propagated through the optical model in the above simulation, which are detected by the at least two detection modules DM that are adjacent to the light source module LM, may be compared with each other, and based on the results of the comparison, at least one of the amounts of the detection light detected by the at least two detection modules DM may be corrected (see steps S31 to S33 of FIG. 33).

In such a configuration, the error in the amounts of the light that is emitted from the light source modules LM to an optical model and has propagated through the optical model in the above simulation, which are detected by the multiple detection modules DM, can be reduced. In other words, the error due to a contact failure or the like caused between a detection module DM and the surface of an optical model in the above simulation can be reduced.

In the optical examination method according to the second embodiment and the optical examination method according to the modification as described above, in a similar manner to the optical examination method according to the first embodiment, in the step of correcting the first detection light quantity distribution, the amounts of the light rays that are emitted from at least two light source modules LM that are adjacent to the detection modules DM to an optical model and have propagated through the optical model in the above simulation, which are detected by the at least two detection modules DM, may be compared with each other, and based on the results of the comparison, the amount of the light that is emitted from at least one light irradiator of at least two light source modules LM, which is detected by the detection module DM, may be corrected (see steps S34 to S36 of FIG. 33).

In such a configuration, the error in the amounts of the multiple light rays that are emitted from the multiple light source modules LM to an optical model and have propagated through the optical model in the above simulation, which are detected by the multiple detection modules DM, can be reduced. In other words, the error due to a contact failure or the like caused between a light source module LM and the surface of an optical model in the above simulation can be reduced.

In the optical examination method according to the second embodiment and the optical examination method according to the modification as described above, in a similar manner to the optical examination method according to the first embodiment, it is assumed in the above simulation that two light source modules LM that are adjacent to each other are the first and second light source modules LM and two detection modules DM that are adjacent to each other and adjacent to each of the first and second light source modules LM are the first and second detection modules DM, in the step of correcting the first detection light quantity distribution, the amounts of the light rays 1 and 2 that are emitted from the first light source module LM to an optical model and have propagated through the optical model in the above simulation, which are detected by the first and second detection modules DM, are compared with the amounts of the light rays 3 and 4 that are emitted from the second light source module LM to the optical model and have propagated through the optical model, which are detected by the first and second detection modules DM. Moreover, based on the results of the comparison, at least one of the amounts of the detection light 1, 2, 3, and 4 may be corrected (see steps S37 to S39).

In such a configuration, the error that is caused due to a difference in the state of installation of four probes that are adjacent to each other in the above simulation can be reduced.

In the step of correcting the first and second detection light quantity distributions in the optical examination method according to the second embodiment and the modification of the present invention as described above, weights may be assigned in the depth direction (see step S40 of FIG. 33).

When the detection light quantity distribution of a test object is obtained in the first and second embodiments and the modification of the present the present invention as described above, such obtainment may be achieved by performing at least one of a series of the steps S31 to S33, a series of the steps S34 to S36, a series of the steps S37 to S39, and the S40, in the flowchart of FIG. 33. By so doing, the detection light quantity distribution of the test object can precisely be obtained.

Note that in the embodiments and the modification as described above, the number of the light source modules LM of the irradiation system and the number of the detection modules DM of the detection system may be varied as desired. It is satisfactory as long as the irradiation system includes at least one light source module LM. In a similar manner, it is satisfactory as long as the detection system includes at least one detection module DM. Moreover, it is desired that the multiple probes be disposed such that the light source module LM and the detection module DM are adjacent to each other (next to each other) in two directions that intersect.

In the embodiments and the modification as described above, the configuration of the light source module LM (light irradiator) may be changed as desired. For example, the layout or the number of surface-emitting laser array chips in the light irradiator may be changed as desired. Moreover, for example, the types, shapes, sizes, and the number of lenses may be changed as desired.

In the embodiments and the modification as described above, a surface emitting laser is used for the light source of a light irradiator. However, for example, an end-surface emitting laser (laser diode (LD)), a light-emitting diode (LED), organic electroluminescence (EL) element, and a laser other than semiconductor lasers may be used.

In the embodiments and the modification as described above, a prism is used for the reflection member of a light irradiator. However, other elements such as a mirror may be used instead of the prism.

The number of groups or layout in the surface-emitting laser array chip according to the second example, or the number of channels or the layout in each of the groups may be changed as desired.

The configuration of the detection module DM (photodetector) may be changed as desired. For example, the aperture may be omitted, or the split lens may be omitted.

As a matter of course, the shape, size, material, number, dimension, or numerical values of the elements or parts described above are given by way of example, and may be changed as desired.

As a matter of course, at least some of the configuration of the optical examination device or the optical sensor according to the embodiments or the modification of the present invention, or at least one of the steps of the optical examination method may be diverted among the embodiments, among the embodiments and the modification, or among the examples.

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

Further, as described above, any one of the above-described and other methods of the present invention may be embodied in the form of a computer program stored on any kind of storage medium. Examples of storage media include, but are not limited to, flexible disks, hard disks, optical discs, magneto-optical discs, magnetic tape, nonvolatile memory cards, read only memory (ROM), etc. Alternatively, any one of the above-described and other methods of the present invention may be implemented by ASICs, prepared by interconnecting an appropriate network of conventional component circuits, or by a combination thereof with one or more conventional general-purpose microprocessors and/or signal processors programmed accordingly.

What is claimed is:

1. A method of performing an optical examination on a test object, the method comprising:
   (a) obtaining, for each of a plurality of optical models that simulate the test object, a first detection light quantity distribution, by performing a simulation, by a processor executing a program of instructions stored in a non-transitory medium, of virtual measurements with an optical sensor including an irradiation system and a detection system, the irradiation system including at least one light irradiator, and the detection system including at least one photodetector to detect an amount of light that returns to the optical sensor from the test object after having been emitted from the irradiation system to a surface of the test object and propagated inside the test object;
   (b) obtaining a second detection light quantity distribution that is a distribution of an amount of light detected, by physical measurements using the optical sensor, on the test object, including
      (b1) emitting a plurality of light rays that are not parallel to each other from the light irradiator to an identical point of the test object, and
      (b2) detecting, using the photodetector, each of amounts of a plurality of light rays that have propagated through the test object to output a plurality of detection values of the photodetector;
   (c) determining, by the processor based on the first light quantity distribution and the second detection light quantity distribution, an optical model most similar to the test object amongst the plurality of optical models, by using a ratio of the plurality of detection values of the photodetector; and
   (d) performing, based on the optical model determined in (c), at least one of the following:
      (i) adjusting the second detection light quantity distribution corresponding to the physical measurements using the optical sensor;
      (ii) adjusting the amount of light that is emitted from the irradiation system of the optical sensor;
      (iii) adjusting the amount of detection light detected by the detection system of the optical sensor;

(iv) adjusting internal information of the test object determined based on the second detection light quantity distribution.

2. The method according to claim 1, wherein the plurality of light rays that are not parallel to each other include two light rays where directions of orthogonal projection vectors of incident directions with reference to the test object have directions opposed to each other.

3. The method according to claim 1, wherein the photodetector of the detection system includes a plurality of photodetectors, the obtaining in (b) of the second detection light quantity distribution further includes, prior to the emitting, disposing the plurality of photodetectors and the light irradiators on the test object such that distances between at least two of the photodetectors and one of the light irradiators are different from each other, and the determining in (c) determines one of the optical models most similar to the test object by further using a ratio of a sum of a plurality of detection values of one of the at least two of the photodetectors to a sum of a plurality of detection values of the other one of the at least two of the photodetectors.

4. The method according to claim 1, wherein the light irradiator of the irradiation system comprises a plurality of light irradiators, the obtaining in (b) of the second detection light quantity distribution further includes, prior to the emitting, a disposing the plurality of photodetectors and the light irradiators on the test object such that distances between at least two of the light irradiators and one of the photodetectors are different from each other, and the determining in (c) includes determining one of the optical models most similar to the test object from the plurality of optical models by further using a ratio of a sum of a plurality of detection values that the photodetector separately detects from a plurality of light rays, which are emitted from one of the at least two of the light irradiators and have propagated through the test object, to a sum of a plurality of detection values that the photodetector separately detects from a plurality of light rays, which are emitted from the other one of the at least two of the light irradiators and have propagated through the test object.

5. The method according to claim 1, further comprising:

determining a correction factor corresponding to the optical model determined in (c), and performing, based on the correction factor, at least one of the following:

(aa) adjusting the second detection light quantity distribution corresponding to the physical measurements using the optical sensor;

(bb) adjusting the amount of light that is emitted from the irradiation system of the optical sensor;

(cc) adjusting the amount of detection light detected by the detection system of the optical sensor;

(dd) adjusting internal information of the test object determined based on the second detection light quantity distribution.

6. The method according to claim 5, further comprising obtaining the internal information of the test object using the first detection light quantity distribution of the optical model determined in (c), and the second detection light quantity distribution.

7. The method according to claim 5, wherein the optical model includes a virtual layer between the surface of the test object and the light irradiator and the photodetector.

8. The method according to claim 5, wherein in the obtaining of the second detection light quantity distribution in (b), detection is performed for 20 seconds or longer and a maximum value of amounts of detection light is used to calculate the second detection light quantity distribution.

9. The method according to claim 5, further comprising correcting the second detection light quantity distribution based on at least one of gender, age, height, weight, length of a periphery of a head, thickness of hair, density of hair, and color of skin of the test object.

10. The method according to claim 5, wherein in each optical model amongst the plurality of optical models, the test object is represented by a combination of plural layers one stacked on another, and each layer of the plural layers being associated with an optical constant corresponding to the layer.

11. The method according to claim 5, further comprising correcting the first detection light quantity distribution prior to the determining in (c).

12. The method according to claim 11, wherein the at least one photodetector comprises a plurality of photo detectors, in the simulation, the light irradiator and the plurality of photodetectors are virtually installed in the optical model in such a manner that at least two of the plurality of photodetectors are adjacent to the light irradiator, and the correcting the first detection light quantity distribution compares amounts of light rays that are emitted from the light irradiator to the optical model and have propagated through the optical model in the simulation, which are detected by the at least two photodetectors that are adjacent to the light irradiator, with each other, and corrects, based on a result of comparison, at least one of amounts of detection light detected by the at least two photodetectors.

13. The method according to claim 11, wherein the at least one light irradiator comprises a plurality of light irradiators, in the simulation, the plurality of light irradiators and the photodetector are virtually installed in the optical model in such a manner that at least two of the plurality of light irradiators are adjacent to the photodetector, and the correcting the first detection light quantity distribution compares amounts of light rays that are emitted from the at least two of the light irradiators to the optical model and have propagated through the optical model in the simulation, which are detected by the photodetector that is adjacent to the at least two of the light irradiators, with each other, and corrects, based on a result of comparison, an amount of light that is emitted from at least one of the at least two light irradiators, which is detected by the photodetector.

14. The method according to claim 11, wherein the at least one light irradiator comprises a plurality of light irradiators, the at least one photodetector includes a plurality of photodetectors, in the simulation, the plurality of light irradiators and the plurality of photodetectors are virtually installed in the optical model in such a manner that the plurality of light irradiators and the plurality of photodetectors are adjacent to each other in both a first direction and a second direction that intersect, two of the light irradiators that are adjacent to each other are a first light irradiator and a second light irradiator and two of the photodetectors that are adjacent to each other and adjacent to each of the first light irradiator and the second light irradiator are a first photodetector and a second photodetector, and the correcting the first detection light quantity distribution compares, in the simulation, a first amount and a second amount of detection light of light rays that are emitted from the first light irradiator to the optical model and have propagated through the optical model, which are detected by the first photodetector and the second photodetector, with a third amount and a fourth amount of detection light of light rays that are emitted from the second light irradiator to the optical model and have propagated through the optical model, which are detected by the first photodetector and the second photodetector, and corrects, based on results of comparison, at least one of the first, second, third, and fourth amounts of detection light.

* * * * *